(12) United States Patent
Munoz et al.

(10) Patent No.: US 6,362,009 B1
(45) Date of Patent: Mar. 26, 2002

(54) SOLID PHASE SYNTHESIS OF HETEROCYCLES

(75) Inventors: Benito Munoz, San Diego; Chixu Chen, Carlsbad, both of CA (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 08/975,944

(22) Filed: Nov. 21, 1997

(51) Int. Cl.[7] .................. G01N 33/543; C07D 211/02; C07D 211/72; C07D 211/82

(52) U.S. Cl. .................. 436/518; 436/523; 436/524; 436/525; 436/526; 436/527; 436/528; 436/529; 436/530; 436/531; 435/DIG. 49; 546/1; 546/249; 546/290; 546/297; 546/298; 546/299; 546/304; 546/310; 546/314; 546/347; 546/348

(58) Field of Search .................. 546/1, 249, 290, 546/297, 298, 299, 304, 310, 314, 347, 348; 436/518, 523–531; 530/333, 334; 544/98, 358; 435/DIG. 49

(56) References Cited

U.S. PATENT DOCUMENTS

| | | | |
|---|---|---|---|
| 3,338,786 A | 8/1967 | Kuntsman et al. | 167/65 |
| 3,710,795 A | 1/1973 | Higuchi et al. | 128/260 |
| 3,856,937 A | 12/1974 | Waite | 424/115 |
| RE28,819 E | 5/1976 | Thompson | 424/243 |
| 4,044,126 A | 8/1977 | Cook et al. | 424/243 |
| 4,227,002 A | 10/1980 | Babcock et al. | 548/216 |
| 4,283,390 A | 8/1981 | Koch et al. | 424/122 |
| 4,304,856 A | 12/1981 | Baltz et al. | 435/76 |
| 4,328,245 A | 5/1982 | Yu et al. | 424/305 |
| 4,358,603 A | 11/1982 | Yu | 560/2 |
| 4,364,923 A | 12/1982 | Cook et al. | 424/46 |
| 4,409,239 A | 10/1983 | Yu | 424/305 |
| 4,410,545 A | 10/1983 | Yu et al. | 424/305 |
| 4,414,209 A | 11/1983 | Cook et al. | 424/243 |
| 4,431,809 A | 2/1984 | Hoehn et al. | 546/247 |
| 4,522,811 A | 6/1985 | Eppstein et al. | 514/2 |
| 4,692,443 A | 9/1987 | Katner | 514/206 |
| 4,980,281 A | 12/1990 | Housey | 435/29 |
| 4,985,352 A | 1/1991 | Julius et al. | 435/6 |
| 5,024,939 A | 6/1991 | Gorman | 435/69.1 |
| 5,032,587 A | 7/1991 | DiNinno et al. | 514/210 |
| 5,034,384 A | 7/1991 | Greenlee et al. | 514/210 |
| 5,071,773 A | 12/1991 | Evans et al. | 436/501 |
| 5,077,287 A | 12/1991 | Ternansky | 514/210 |
| 5,128,254 A | 7/1992 | Sibley et al. | 435/172.3 |
| 5,155,218 A | 10/1992 | Weinshank et al. | 536/27 |
| 5,192,742 A | 3/1993 | Coates et al. | 514/8 |
| 5,322,847 A | 6/1994 | Marfat et al. | 514/303 |
| 5,369,028 A | 11/1994 | Harpold et al. | 435/252.3 |
| 5,386,025 A | 1/1995 | Jay et al. | 536/23.5 |
| 5,391,492 A | 2/1995 | Hamill et al. | 435/252.1 |
| 5,401,629 A | 3/1995 | Harpold et al. | 435/6 |
| 5,407,820 A | 4/1995 | Ellis et al. | 435/240.2 |
| 5,429,921 A | 7/1995 | Harpold et al. | 435/4 |
| 5,436,128 A | 7/1995 | Harpold et al. | 435/6 |
| 5,455,238 A | 10/1995 | Aszodi et al. | 514/202 |
| 5,521,297 A | 5/1996 | Daggett et al. | 536/23.5 |
| 5,567,710 A | 10/1996 | Whitten et al. | 514/292 |
| 5,585,388 A | 12/1996 | Cosford et al. | 514/343 |
| 5,587,372 A | 12/1996 | Aszodi et al. | 514/202 |
| 5,594,011 A | 1/1997 | McDonald et al. | 514/343 |
| 5,610,196 A | 3/1997 | Wood | 514/675 |
| 5,618,720 A | 4/1997 | Ellis et al. | 435/323 |
| 5,668,117 A | 9/1997 | Shapiro | 514/55 |
| 5,670,113 A | 9/1997 | Akong et al. | 422/63 |
| 5,712,266 A | 1/1998 | Aszodi et al. | 514/202 |
| 5,877,278 A * | 3/1999 | Zuckermann et al. | 530/334 |

FOREIGN PATENT DOCUMENTS

| | | | |
|---|---|---|---|
| CA | 2085137 | 12/1992 | 5/510 |
| DE | 2143755 | 3/1973 | |
| EP | 0467434 | 6/1991 | 5/477 |
| EP | 0554004 | 1/1993 | 5/501 |
| EP | 0581501 | 7/1993 | 5/477 |
| EP | 0771800 | 10/1996 | 5/491 |
| EP | 0779284 | 6/1997 | 8/295 |
| JP | 62181284 | 8/1987 | 4/519 |
| JP | 01047789 | 2/1989 | 4/501 |
| JP | 01233270 | 9/1989 | 4/207 |
| JP | 09077669 | 3/1997 | 6/31 |
| WO | 9319072 | 9/1992 | 5/519 |
| WO | 9221683 | 12/1992 | |
| WO | 9222556 | 12/1992 | 5/519 |
| WO | 9404822 | 3/1994 | 5/39 |
| WO | 9411388 | 5/1994 | 5/1 |
| WO | 9424284 | 10/1994 | 5/15 |
| WO | 9429449 | 12/1994 | 5/15 |
| WO | 9501976 | 1/1995 | 6/401 |
| WO | 9513299 | 5/1995 | |
| WO | 9528640 | 10/1995 | 6/33 |
| WO | 9530642 | 11/1995 | 6/205 |
| WO | 9600148 | 1/1996 | 6/9 |
| WO | 9602505 | 2/1996 | 6/213 |
| WO | 9603418 | 2/1996 | 6/21 |
| WO | 9603424 | 2/1996 | 6/1 |
| WO | 9605200 | 2/1996 | 6/471 |

(List continued on next page.)

OTHER PUBLICATIONS

BioWorld Today vol. 8, No. 202 (Oct. 17, 1997)—CombiChem Seeks $27M In IPO Signs Agreement With Athena.

(List continued on next page.)

*Primary Examiner*—Jyothsna Venkat
*Assistant Examiner*—Maurie E. Garcia
(74) *Attorney, Agent, or Firm*—Shu Muk Lee; David L. Rose

(57) ABSTRACT

Methods for solid phase and combinatorial synthesis using a resin activation/capture approach are provided. In particular, methods for the production of dihydropyridones, N-acyldihydropyridones, tetrahydropyridones, pyridines, aminopyridines, N-acyltetrahydropyridines and tetrahydropyridines compounds and libraries containing such compounds are provided. Methods for screening the libraries and compounds and pharmaceutical compositions containing compounds prepared by the methods are provided.

24 Claims, No Drawings

FOREIGN PATENT DOCUMENTS

| | | | | |
|---|---|---|---|---|
| WO | 9611930 | 4/1996 | | 6/471 |
| WO | 9615123 | 5/1996 | | 6/401 |
| WO | 9631475 | 10/1996 | | 6/213 |
| WO | 9633972 | 10/1996 | | |
| WO | 9711072 | 3/1997 | | 6/453 |
| WO | 9717970 | 5/1997 | | 6/31 |
| WO | 9719059 | 5/1997 | | |
| WO | 9729111 | 8/1997 | | 6/501 |
| WO | 9735198 | 9/1997 | | 6/33 |

OTHER PUBLICATIONS

BioWorld Today vol. 8, No. 190 (Oct. 1, 1997)—Britstol–Meyers To Pay ICAgen $75M For Heart Drugs.

BioWorld Today vol. 8, No. 158, (Aug. 15, 1997)—Bayer Buys Into GI's DiscoverEease Progragm For Access To Library Of Protein.

BioWorld Today vol. 8, No. 133 (Jul. 11, 1997)—ArQule Could Get $100M In Deal With Wyeth–Ayerst.

BioWorld Today vol. 8, No. 119 (Jun. 20, 1997)—Trega Biosciences, Ono Pharmaceutical Target Inflammatory Diseases In $25M Alliance.

BioWorld Today vol. 8, No. 88 (May 7, 1997)—Roche Tapps Alanex For Combinatorial Expertise.

BioWorld Today vol. 8, No. 83 (Apr. 30, 1997)—Agouron Acquires Alanex For Up To $63M.

Abe et al., Molecular characterization of a novel metabotropic glutamate receptor mGluR5 coupled to inositol phostphate/ca2+ signal transduction, *J. Biol. Chem.* 267:13361–13368 (1992).

Allin et al., The preparation and first application of a polymer–supported "Evans" oxazolidinome, *Tetrahedron Lett.* 37:8023–8026 (1996).

Altenhofen et al., Coontrol of ligand specificity in cyclic nucleotide–gated channels from rod photoreceptors and olfactory epithelium, *Proc. Natl. Acad. Sci. U.S.A.* 88:9868–9872 (1991).

Ansel, Introduction to Pharmaceutical Dosage Forms, Fourth Edition, p. 126 (1985).

Backes et al., Activation method to prepare a highly reactive acylsulfonamide "safety–catch" linker for solid–phase synthesis, *J. Am. Chem. Soc.* 118:3055–1056 (1996).

Beaver et al., Application of the sulfonamide functional group as an anchor for solid phase organic synthesis (SPOS), *Tetrahedron Lett.* 37: 1145 (1996).

Bettler et al., Cloning of a novel glutamate receptor subunit, GluR5: Expression in the nervous system during development, *Neuron* 5:583–595 (1990).

Bettler et al., Cloning of a putative glutamate receptor: a low affinity kainate–binding subunit, *Neuron* 8:257–265 (1992).

Bhargava et al., Synthesis of a cyclic analogue of oxidized glutahione by an intersite reaction in a swollen polymer network, *J. Am. Chem. Soc.* 105: 3247–3251 (1983).

Bolton,Solid Phase Synthesis of Azabicyclo [4,3,)] nonen–8–one Amino Acid Derivatives via Intramolecular Pauson–Khand Cyclization *Tetrahedron Lett.* 37: 3433 (1996).

Bonner et al., Cloning and expression of human and rat m5 muscarinic acetylcholine receptor genes, *Neuron* 1:403–410 (1988).

Boulter et al., Molecular clonning and functional expression of glutamate receptor subunit genes, *Science* 249:1033–1037 (1990).

Boulter et al., $\alpha 3$, $\alpha 5$, and $\beta 4$: three members of the rat neuronal nicotinic actylcholine receptor–related gene family form a gene cluster, *J. Biol. Chem.* 265:4472–4482 (1990).

Boulter et al., Isolation of a cDNA clone coding for a possible neural nicotinic acetylcholine receptor $\alpha$–subunit, *Nature* 319:368 (1986).

Bray et al., Direct cleavage of peptides from a solid support into acqueous buffer. Applications in simultaneous multiple peptide synthesis, *J. Org. Chem.* 56: 6659–66666 (1991).

Brown et al., A single–bead decode strategy using electrospray ionization mass spectrometry and a new phtolabile linker: 3–amino–3–(2–nitrophenylpropionic acid, *Mol. Divers.* 1: 4–12 (1995).

Brown, Recent Developments in solid–phase organic synthesis, *Contemp. Org. Synth.* 4: 216–237 (1997).

Buckman et al. Solid–Phase Synthesis of 1,3–Dialkyl Quinazoline–2,4–Diones *Tetrahedron Lett.* 1996, 37, 4439.

Burgess et al., An approach to photoliable, fluorescent protecting groups, *J. Org. CHem.* 62: 5165–5168 (1997).

Cardno et al., A simple multiple release system for combinatorial library and peptide analysis, *Tetrahedron Lett.* 37:135–138 (1996).

Chaiken et al., Molecular Diversity and Combinatorial Chemistry: Libraries and Drug Discovery, 58 p. (American Chemical Society: Washington, D.C.) (1996).

Chan et al., Reductive alkylation of 9–amino–xanthene–3–yloxymethylpoly(styrene): a novel procedure for the synthesis of peptidyl N–alkyl amides by Fmoc/Bu$^t$ chemistry, *J. Chem. Soc. Chem. Commun.*: 1475–1476 (1995).

Chini et al., Neuronal–type $\alpha$–bungarotoxin receptors and the $\alpha_5$–nicotinic receptor subunit gene are expressed in neuronal and nonneuronal human cell lines *Proc. Natl. Acad. ASci. U.S.A.* 89:1572–1576 (1992).

Comins et al., Synthesis of 2,4–disubstituted N–acyl–5, 6–dihydro–2–pyridones, *Tetrahedron Lett.* 37: 9275–9278 (1996).

Comins et al., Enantiopure N–acyldihydropyridones as synthetic intermediates: the first asymmetric synthesis of trans–decahydroquinoline alkaloid (+)–219A, *J. Org. CHem.* 60, 794–795 (1995).

Comins et al., Asymmetric synthesis of 2–alkyl9aryl)–2, 3–dihydro–4–pyridones by addition of Grignard reagents to chiral 1–acyl–4–methoxypyridinium salts, *J. Am. Chem. Soc.* 116: 4719–4728 (1994).

Comins et al., Efficient synthesis and resolution of trans–2–(1–aryl–1–methylethyl)cyclohexanols: practical alternatives to 8–phenylmenthol, *J. Org. Chem.* 58: 4656–4661 (1993).

Comins et al., N–acyldihydropyridones as synthetic intermediates. A short synthesis of (+)–pumiliotoxin C, *Tetrahedron Lett.* 32: 5697–5700 (1991).

Comins et al., Regioselective addition of Grignard reagents to 1–acylpyridinium salts. A convenient method fo rthe synthesis of 4–alkyl(aryl)pyridines, *J. Org. Chem.* 47: 4315–4319 (1982).

D'Amour et al., A method for determining loss of pain sensation, *J. Pharmacol. Exp. Ther.* 72:74–79 (1941).

Dascal, The use of *Xenopus oocytes* for the study of ion channels *CRC Crit. Rev. Biochem.* 22:317 (1987).

DeGrado et al., Polymer–bound oxime esters as supports for solid–phase peptide synthesis. preparation of protected peptide fragments, *J. Org. Chem.* 45: 1295–1300 (1980).

Deneris et al., Primary structure and expression of β2: a novel subunit of neuronal nicotinic acetylcholine receptors, *Neuron 1*:45–54 (1988).

Deneris et al., β$_3$ : a new member of nicotinic acetylcholine receptor gene family is expressed in brain, *J. Biol. Chem. 264*:6268–6272 (1989).

Dhallan et al., Primary structure and functional expression of a cyclic nucleotide–activated channel from olfactory neurons, *Nature 347*:184–187 (1990).

Dressman et al., Solid Phase Synthesis of Hydantoins Using a Carbamate Linker and a Novel Cyclization/Cleavage Step *Tetrahedron Lett. 37*: 937 (1996).

Duvoisin et al., The functional diversity of the neuronal nicotinic acetylcholine receptors is increased by a novel subunit: β4 *Neuron 3*:487–496 (1989).

Edwards et al., Inhibition of myeloperoxidase release from rat polymorphonuclear leukocytes by a series of azachalcone derivatives, *J. Med. Chem. 37*: 4357–4362 (1994).

Egebjerg et al., Cloning of cDNA for a glutamate receptor subunit activated by kainate but not AMPA, *Nature 351*:745–748 (1991).

Ellman, Design, synthesis, and evaluation of small–molecule libraries, *Acc. Chem. Res. 29*:132 (1996).

Emerich et al., Nicotine potentiates haloperidol–induced catalepsy and locomoter hypoactivity, *Pharmacol, Biochem, Behav.38*:875–880 (1991).

Entwistle et al., The Use of 2–Nitrophenylpropionic Acid as a Protecting Group for Amino and Hydroxyl Functions to be Recovered by Hydrogen Transfer Reduction *Tetrahedron Lett.*:555–558 (1979).

Flynn et al., Characterization of L–[$^3$H]Nicotine binding in human cerebral cortex: comparison between Alzheimer's disease and the normal, *J. Neurochem. 47*:1948 (1986).

Frechet et al., Use of polymers as protecting gropus in organic synthesis, III. Selective functionalization of polyhydroxy alcohols, *Can. J. Chem. 54*:926–934 (1976).

Frielle et al., Cloning of the cDNA for the human β$_1$–adrenergic receptor, *Proc. Natl. Acad. Sci. 84*:7920–7924 (1987).

Gallop et al., Applications of combinatorial technologies to drug discovery. 1. Background and peptide combinatorial libraries, *J. Medicinal Chemistry 37*:1233–1251 (1994).

Gayo et al., Traceless linker: oxidative activation and displacement of a sulfur–based linker, *Tetrahedron Lett. 38*: 211–214 (1997).

GenBank accession #M16404.

GenBank accession #M16405.

GenBank accession #M16407.

Goff et al., The synthesis of 2–oxopiperazines by intramolecular Michael addition on solid support, *Tetrahedron Lett. 37*: 6247 (1996).

Goldman et al., Members of a nicotinic acetylcholine receptor gene family are expressed in different regions of the mammalian central nervous system, *Cell 48*:965–973 (1987).

Goulet et al., Continuous or pulsatile chroonic D$_2$ dopamine receptor agonist (U91356A) treatment of drug–naive 4–phenyl–1,2,3,6–tetrahydropyridine monkeys differentially regulates brain D$_1$ and D$_2$ receptor expression: in situ hybridization histochemical analysis, *Neuroscience 79*: 497–507 (1997).

Hamill et al., Improved patch–clamp techniques for high–resolution current recording from cells and cell–free membrane patches, *Pflugers Arch. 391*:85–100 (1981).

Han et al., Silicon Directed ipso–Substitution of Polymer Bound Arylsilanes: Preparation of Biaryls via the Suzuki Cross–Coupling Reaction *Tetrahedron Lett. 37*: 2703–2706 (1996).

Hanessian et al., Solution and Solid Phase Synthesis of 5–Alkoxyhydantoin Libraries with a Three–Fold Functional Diversity *Tetrahedron Lett. 37*: 5835 (1996).

Hess et al., Different modes of ca channel gating behaviour favoured by dihydropyridine Ca agonists and antagonists, *Nature 311*:538–544 (1984).

Hollman et al., Cloning by functional expression of a member of the glutamate receptor family, *Nature 342*:643–648 (1989).

Hosang et al. Highly Efficient Enzymatic Resolution of Homoallyl Alcohols Leading to a Simple Synthesis of Optically Pure Fluoxetine and Related Compounds, *Tetrahedron Lett. 37*:9253–9254 (1996).

Houamed et al., Cloning, expression, and gene structure of a G protein–coupled glutamate receptor from rat brain, *Science 252*:1318–1321 (1991).

Hutchins et al., Fischer Indole Synthesis on a Solid Support *Tetrahedron Lett. 37*: 4869 (1996).

IUPAC–IUB Commission on Biochemical Nomenclature— Symbols for amino–acid derivatives and peptides recommendations (1971), *Biochem. 11*: 1726 (1972).

Johnson et al., Expression and structure of the human NGF receptor, *Cell 47*:545–554 (1986).

Jones et al., Characterization of the binding of radioligands to N–methyl–D–aspartate, phenyclidine, and glycine receptors in buffy coat membranes, *J. Pharmacol. Meth. 21*:161 (1989).

Julius et al., The 5HT2 receptor defines a family of structurally distinct but functionally conserved serotonin receptors, *Proc. Natl. Acad. Sci. USA 87*:928–932 (1990).

Julius et al., Molecular characterization of a functional cDNA encoding rthe serotonin 1 c receptor, *Science 241*:558–564 (1988).

Kaoldor et al., Use of SOlid Supported Nucleophiles and Electrophiles for the Purification of Non–Peptide Small Molecule Libraries *Tetrahedron Lett. 37*: 7193–7196 (1996).

Kayano et al., Primary structure of rat brain sodium channel III deduced from cDNA sequence, *FEBS Lett. 228*:187–194 (1988).

Khan et al., Solid Phase Reductive Alkylation of Secondary Amines *Tetrahedron Lett. 37*: 4819–4822 (1996).

Keinanen et al., A family of AMPA–selective glutamate receptors, *Science 294*:556–560 (1990).

Kobayashi et al., Polymer–Supported SilylEnol Ethers. Synthesis and Reactions with Imines for the Preparationof an Amino Alcohol Library *Tetrahedron Lett. 37*:2809–2812 (1996).

Kobilka et al., Cloning, sequencing, and expression of the gene coding for the human platelet α$_2$–adrenergic receptor, *Science 238*:650–656 (1987).

Kobilka et al., An intronless gene encoding a potential member of the family of receptors coupled to guanine nucleotide regulatory proteins, *Nature 329*:75–79 (1987).

Koh et al., Palladium–mediated three–component coupling strategy for the solid–phase synthesis of tropane derivatives, *J. Org. Chem. 61*: 4494 (1996).

Krchnak et al., Structurally homogeneous and heterogeneous synthetic combinatorial libraries, *Mol. Divers 1*: 149–164 (1995).

Levitan et al., Structural and functional basis for GABA$_A$ receptor heterogeneity, *Nature* 335:76–79.

Ley et al., Solid–phase synthesis of bicyclo[2.2.2]octane derivatives via tandem Michael addition reactions and subsequent reductive animation, *Synlett.*: 1017 (1995).

Leznoff et al., The use of polymer supports in organic synthesis. The synthesis of monotrityl ethers of symmetrical diols, *Can. J. Chem.* 50: 2892–2893 (1972).

Lloyd–Williams et al., Convergent Solid–Phase Peptide Synthesis *Tetrahedron* 49: 11065–11133 (1993).

Lorsbach et al., Reissert–based "traceless" solid–phase synthesis: isoquinoline, and isoxazoline–containing heterocyles, *J. Org. Chem.* 61: 8716–8717 (1996).

Lyle et al., The reaction of 1–acylpyridinium salts with Grignard and organocadmium reagents, *Tetrahedron Lett.* 12: 1015–1018 (1977).

MacDonald et al.,A Solid Phase Approach to Quinlones using the DIVERSOMER Technology, *Tetrahedron Lett.* 37: 4815–1818 (1996).

Maeji et al., Multi–pin peptide synthesis strategy for T–cell determinant analysis, *J. Immunol. Meth.* 134: 23–33 (1990).

Marquais et al., Aryl–aryl cross coupling on a Solid Support Using Zinc Organic Reagents and Palladium Catalysis, *Tetrahedron Lett.* 37: 5491–5494 ()996).

McKinnon, Isolation of a cDNA clone for a putative second potassium channel indicates the existence of a gene family, *J. Biol. Chem.* 264:9230–8236 (1989).

Meguro et al., Functional characterization of a heterometric NMDA receptor channel expressed from cDNAs, *Nature* 357:70–74 (1992).

Merrifield, Solid–phase peptide synthesis. III. An improved synthesis of bradykinin, *Biochemistry* 3:1385–1390 (1964).

Marzinzik et al., Solid Support Synthesis of Highly Functionalize Pyrazoles and Isoxazoles; Scaffolds for Molecular Diversity, *Tetrahedron Lett.* 37: 1003–1006 (1996).

Meutermans et al., The Solid phase synthesis of dihydro– and tetrahydroisoquinolines, *Tetrahedron Lett.* 36: 7709–7712 (1995).

Mjalli et al., Solid phase synthesis of pyrroles derived from a four componen condensation, *Tetrahedron Lett.* 37:2943–2946 (1996).

Monyer et al., Heteromeric NMDA receptors: molecular and fiunctional distinction of subtypes, *Science* 256:1217–1221 (1992).

Moriyoshi et al., Molecular cloning and characterization of the rat NMDA receptor, *Nature* 354:31–37 (1991).

Morphy et al., A Novel Linker Strategyn for Solid–Phase Synthesis *Tetrahedron Lett.* 37: 3209–3212 (1996).

Newlander et al., Simple silyl linker for the solid phase organic synthesis of aryl–containing molecules, *J. Org. Chem.* 62: 6726–6732 (1997).

Ni et al., Versatile approach to encoding combinatorial organic synthesis using chemically robust secondary amine tags, *J. Med. Chem.* 39: 1601 (1996).

Noda et al., Existence of distinct sodium channel messenger RNAs in rat brain, *Nature* 320:188–192 (1986).

O'Neill et al., Evidence for an involvement of D1 and D2 dopamine receptors in mediating nicotine–induced hyperactivity in rats, *Psychopharmacology* 104:343–350 (1991).

Otsuka et al., Novel zinc chelators which inhibit the binding of HIV–EP1 (HIV enhancer binding protein) to NF–κB recognition, *J. Med. Chem.* 37: 4267–4269 (1994).

Patek et al.,Safety–Catch Anchoring Linkage for Synthesis of Peptide Amides by Boc/Fmoc Strategy *Tetrahedron Lett.* 32: 3891–3894 (1991).

Patel et al., Applications of small–molecule combinatorial chemistry to drug discovery, *Drug Disc. Today* 1: 134–144 (1996).

Paulmichl et al., New mammalian chloride channel idenetified by expression cloning, *Nature* 356:238–241 (1992).

Plunkett et al., A silicon–based linker for traceless solid–phase synthesis, *J. Org. Chem.* 60: 6006–6007 (1995).

Randolph et al., Major simplifications in oligosaccharide syntheses arising from solid–phase based method: an application to the synthesis of the Lewis b antigen, *J. Am. Chem. Soc.* 117: 5712–5719 (1995).

Reggelin et al., Towards Polyketide Libraries: Iterative, Asymmetric Aldol Reactions on a Solid Support, *Tetrahedron Lett.* 37: 6851 (1996).

Ruhland et al., Solid–supported combinatorial synthesis of structurally diverse–β–lactams, *J. Am. Chem. Soc.* 118: 253–251 (1996).

Ruhland et al., Structurally diverse 2,6–disubstituted quinoline derivatives by solid–phase synthesis, *Tetrahedron Lett.* 37: 2757 (1996).

Ruth et al., Primary structure of the β subunit of the DHP–sensitive calcium channel from skeletal muscle, *Science* 245:1115–1118 (1989).

Sacaan et al., Metabotropic glutamate receptor activation produces extrapyramidal motor system activation that is mediated by striatal dopamine, *J. Neurochem.* 59:245 (1992.

Salmon et al., Discovery of biologically active peptides in random libraries: solution–phase testing after staged orthogonal release from resin beads, *Proc. Natl. Acad. Sci. U.S.A.* 90: 11708–11712 (1993).

Sarshar et al., Imidazole libraries on solid support, *Tetrahedron Lett.* 37: 835 (1996).

Schoepp et al., 1S,3R–ACPD–sensitive (metabotropic) [$^3$H] glutamate receptor binding in membranes, *Neurosci. Lett.* 145:100 (1992).

Schofield et al., Sequence and functional expression of the GABA$_A$ receptor shows a ligand–gated receptor super–family, (1987) *Nature* 328:221–227.

Shivers et al., Two novel GABA$_A$ receptor subunits exist in distinct neuronal subpopulations, *Neuron* 3:327–337 (1989).

Sills et al., [$^3$H]CGP 39653: a new N–methyl–D–aspartate antagonist radioligand with low nanomolar affinity in rat brain, *Eur. J. Pharmacol.* 192:19 (1991).

Smith et al., An efficient solid phase synthetic route to 1,3–disubstituted 2,4(1H,3H)–quinazolinediones stuitable for combinatorial sythesis, *Bioorg. Med. Chem. Lett.* 6: 1483–1486 (1996).

Stillman et al., Replication and supercoiling of simian virus 40 DNA in cell extracts from human cells, *Mol. Cell. Biol.* 5:2051–2060 (1985).

Stormann et al., Molecular cloning and expression of a dopamine D$_2$ receptor from human retina, *Molec. Pharm.* 37:1–6 (1990).

Stuhmer, Electrophysiological recording from *Xenopus* oocytes, *Meth. Enzymol.* 207:319–339 (1992).

Sugihara et al., Structures and properties of seven isoforms of the NMDA receptor generated by alternative splicing, *Biochem. Biophys. Res. Comm.* 185:826–832 (1992).

Tanabe et al., A family of metabotropic glutamate receptors, *Neuron* 8:169–179 (1992).

Tanabe et al., Primary structure of the receptor for calcium channel blockers from skeletal muscle, *Nature* 328:313–318 (1987).

Tempel et al., Cloning of a probable potassium gene from mouse brain, *Nature* 332:837–839 (1988).

Thiemann et al., A chloride channel widely expressed in epithelial and non–epithelial cells, *Nature* 356:57–60 (1992).

Tietze et al., Stereoselective solid–phase synthesis of cylcopentane and cyclohexane derivatives by two–compnent domino reactions: generation of combinatorial libraries, *Angew. Chem., Int. Ed. Eng. 35*: 651 (1996).

Tietze et al., A general and expedient method for the solid–phase synthesis of structurally diverse 1–phenyl–pyrazalone derivatives, *Synlett*: 667–8 (1996).

Ungerstedt et al., Quantitative recording of rotational behavior in rats after 6–hydroxy–dopamine lesions of the nigrostriatal dopamine system, *Brain Res.* 24:485–493 (1970).

Van Maarseveen et al., Solid phase ring–closing methatesis: cyclization/cleavage approach towards a seven membered cylcoolefin, *Tetrahedron Lett. 37*: 8249–8252 (1996).

Wada et al., Functional expression of a new pharmacological subtype of brain nicotinic acetylcholine receptor, *Science* 240: 330–334 (1988).

Wang et al., Solid phase synthesis of 2,3–dihydro–4–pyridones: reaction of Danishefsky's diene with polymer–bound imines, *Abstracts of the 214th American Chemical Society National Meeting*, ORGN 285 (1997).

Westhead, Semiautomated turbidometric bioassay for the ionophore A23187, *Antimicrobial Agents and Chemotherapy 11* (5):916–918 (1977).

Wipf et al., A Solid phase protocol of the Bignelli dihydropyrimidine synthesis suitable for combinatorial chemistry, *Tetrahedron Lett. 36*: 7819 (1995).

Wong et al., The anticonvulsant NK–801 is a potent N–methyl–D–aspartate antagonist, *Proc. Natl. Acad. Sci. USA 83*:7104 (1986).

Worster et al., Asymmetric synthesis of 2–alkylcyclohexanones on solid phases[**], *Angew. Chem. Int. Ed. Eng. 18*: 221–222 (1979).

Yang et al., Pictet–Spengler reaction on solid support, *Tetrahedron Lett. 37*: 5041 (1996).

Ymer et al., GABAA receptor β subunit heterogeneity: functional expression of cloned cDNAs *EMBO J.* 8:1665–1670 (1989).

Zaragoza, Solid–phase synthesis of substituted 3–aminotheiophenes and 2–methylene–2,3–dihydrothiazoles, *Tetrahedron Lett. 37*: 6213 (1996).

Zaragoza et al., Generation of rhodium carbenoids on a polystyrene support and their OH–insertion reaction with alcohols, *Tetrahedron 52*: 5999 (1996).

Zaragoza, Carbon–carbon bond formation on solid support: synthesis of monoacyl piperazines by Knoevenagel–type condensation reactions, *Tetrahedron Lett. 36*: 8677 (1995).

Zaragoza et al., Solid–phase synthesis of substituted 1,2, 3–triazoles, *Tetrahedron 52*: 10823 (1996).

Zhang et al., Synthesis of tetrasubstituted imidazoles via α–(N–acyl–N–alkylamino)–β–ketoamides on Wang resin, *Tetrahedron Lett. 37*: 751 (1996).

Dialog abstract 011343924, citing EP 779284 A.

Dialog abstract 000938738, citing DE 2143755 A.

Dialog abstract 007837259, citing JP 1047789 A.

Dialog abstract 008049022, citing JP 1233270 A.

Dialog abstract 007263932, citing JP 62181284 A.

Dialog abstract 009627117, citing WO 9319072.

Dialog abstract 010608862, citing WO 9602505.

Dialog abstract 011311142, citing WO 9717970 A.

* cited by examiner

SOLID PHASE SYNTHESIS OF HETEROCYCLES

FIELD OF THE INVENTION

The present invention relates to methods of creating libraries of compounds using combinatorial synthesis. In particular, the provides methods for synthesizing compounds using a resin activation/capture approach (REACAP technology). The method is amenable to adaptation for use in combinatorial synthetic schemes. Libraries, compounds and pharmaceutical compositions containing compounds produced by the methods are also contemplated herein.

BACKGROUND OF THE INVENTION

Solid phase and combinatorial methods

Solid phase and combinatorial chemistry are very important in the production and screening of collections or "libraries" of compounds. These libraries are of increasing importance in medicinal chemistry and the discovery of new therapeutic agents. See, generally, Backes et al. *Current Opinion in Chem. Biol.* 1997, 1, 86–93. Although these synthetic methods were initially developed for the generation of peptides and oligonucleotides, focus has recently shifted to the area of small molecule synthesis, due to the improved pharmacokinetics of such compounds and the greater potential of small molecules as therapeutic agents.

Generally, the methods used in solid phase and combinatorial chemistry involve immobilizing or capturing the substrate to be modified on a resin or other solid support. Immobilization has the advantage over solution phase chemistry in that purification of the modified substrate is greatly simplified. Additionally, the use of multiple solid supports (e.g., pins, beads, etc.) in a combinatorial approach allows for the production of a large number of diverse compounds, i.e., libraries, in a single operation. See, generally, Chaiken et al. *Molecular Diversity and Combinatorial Chemistry: Libraries and Drug Discovery* 1996, 328 pp. (American Chemical Society: Washington, D.C.). The immobilization or capture of the substrate is usually, but not always, accomplished by covalent attachment of the substrate to the resin or other solid support through a linker.

Linkers are chosen such that the substrate is easily and efficiently immobilized and, following modification, cleaved from the resin or other solid support to provide the libraries and compounds of interest. Linkers which have been reported for use in solid phase and combinatorial synthesis include linkers based on protecting groups used in solution phase synthesis (see, e.g., Leznoff et al. *Can. J. Chem.* 1972, 50, 2892–2893; Frechet et al. *Can. J. Chem.* 1976, 54, 926–934; Chan et al. *J. Chem. Soc., Chem. Commun.* 1995, 1475–1476; Krchnak et al. *Mol. Divers.* 1995, 1, 149–164; Burgess et al. *J. Org. Chem.* 1997, 62, 5165–5168), "traceless" linkers (see, e.g., Plunket et al. *J. Org. Chem.* 1995, 60, 6006–6007; Han et al. *Tetrahedron Lett.* 1996, 37, 2703–2706; Lorsbach et al. *J. Org. Chem.* 1996, 61, 8716–8717; Newlander et al. *J. Org. Chem.* 1997, 62, 6726–6732), support-bound chiral auxiliaries (see, e.g., Worster et al. *Angew. Chem. Int. Ed. Eng.* 1979, 18, 221–222; Allin et al. *Tetrahedron Lett.* 1996, 37, 8023–8026), photolabile linkers (see, e.g., Lloyd-Williams et al. *Tetrahedron* 1993, 49, 11065–11133; Brown et al. *Mol. Divers.* 1995, 1, 4–12), linkers devised to assist in deconvolution of combinatorial libraries (see, e.g., Salmon et al. *Proc. Natl. Acad. Sci. U.S.A.* 1993, 90, 11708–11712; Cardno et al. *Tetrahedron Lett.* 1996, 37, 135–138), diversification linkers (see, e.g., Kaldor et al. *Tetrahedron Lett.* 1996, 37, 7193–7196; DeGrado et al. *J. Org. Chem.* 1980, 45, 1295–1300), "safety-catch" linkers (see, e.g., Backes et al. *J. Am. Chem. Soc.* 1996, 118, 3055–3056; Gayo et al. *Tetrahedron Lett.* 1997, 38, 211–214; Morphy et al. *Tetrahedron Lett.* 1996, 37, 3209–3212, Patek et al. *Tetrahedron Lett.* 1991, 32, 3891–3894) and linkers which allow for release of the substrate from the resin or other solid support by cyclization onto the support attachment site (see, e.g., Bhargava et al. *J. Am. Chem. Soc.* 1983, 105, 3247–3251; Van Maarseveen et al. *Tetrahedron Lett.* 1996, 37, 8249–8252; Entwistle et al. *Tetrahedron Lett.* 1979, 555–558; Maeji et al. *J. Immunol. Meth.* 1990, 134, 23–33; Bray et al. *J. Org. Chem.* 1991, 56, 6659–6666). While the use of linkers is a common method, linkers are not required for combinatorial synthesis and, in certain instances, are not preferred due to added complexity in the combinatorial method.

In known solid phase and combinatorial methods, the immobilization or capture of the substrate on the resin generally does not modify the reactivity of the substrate. This has the advantage of allowing the use of known organic chemistry in a predictable fashion for producing libraries and compounds of interest. Chemical methods which have been used successfully in solid phase or combinatorial chemistry include aldol condensations (Ruhland et al. *Tetrahedron Lett.* 1996, 37, 2757), including asymmetric aldol reactions (Reggelin et al. *Tetrahedron Lett.* 1996, 37, 6851), Knovenagel-type condensations (Zaragoza *Tetrahedron Lett.* 1996, 37, 6213), sequential Knoevenagel and Hantzsch condensations (Gordeev et al. *Tetrahedron Lett.* 1996, 37, 2809), Claisen condensations (Marzinzik et al. *Tetrahedron Lett.* 1996, 37, 1003), tandem Michael addition reactions (Ley et al. *Synlett.* 1995, 1017), Staudinger cycloadditions (Ruhland et al. *J. Am. Chem. Soc.* 1996, 118, 253), 1,3-dipolar cyloadditions (Mjalli et al. *Tetrahedron Lett.* 1996, 37, 2943), Diels-Alder reactions (International Patent Publication Number WO 96/03424), including hetero-Diels-Alder reactions (International Patent Publication Number WO 95/28640), intramolecular ene reactions (Tietze et al. *Angew. Chem., Int. Ed. Eng.* 1996, 35, 651), Fischer indole syntheses (Hutchins et al. *Tetrahedron Lett.* 1996, 37, 4869), electrophilic aromatic substitutions (Yang et al. *Tetrahedron Lett.* 1996, 37, 5041), Bischler-Napieralski reactions (Meutermans et al. *Tetrahedron Lett.* 1995, 36, 7709), Suzuki, Stille, Heck and Sonogashira palladium-catalyzed coupling reactions (Koh et al. *J. Org. Chem.* 1996, 61, 4494; Beaver et al. *Tetrahedron Lett.* 1996, 37, 1145), Pauson-Khand cyclizations (Bolton *Tetrahedron Lett.* 1996, 37, 3433), Ugi reactions (Zhang et al. *Tetrahedron Lett.* 1996, 37, 751), Horner-Wadsworth-Emmons olefinations (Johnson et al. *Tetrahedron Lett.* 1996, 37, 9253), reductive alkylations of amines with carbonyl compounds (Khan et al. *Tetrahedron Lett.* 1996, 37, 4819), Reissert condensation/alkylation (Lorsbach et al. *J. Org. Chem.,* 1996, 61, 8716), Mitsunobu reactions (Patel et al. *Drug Disc. Today* 1996, 1, 134), oxymercurations (International Patent Publication Number WO 96/03418) and rhodium carbenoid reactions (Zaragoza et al. *Tetrahedron* 1996, 52, 5999).

The disadvantage of this type of immobilization or capture is that a substrate may need to be activated in a subsequent step in order to afford the requisite activity with a reagent of interest. For example, a pyridine must be activated by reaction with, e.g., a chloroformate to allow for reaction of the resulting N-acylpyridinium ion with a Grignard reagent. In the absence of such activation, a pyridine will generally be unreactive toward this type of reagent.

Libraries and pharmaceutical compositions

Libraries of compounds produced by combinatorial methods are a powerful tool in the discovery of new therapeutic agents. Such libraries, which are designed to provide diverse mixtures of compounds, allow for, in combination with high throughput screening, the rapid screening of a large number of a variety of compounds based on a common scaffold or pharmacophore. This diversity is a valuable feature of the libraries. For example, libraries are recognized to have commercial value through the sales or licensing of the libraries. See, e.g., "CombiChem Seeks $27M In IPO; Signs Agreement With Athena" in *BioWorld Today* vol. 8, no. 202 (Oct. 17, 1997); "Bristol-Meyers To Pay ICAgen $75M For Heart Drugs" in *BioWorld Today* vol. 8, no. 190 (Oct. 1, 1997); "Bayer Buys Into GI's DiscoverEase Program For Access To Library Of Proteins" in *BioWorld Today* vol. 8, no. 158, (Aug. 15, 1997); "Sumitomo To Pay CombiChem $17M To Generate Drug Leads" in *BioWorld Today* vol. 8, no. 150 (Aug. 5, 1997); "Synaptic In $34M Pact With Warner-Lambert For Two Drugs" in *BioWorld Today* vol. 8, no. 150 (Aug. 5, 1997); "ArQule Could Get $100M In Deal With Wyeth-Ayerst" in *BioWorld Today* vol. 8, no. 133 (Jul. 11, 1997); "Trega Biosciences, Ono Pharmacetucal Target Inflammatory Diseases In $25M Alliance" in *BioWorld Today* vol. 8, no. 119 (Jun. 20, 1997); "Roche Taps Alanex For Combinatorial Expertise" in *BioWorld Today* vol. 8, no. 88 (May 7, 1997); and "Agouron Acquires Alanex For Up To $63M" in *BioWorld Today* vol. 8, no. 83 (Apr. 30, 1997). The libraries, which can contain as many as a million or more individual compounds, in combination with high throughput screening, have drastically reduced the time required for the testing of a collection of compounds in biological assays, thereby reducing the time required to discover new therapeutic agents. Therefore, diverse libraries of compounds based on unique scaffolds or pharmacophores are needed to enhance and permit the discovery of new therapeutic agents.

Libraries based on a wide variety of pharmacophores or scaffolds have been reported (see, generally, Brown *Contemp. Org. Synth.* 1997, 4, 216–237). In particular, libraries of 2,6-disubstituted quinolines (Ruhland et al. *Tetrahedron Lett.* 1996, 37, 2757), dihydrobenzopyrans (International Patent Publication Number 9530642), polyketides (Reggelin et al. *Tetrahedron Lett.* 1996, 37, 6851), dihydropyridines (Gordeev et al. *Tetrahedron Lett.* 1996, 37, 2809), quinolones (MacDonald et al. *Tetrahedron Lett.* 1996, 37, 4815), monoacyl piperazines (Zaragoza *Tetrahedron Lett.* 1995, 36, 8677), dihydropyrimidines (Wipf et al. *Tetrahedron Lett.* 1995, 36, 7819), 1-phenylpyrazolones (Tietze et al. *Synlett* 1996, 667), β-lactams (Ni et al. *J. Med. Chem.* 1996, 39, 1601), pyrrolidines (U.S. Pat. No. 5,525,734), indoles (Hutchins et al. *Tetrahedron Lett.* 1996, 37, 4869), tetrahydroisoquinolines and tetrahydroimidazopyridines (Hutchins et al. *Tetrahedron Lett.* 1996, 37, 4865), dihydroisoquinolines (Meutermans et al. *Tetrahedron Lett.* 1995, 36, 7709), biaryls (Marquais et al. *Tetrahedron Lett.* 1996, 37, 5491), tropanes (Koh et al. *J. Org. Chem.* 1996, 61, 4494), thiazolidin-4-ones and thiazinan-4-ones (International Patent Publication Number WO 96/000148), imidazoles (Sarshar et al. *Tetrahedron Lett.* 1996, 37, 835), 1,2,3-triazoles (Zaragoza et al. *Tetrahedron* 1996, 52, 10823), 2-oxopiperazines (Goff et al. *Tetrahedron Lett.* 1996, 37, 6247), benzodiazepines (Ellman *Acc. Chem. Res.* 1996, 29, 132), quinazolinediones (Buckman et al. *Tetrahedron Lett.* 1996, 37, 4439), hydantoins (Dressman et al. *Tetrahedron Lett.* 1996, 37, 937), alkoxyhydantions (Hanessian et al. *Tetrahedron Lett.* 1996, 37, 5835), quinazoline-2,4-diones (Smith et al. *Bioorg. Med. Chem. Lett.* 1996, 6, 1483), isoxazolinylisoquinolines (Lorsbach et al. *J. Org. Chem.* 1996, 61, 8716), pyridines, pyrimidines, 1,4-dihydro derivatives thereof, and piperidines (International Patent Publication No. WO 96/33972) and many others have been constructed.

To date, however, solid phase or combinatorial syntheses of diverse libraries of dihydropyridones, N-acyidihydropyridones, tetrahydropyridones, pyridines, aminopyridines, N-acyltetrahydropyridines and tetrahydropyridines have not been reported, with two exceptions (Wang et al. *Abstracts of the 214th American Chemical Society National Meeting,* ORGN 285 (1997), solid phase synthesis of 2,3-dihydro-4-pyridones; and International Patent Publication No. WO 96/33972, combinatorial synthesis of libraries of pyridines). These libraries possess unique scaffolds for combinatorial synthesis that would otherwise be difficult or impossible to prepare by known methods.

Certain compounds of these classes have previously been prepared using standard solution phase techniques. See, Comins et al. *Tetrahedron Lett.* 1996, 37, 9275–9278; Comins et al. *J. Org. Chem.* 1995, 60, 794–795; Comins et al. *J. Am. Chem. Soc.* 1994, 116, 4719–4728; Comins et al. *Tetrahedron Lett.* 1993, 58, 4656–4661; Comins et al. *Tetrahedron Lett.* 1991, 32, 5697–5700; Comins et al. *Tetrahedron Lett.* 1982, 47, 4315–4319; and Lyle et al. *Tetrahedron Lett.* 1977, 1015–1018. Such compounds, particularly N-acyldihydropyridones, have been shown to be useful as intermediates in the synthesis of alkaloid natural products, such as porantheridine, sedamine, solenopsin, pumiliotoxin, elaeokanines and lasubine.

For example, dihydropyridones have been reported as being useful in the treatment of heart insufficiency (Ger. Offen. DE 3,433,953). Tetrahydropyridones are known as solvents in the production of mixed polyamides (Ger. Offen. DE 2,143,755). Pyridines are known to be inhibitors of the release of myeloperoxidase from polymorphonuclear leukocytes which is believed to influence the tissue destructive nature of adult respiratory distress syndrome (Edwards et al. *J. Med. Chem.* 1994, 37, 4357–4362).

In addition, pyridines are known to possess zinc chelating properties which inhibit the binding of HIV-EP1 to an NF-B recognition sequence (Otsuka et al. *J. Med. Chem.* 1994, 37, 4267–4269). Further indications for pyridine derivatives include use as dopamine agonists in treatment of schizophrenia, Parkinson's disease, Tourette's syndrome, drug addiction and hyperprolactinemia (European Patent Application Publication No. EP 771800) and for treatment of diseases of the central nervous system related to malfunctioning of the nicotinic cholinergic system, such as Alzheimer's disease, disorders of extrapyramidal motor function, such as Parkinson's disease, progressive supramuscular palsy, Huntington's disease, Gilles de la Tourette syndrome and tardive dyskinesia, obesity, severe pain, drug and tobacco withdrawal, respiration, mood and emotional disorders such as depression, anxiety and psychosis, motor control and function, focus and attention disorders, concentration disorders, memory loss, cognitive impairment, dementia (including AIDS dementia), neurodegenerative disorders, epilepsy, cardiovascular dysfunction including hypertension and cardiac arrhythmias, convulsive disorders, eating disorders, including bulimia and anorexia, autonomic disorders including dysfunction of gastrointestinal motility and function such as inflammatory bowel disease, irritable bowel syndrome, diarrhea, constipation, gastric acid secretion and ulcers, comedication in surgical procedures and pheochromocytoma (International Patent Publication Nos. WO 97/11072, WO 96/15123, WO 97/19059 and WO 96/31475).

Additionally, pyridine-containing compounds have been reported to be useful as antibiotics. See: International Patent Application Publication Nos. WO 97/29111 and WO 96/02505; Canadian Patent Application No. CA 2,085,137; European Patent Application Publication No. EP 554004; and Japanese Patent Application Publication No. JP 01047789.

Tetrahydropyridines have been reported to be useful in the development of treatments for Parkinson's disease (Goulet et al. *Neuroscience* 1997, 79, 497–507), as D3 receptor agonists (European Patent Application No. EP 96-402672), as intermediates in the preparation of bactericides and antibiotics (Japanese Patent Application Publication No. JP 01233270) and as D4 receptor ligands in the treatment or prevention of schizophrenia (International Patent Publication No. WO 96/05200).

Aminopyridines are reported as effective in treatment of neurological diseases and etiologically related symptomology (U.S. Pat. No. 5,668,117), as kainic acid neuronotoxicity inhibitors (International Patent Publication No. WO 97/17970), as nitric oxide synthetase inhibitors (Japanese Patent Publication No. JP 09077668), in treatment of a variety of central nervous system and gastrointestinal disorders (International Patent Publication No. WO 96/11930), in the treatment of asthma, arthritis and related diseases (U.S. Pat. No. 5,322,847), as antibiotics (European Patent Application Publication Nos. EP 581501 and EP 467434; International Patent Application Publication Nos. WO 93/19072, WO 92/22556 and WO 92/21683, U.S. Pat. Nos. 5,077,287, 5,034,384, 5,032,587 and 4,692,443; Japanese Patent Application Publication No. JP 62181284; German Patent Application Publication No. DD 290423) and as 5-HT2C antagonists (International Patent Publication No. WO 95/01976).

Based on the forgoing discussion, there is a need for libraries possessing these unique scaffolds. Libraries of analogs of the intermediates used in the syntheses of these compounds would be useful in providing analogs of the natural products which may be useful as new therapeutic agents and in determining the active pharmacophores they possess. Libraries of analogs of compounds with known indications would also be useful in the discovery of new therapeutic agents.

Thus, there is a need for solid phase and combinatorial methods which provide diverse pyridine-derived scaffolds and libraries in an efficient manner. There is also a need for diverse libraries of compounds possessing unique scaffolds or pharmacophores, in particular, libraries of dihydropyridones, N-acyldihydropyridones, tetrahydropyridones, pyridines, aminopyridines, N-acyltetrahydropyridines and tetrahydropyridines.

Therefore, it is an object herein to provide solid phase methods for preparation of these compounds and to produce such compounds. It is also an object herein to provide libraries of these compounds, produced by the methods. A further object herein is to provide pharmaceutical compositions containing the compounds produced by the methods.

SUMMARY OF THE INVENTION

Methods for solid phase synthesis using a resin activation/capture approach are provided. The methods can be readily adapted for use in combinatorial synthetic schemes. In particular the methods involve substantially simultaneously activating a substrate toward reaction with a reagent with which it would otherwise be unreactive and capturing the substrate on a resin or other solid support. This feature allows for the solid phase synthesis of compounds that heretofore could not be so-produced. The ability to synthesize such compounds in the solid phase permits the methods to be adapted to combinatorial synthesis protocols, which rely on or require solid phase syntheses. The methods thus provide a means to prepare libraries of compounds that would be difficult or impossible to obtain using solution phase syntheses. Advantageously, compounds produced are of increased purity relative to solution phase methods. The substrates contain heteroaryl groups containing one ring or a plurality of fused rings, typically two or three, and at least one nitrogen. It is the nitrogen that is reacted with the functionalized resin.

The resin or other solid support is a resin suitable for solid phase chemical synthesis that has been modified or functionalized as described herein. Generally, the resin or other solid support has been modified such that exposure of a heteroaryl compound in which at least one of the heteroatoms is nitrogen to the modified resin activates the heteroaryl compound toward reaction with a nucleophile with which it would otherwise be unreactive. Preferred resins and other solid supports are those with functional groups that are active as acylating, sulfonylating or phosphorylating agents.

The resin activation/capture approach is schematically set forth as follows:

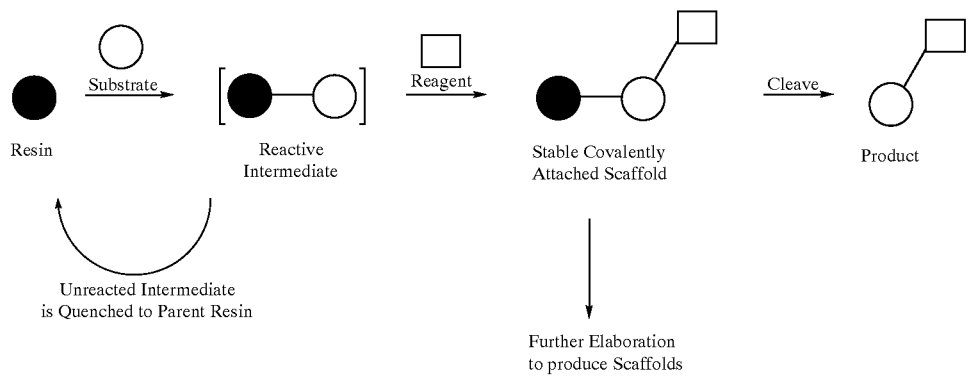

where the activation of the substrate and the capture of the substrate on the resin or other solid support occur substantially simultaneously to give a reactive intermediate, which can then be reacted to produce desired compounds. Such substantial simultaneous resin activation/capture allows for efficient solid phase syntheses, where activation is required for reaction with a particular reagent. The reactive intermediate then combines with the reagent to afford a stable covalently attached scaffold, which is either cleaved to provide the product compounds, or is elaborated further to afford scaffolds for library construction. Advantageously, any unreacted reactive intermediate is quenched to the parent resin upon hydrolysis, thereby reducing the amount and number of impurities present in the resulting compounds.

The methods provided herein include the steps of simultaneously or substantially simultaneously capturing a substrate on a resin or other solid support and activating the substrate toward reaction with a reagent with which it would otherwise be unreactive; and reacting the activated substrate with the reagent. The methods, in preferred embodiments, further involve the steps of, optionally, subsequently modifying the substrate; and cleaving the modified substrate from the resin to provide the desired compounds.

In one embodiment this method includes the steps of (a) simultaneously capturing a substrate to be modified on a modified resin or other solid support and activating the substrate toward reaction with a reagent with which the substrate would otherwise be unreactive to give an activated substrate; (b) reacting the reagent with the activated substrate to give an addition product; (c) optionally, hydrolyzing the addition product under acidic conditions to give a ketone; (d) optionally, subsequently modifying the ketone or addition product to form a modified substrate; and (e) cleaving the addition product, ketone or modified substrate from the resin or other solid support with optional oxidation or reduction of the addition product, ketone or modified substrate to the compound.

Other solid phase synthesis methods for providing compounds and libraries of interest also provided. In one embodiment, the method involves the steps of (a) immobilizing a substrate on a resin or other solid support; (b) activating the immobilized substrate toward reaction with a reagent with which it would otherwise be unreactive by reaction with an activating agent to form an activated substrate; (c) reacting the activated substrate with the reagent to form an addition product; (d) hydrolyzing the addition product to provide a ketone; (e) reductively aminating the ketone to give a modified substrate; and (f) cleaving the modified substrate from the resin or other solid support under acidic conditions, with optional oxidation of the modified substrate.

In another embodiment, the method involves the steps of (a) immobilizing a substrate on a resin or other solid support; (b) activating the immobilized substrate toward reaction with a reagent with which it would otherwise be unreactive by reaction with an activating agent to give an activated substrate; (c) reacting the activated substrate with the reagent to give an addition product; and (d) cleaving the addition product from the resin or other solid support under acidic conditions.

The methods herein may be included as part of synthetic protocols for synthesizing libraries of compounds. Production of libraries of compounds can be achieved by using the above methods to produce a plurality of compounds in accord with any desired combinatorial synthesis protocol. Such protocols can involve the use of multiple resins or other solid supports, multiple reagents and modification of the substrate in diverse ways using various methods and reagents. The resins or other solid supports may be pins, beads, or any solid support known to the skilled artisan. The supports may be used in conjunction with multi-well plates, where a different combination of reagents and modification of methods is used in each well to provide libraries of interest (see, e.g., International PCT application No. WO 97/35198 and International PCT application No. WO 94/11388). In an exemplary embodiment, a single compound is prepared in each well and the compounds formed in the wells collectively form the libraries. Alternatively, following each transformation, the supports bearing the resin-bound products are pooled and randomly split into a number of groups. Each group is then modified using a different method or reagent. This pool/split/modify protocol is then repeated a desired number of times to afford the diverse libraries of interest.

Compounds produced by the methods are provided. The compounds are dihydropyridones, N-acyidihydropyridones, tetrahydropyridones, pyridines, aminopyridines, N-acyltetrahydropyridines and tetrahydropyridines are provided. Included among the compounds that can be made by the methods are previously unknown compounds, such as those set forth in the examples, and also known compounds, such as compounds among those described in U.S. Pat. Nos. 5,594,011, 5,585,388 and 5,567,710, and International Patent Application Publication No. WO 97/19059, which are modulators of acetylcholine receptors.

Compounds and pharmaceutical compositions containing the compounds produced by the methods are also provided. The compounds, which form a class of pyridone and pyridine scaffolds, possess a unique pharmacophore and may be screened for biological activity using assays described herein or any other assays known to those of skill in the art. These compounds contained should be useful as candidates for the prevention or treatment of neurological disorders. Such disorders for which compounds would be candidate therapeutic agents, include, but are not limited to: schizophrenia, Alzheimer's disease, disorders of extrapyramidal motor function, such as Parkinson's disease, progressive supramuscular palsy, Huntington's disease, Gilles de la Tourette syndrome and tardive dyskinesia, obesity, severe pain, drug and tobacco withdrawal, respiration, mood and emotional disorders such as depression, anxiety and psychosis, motor control and function, focus and attention disorders, concentration disorders, memory loss, cognitive impairment, dementia (including AIDS dementia), neurodegenerative disorders, epilepsy, cardiovascular dysfunction including hypertension and cardiac arrhythmias, convulsive disorders, eating disorders, including bulimia and anorexia. The compounds may be candidates for treatment of other disorders, including, but not limited to: autonomic disorders including dysfunction of gastrointestinal motility and function such as inflammatory bowel disease, irritable bowel syndrome, diarrhea, constipation, gastric acid secretion and ulcers, comedication in surgical procedures and pheochromocytoma.

The compounds may also be useful as intermediates in the preparation of alkaloid natural products, and in treatment of heart insufficiency, hyperprolactinemia, bacterial infections, asthma and arthritis.

Compounds and pharmaceutical compositions containing the compounds for use as therapeutic agents are also provided. The compounds are useful candidates for treatment of the above-noted disorders. The compounds are prepared by the methods provided herein and have the formulae:

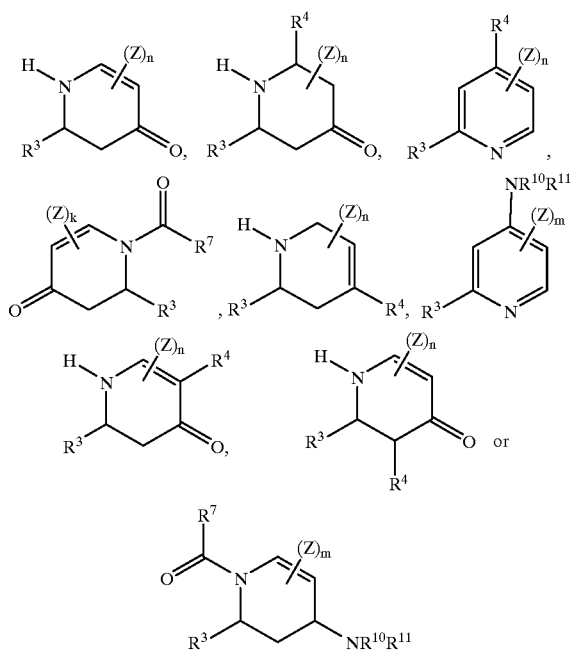

where $R^3$ is alkyl, alkenyl, alkynyl, aryl, arylalkyl, heteroaryl or heteroarylalkyl; $R^4$ is selected from hydrogen, alkyl, aryl, heteroaryl, arylalkyl, heteroarylalkyl, halo, amino, azido, cyano, nitro, alkylcarbonyl, arylcarbonyl, heteroarylcarbonyl, arylalkylcarbonyl, heteroarylalkylcarbonyl, carboxy, alkoxycarbonyl, aryloxycarbonyl, heteroaryloxycarbonyl, arylalkoxycarbonyl, heteroarylalkoxycarbonyl, thio, alkylthio and arylthio, and may be further substituted with one or more Z substituents, where each Z is indpendently selected from suitable groups, which include halogen, nitrile, nitro, formyl, alkyl, haloalkyl, polyhaloalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, dialkylaminoalkyl, diarylaminoalkyl, dialkylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsufonyl, arylsulfinyl, arylsulfonyl, aminosulfonyl, alkylaminosulfonyl, dialkylaminosulfonyl, arylaminosulfonyl or diarylaminosulfonyl; $R^7$ is alkyl, aryl, heteroaryl, arylalkyl, heteroarylalkyl, alkoxy, aryloxy, arylalkoxy or heteroarylalkoxy; and $R^{10}$ and $R^{11}$ are each independently hydrogen, alkyl, aryl, heteroaryl, arylalkyl or heteroarylalkyl, or together form alkylene or alkenylene.

In addition to the compounds that are produced by the methods herein, pharmaceutically acceptable derivatives of the compounds are provided herein. Such derivatives include salts, esters, acids, bases, solvates, hydrates and prodrugs. The derivatives may be prepared by methods known to those of ordinary skill in the art. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl) aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Methods for prevention or treatment of neurological disorders, such as schizophrenia, Alzheimer's disease, disorders of extrapyramidal motor function, such as Parkinson's disease, progressive supramuscular palsy, Huntington's disease, Gilles de la Tourette syndrome and tardive dyskinesia, obesity, severe pain, drug and tobacco withdrawal, respiration, mood and emotional disorders such as depression, anxiety and psychosis, motor control and function, focus and attention disorders, concentration disorders, memory loss, cognitive impairment, dementia (including AIDS dementia), neurodegenerative disorders, epilepsy, cardiovascular dysfunction including hypertension and cardiac arrhythmias, convulsive disorders, eating disorders, including bulimia and anorexia, autonomic disorders including dysfunction of gastrointestinal motility and function such as inflammatory bowel disease, irritable bowel syndrome, diarrnea, constipation, gastric acid secretion and ulcers, comedication in surgical procedures and pheochromocytoma; or for prevention or treatment of heart insufficiency, hyperprolactinemia, bacterial infections, asthma and arthritis by administration of one or more of the compounds in pharmaceutically acceptable carriers or pharmaceutical compositions provided herein are provided.

In practicing the methods, effective amounts of compositions containing therapeutically effective concentrations of the compounds formulated for oral, intravenous, local and topical application for the treatment of neurological disorders, such as schizophrenia, Alzheimer's disease, disorders of extrapyramidal motor function, such as Parkinson's disease, progressive supramuscular palsy, Huntington's disease, Gilles de la Tourette syndrome and tardive dyskinesia, obesity, severe pain, drug and tobacco withdrawal, respiration, mood and emotional disorders such as depression, anxiety and psychosis, motor control and function, focus and attention disorders, concentration disorders, memory loss, cognitive impairment, dementia (including AIDS dementia), neurodegenerative disorders, epilepsy, cardiovascular dysfunction including hypertension and cardiac arrhythmias, convulsive disorders, eating disorders, including bulimia and anorexia, autonomic disorders including dysfunction of gastrointestinal motility and function such as inflammatory bowel disease, irritable bowel syndrome, diarrhea, constipation, gastric acid secretion and ulcers, comedication in surgical procedures and pheochromocytoma; or for treatment of heart insufficiency, hyperprolactinemia, bacterial infections, asthma and arthritis are administered to an individual exhibiting the symptoms of one or more of these disorders. The compositions may be formulated for single or multiple dose administration, sustained release administration or for administration with other active ingredients. The amounts are effective to ameliorate or eliminate one or more symptoms of the disorders.

Articles of manufacture containing packaging material, a compound or composition, or salt, ester, acid, base, solvate, hydrate, or prodrug thereof, provided herein, which is effective for ameliorating the symptoms of any the above-noted disorders, and a label that indicates that the compound or composition, or salt, ester, acid, base, solvate, hydrate, or prodrug thereof, is used for ameliorating the symptoms of the disorder.

DETAILED DESCRIPTION OF PREFERRED EMBODIMENTS

A. Definitions

Unless defined otherwise, all technical and scientific terms used herein have the same meaning as is commonly understood by one of skill in the art to which this invention belongs. All patents and publications referred to herein are incorporated by reference.

As used herein, a strong base is a metal salt of a compound with a pKa of greater than 20, preferably greater than 25, more preferably greater than 30. Preferred metals include lithium, sodium and potassium. Exemplary strong bases include lithium diisopropylamide and butyllithium.

As used herein, dehydrative coupling involves the formation of a covalent bond with loss of water. An example of dehydrative coupling is a Mitsunobu reaction (see, e.g., Mitsunobu *Synthesis* 1981, 1).

As used herein, a linker is a compound which is used to bind, through covalent means, a substrate molecule to a solid support, such as a resin.

As used herein, alkyl, alkenyl and alkynyl carbon chains, if not specified contain from 1 to 20 carbons, preferably 1 to 16 carbons, and are straight or branched. Alkenyl carbon chains of from 1 to 20 carbons preferably contain 1 to 8 double bonds, and the alkenyl carbon chains of 1 to 16 carbons preferably contain 1 to 5 double bonds. Alkynyl carbon chains of from 1 to 20 carbons preferably contain 1 to 8 triple bonds, and the alkynyl carbon chains of 1 to 16 carbons preferably contain 1 to 5 triple bonds. The alkyl, alkenyl and alkynyl groups may be optionally substituted, with one or more groups, preferably alkyl group substituents that may be the same or different. As used herein, lower alkyl, lower alkenyl, and lower alkynyl refer to carbon chains having less than or equal to about 6 carbons.

As used herein, an alkyl group substituent includes halo, haloalkyl, preferably halo lower alkyl, aryl, hydroxy, alkoxy, aryloxy, alkyloxy, alkylthio, arylthio, aralkyloxy, aralkylthio, carboxy alkoxycarbonyl, oxo and cycloalkyl.

As used herein, "aryl" refers to cyclic groups preferably containing from 3 to 19 carbon atoms, preferably 3 to 10 members, more preferably 5 to 7 members. An aryl group may contain one ring of preferably 3 to 7 members or fused bicyclic, tricyclic or multicyclic rings. Aryl groups include, but are not limited to groups, such as phenyl, substituted phenyl, naphthyl, substituted naphthyl, in which the substituent is preferably lower alkyl, halogen, or lower alkoxy.

As used herein, an "aryl group substituent" includes alkyl, cycloalkyl, cycloalkylalkyl, aryl, heteroaryl optionally substituted with 1 or more, preferably 1 to 3, substituents selected from halo, halo alkyl and alkyl, arylalkyl, heteroarylalkyl, alkenyl containing 1 to 2 double bonds, alkynyl containing 1 to 2 triple bonds, halo, hydroxy, haloalkyl and polyhaloalkyl, preferably halo lower alkyl, especially trifluoromethyl, formyl, alkylcarbonyl, arylcarbonyl that is optionally substituted with 1 or more, preferably 1 to 3, substituents selected from halo, halo alkyl and alkyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl and arylaminosulfonyl.

As used herein, "arylalkyl" refers to an alkyl group which substituted with one or more aryl groups. Examples of arylalkyl groups include benzyl, 9-fluorenylmethyl, naphthylmethyl, diphenylmethyl and triphenylmethyl.

As used herein, "cycloalkyl" refers to a saturated mono- or multicyclic ring system, preferably of 3 to 10 carbon atoms, more preferably 3 to 6 carbon atoms; cycloalkenyl and cycloalkynyl refer to mono- or multicyclic ring systems that respectively include at least one double bond and at least one triple bond. Cycloalkenyl and cycloalkynyl groups may preferably contain 3 to 10 carbon atoms, with cycloalkenyl groups more preferably containing 4 to 7 carbon atoms and cycloalkynyl groups more preferably containing 8 to 10 carbon atoms. The ring systems of the cycloalkyl, cycloalkenyl and cycloalkynyl groups may be composed of one ring or two or more rings which may be joined together in a fused, bridged or spiro-connected fashion, and may be optionally substituted with one or more alkyl group substituents.

As used herein, "heteroaryl" refers to a monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroaryl may be optionally substituted with one or more, preferably 1 to 3, aryl group substituents. Exemplary heteroaryl groups include, for example, furanyl, thienyl, pyridyl, pyrrolyl, N-methylpyrrolyl, quinolinyl and isoquinolinyl, with pyridyl and quinolinyl being preferred.

As used herein, "heterocyclic" refers to a monocyclic or multicyclic ring system, preferably of 3 to 10 members, more preferably 4 to 7 members, even more preferably 5 to 6 members, where one or more, preferably 1 to 3 of the atoms in the ring system is a heteroatom, that is, an element other than carbon, for example, nitrogen, oxygen and sulfur atoms. The heterocycle may be optionally substituted with one or more, preferably 1 to 3 aryl group substituents. Preferred substituents of the heterocyclic group include hydroxy, alkoxy containing 1 to 4 carbon atoms, halo lower alkyl, including trihalomethyl, such as trifluoromethyl, and halogen. As used herein, the term heterocycle may include reference to heteroaryl. Exemplary heterocycles include, for example, pyrrolidinyl, piperidinyl, alkylpiperidinyl, morpholinyl, oxadiazolyl or triazolyl.

As used herein, the nomenclature alkyl, alkoxy, carbonyl, etc. are used as is generally understood by those of skill in this art. For example, as used herein alkyl refers to saturated carbon chains that contain one or more carbons; the chains may be straight or branched or include cyclic portions or be cyclic. As used herein, alicyclic refers to aryl groups that are cyclic.

As used herein, "halogen" or "halide" refers to F, Cl, Br or I.

As used herein, pseudohalides are compounds that behave substantially similar to halides. Such compounds can be used in the same manner and treated in the same manner as halides (X⁻, in which X is a halogen, such as Cl or Br). Pseudohalides include, but are not limited to cyanide, cyanate, thiocyanate, selenocyanate, trifluoromethyl and azide.

As used herein, "haloalkyl" refers to a lower alkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO— in which R is a haloalkyl group.

As used herein, "sulfinyl" refers to —S(O)—. As used herein, "sulfonyl" refers to —S(O)$_2$—.

As used herein, "aminocarbonyl" refers to —C(O)NH$_2$.

As used herein, "alkylaminocarbonyl" refers to —C(O)NHR in which R is hydrogen or alkyl, preferably lower alkyl. As used herein "dialkylaminocarbonyl" as used herein refers to —C(O)NR'R in which R' and R are independently selected from hydrogen or alkyl, preferably lower alkyl; "carboxamide" refers to groups of formula —NR'COR. As used herein, "diarylaminocarbonyl" refers to —C(O)NRR' in which R and R' are independently selected from aryl, preferably lower aryl, more preferably phenyl. As used herein, "arylalkylaminocarbonyl" refers to —C(O)NRR' in which one of R and R' is aryl, preferably lower aryl, more preferably phenyl, and the other of R and R' is alkyl, preferably lower alkyl. As used herein, "arylaminocarbonyl" refers to —C(O)NHR in which R is aryl, preferably lower aryl, more preferably phenyl.

As used herein, "alkoxycarbonyl" refers to —C(O)OR in which R is alkyl, preferably lower alkyl.

As used herein, "aryloxycarbonyl" refers to —C(O)OR in which R is aryl, preferably lower aryl, more preferably phenyl.

As used herein, "alkoxy" and "thioalkoxy" refer to RO— and RS—, in which R is alkyl, preferably lower alkyl.

As used herein, "aryloxy" and "thioaryloxy" refer to RO— and RS—, in which R is aryl, preferably lower aryl, more preferably phenyl.

As used herein, "alkylene" refers to a straight, branched or cyclic, preferably straight or branched, bivalent aliphatic hydrocarbon group, preferably having from 1 to about 20 carbon atoms, more preferably 1 to 12 carbons, even more preferably lower alkylene. The alkylene group is optionally substituted with one or more "alkyl group substituents." There may be optionally inserted along the alkylene group one or more oxygen, sulphur or substituted or unsubstituted nitrogen atoms, where the nitrogen substituent is alkyl as previously described. Exemplary alkylene groups include methylene (—CH$_2$—), ethylene (—CH$_2$CH$_2$—), propylene (—(CH$_2$)$_3$—), cyclohexylene (—C$_6$H$_{10}$—), methylenedioxy (—O—CH$_2$—O—) and ethylenedioxy (—O—(CH$_2$)$_2$—O—). The term "lower alkylene" refers to alkylene groups having 1 to 6 carbons. Preferred alkylene groups are lower alkylene, with alkylene of 1 to 3 carbon atoms being particularly preferred.

As used herein, "alkenylene" refers to a straight, branched or cyclic, preferably straight or branched, bivalent aliphatic hydrocarbon group, preferably having from 1 to about 20 carbon atoms and at least one double bond, more preferably 1 to 12 carbons, even more preferably lower alkenylene. The alkenylene group is optionally substituted with one or more "alkyl group substituents." There may be optionally inserted along the alkenylene group one or more oxygen, sulphur or substituted or unsubstituted nitrogen atoms, where the nitrogen substituent is alkyl as previously described. Exemplary alkenylene groups include —CH=CH—CH=CH— and —CH=CH—CH$_2$—. The term "lower alkenylene" refers to alkenylene groups having 2 to 6 carbons. Preferred alkenylene groups are lower alkenylene, with alkenylene of 3 to 4 carbon atoms being particularly preferred.

As used herein, "alkynylene" refers to a straight, branched or cyclic, preferably straight or branched, bivalent aliphatic hydrocarbon group, preferably having from 1 to about 20 carbon atoms and at least one triple bond, more preferably 1 to 12 carbons, even more preferably lower alkynylene. The alkynylene group is optionally substituted with one or more "alkyl group substituents." There may be optionally inserted along the alkynylene group one or more oxygen, sulphur or substituted or unsubstituted nitrogen atoms, where the nitrogen substituent is alkyl as previously described. Exemplary alkynylene groups include —C≡C—C≡C—, —C≡C— and —C≡C—CH$_2$—. The term "lower alkynylene" refers to alkynylene groups having 2 to 6 carbons. Preferred alkynylene groups are lower alkynylene, with alkynylene of 3 to 4 carbon atoms being particularly preferred.

As used herein, "arylene" refers to a monocyclic or polycyclic, preferably monocyclic, bivalent aromatic group, preferably having from 1 to about 20 carbon atoms and at least one aromatic ring, more preferably 1 to 12 carbons, even more preferably lower arylene. The arylene group is optionally substituted with one or more "alkyl group substituents." There may be optionally inserted around the arylene group one or more oxygen, sulphur or substituted or unsubstituted nitrogen atoms, where the nitrogen substituent is alkyl as previously described. Exemplary arylene groups include 1,2-, 1,3- and 1,4-phenylene. The term "lower arylene" refers to arylene groups having 5 or 6 carbons. Preferred arylene groups are lower arylene.

As used herein, "heteroarylene" refers to a bivalent monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroarylene group may be optionally substituted with one or more, preferably 1 to 3, aryl group substituents. Exemplary heteroarylene groups include, for example, 1,4-imidazolylene.

As used herein, "alkylidene" refers to a bivalent group, such as =CR'R", which is attached to one atom of another group, forming a double bond. Exemplary alkylidene groups are methylidene (=CH$_2$) and ethylidene (=CHCH$_3$). As used herein, "arylalkylidene" refers to ar alkylidene group in which either R' or R" is an aryl group.

As used herein, "amido" refers to a bivalent group, either —C(O)NH— or —HNC(O)—. "Thioamido" refers to either —C(S)CH— or —HNC(S)—. "Oxyamido" refers to either —OC(O)NH— or —HNC(O)O—. "Thiaamido" refers to either —SC(O)NH— or —HNC(O)S—. "Dithiaamido" refers to either —SC(S)NH— or —HNC(S)S—. "Ureido" refers to —HNCONH—. "Thioureido" refers to —HNCSNH—.

As used herein, the term "amino acid" refers to α-amino acids which are racemic, or of either the D- or L-configuration.

As used herein, when any particular group, such as phenyl or pyridyl, is specified, this means that the group is unsubstituted or is substituted. Preferred substituents where not specified are halo, halo lower alkyl, and lower alkyl.

As used herein, the term "library" refers to a collection of diverse compounds, which may be random or based upon a selected pharmacophore or scaffold. Of particular interest are diverse organic compounds produced by the methods provided herein.

As used herein, combinatorial chemistry is a synthetic strategy that produces diverse, usually large (typically $10^2$–$10^6$ or more members), chemical libraries. It is the systematic and repetitive, covalent connection of a set, the basis set, of different monomeric building blocks of varying structure to each other to produce an array of diverse molecules (see, e.g., Gallop et al. (1994) *J. Medicinal Chemistry* 37:1233–1251). It also encompasses other chemical modifications, such as cyclizations, eliminations, cleavages, etc., that are carried in manner that generaltes permutations and thereby collections of diverse molecules.

As used herein, the biological activity or bioactivity of a particular compound includes any activity induced, potentiated or influenced by the compound in vivo or in vitro. It also includes the abilities, such as the ability of certain molecules to bind to particular receptors and to induce [or modulate] a functional response. It may be assessed by in vivo assays or by in vitro assays, such as those exemplified herein.

As used herein, adequately pure or "pure" per se means sufficiently pure for the intended use of the adequately pure compound.

As used herein, substantially pure means sufficiently homogeneous to appear free of readily detectable impurities as determined by standard methods of analysis, such as thin layer chromatography (TLC), mass spectrometry (MS), size exclusion chromatography, gel electrophoresis, particularly agarose and polyacrylamide gel electrophoresis (PAGE) and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, a receptor refers to a molecule that has an affinity for a given ligand. Receptors may be naturally-occurring or synthetic molecules. Receptors may also be referred to in the art as anti-ligands. As used herein, both terms, receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants (such as on viruses, cells, or other materials), drugs, polynucleotides, nucleic acids, peptides, cofactors, lectins, sugars, polysaccharides, cells, cellular membranes, and organelles.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11, 1726).

As used herein, simultaneous, such as simultaneous activation and capture, means that the two events occur either at the same time, or are so close in time that they appear to occur at the same time. Substantially simultaneous events are considered to be simultaneous, where the events appear to occur at the same time.

As used herein, "heteroarylium ion" refers to a heteroaryl compound which is positively charged on the heteroatom. Such positive charge may result from reaction of a heteroaryl compound where at least one of the heteroatoms is nitrogen with a reagent, such as an acylating, sulfonylating or phosphorylating agent, as described herein, forming an N-acyl, N-sulfonyl or N-phosphoryl heteroaryl compound which is positively charged.

B. Resin Activation/Capture (REACAP) and Other Solid Phase Methods

Methods are provided for solid phase and combinatorial synthesis using a resin activation/capture approach. This approach has as a key feature of simultaneous activation of a substrate toward reaction with a reagent with which it would otherwise be unreactive and capture of the substrate on a resin or other solid support. Such methods are useful in generating compounds that are otherwise difficult, if not impossible to prepare. In particular, the methods permit solid phase synthesis of such compounds and, thus, are amenable to generation of libraries of compounds.

1. Resins or Other Solid Supports a. REACAP Resins

The resins include any solid supports for solid phase synthesis that can be derivatized or functionalized as described herein known to those of skill in the art. It is understood that the resins and other solid supports contemplated are those that are suitable for use as a support for retaining molecules during syntheses or reactions.

Resins or other solid supports useful in the resin activation/capture approach generally are functionalized so as to activate a heteroaryl compound in which at least one of the heteroatoms is a nitrogen so that the heteroaryl compound reacts with a nucleophile with which it would otherwise be unreactive. The resins or other solid supports are any which are suitable for solid phase or combinatorial chemical synthesis, such as, but not limited to, inorganics, natural polymers, and synthetic polymers, including, but not limited to: cellulose, cellulose derivatives, acrylic resins, glass that is derivatized to render it suitable for use a support, silica gels, polystyrene, gelatin, polyvinyl pyrrolidone, co-polymers of vinyl and acrylamide, polystyrene cross-linked with divinylbenzene or the like (see, Merrifield *Biochemistry* 1964, 3, 1385–1390), polyacrylamides, latex gels, polystyrene, dextran, rubber, silicon, plastics, nitrocellulose, celluloses, natural sponges, silica gels, glass, metals plastic, cellulose, cross-linked dextrans, such as those sold under the tradename Sephadex (Pharmacia) and agarose gel, such as gels sold under the tradename Sepharose (Pharmacia), which is a hydrogen bonded polysaccharide-type agarose gel, and other such resins and solid phase supports known to those of skill in the art.

Preferred among these resins, are those that include, but not limited to: polystyrene/divinylbenzene resins, such as Wang resins, which are Fmoc-amino acid-4-(hydroxymethyl)phenoxymethylcopoly(styrene-1% divinylbenzene (DVD)) resin, chlorotrityl (2-chlorotritylchloride copolystyrene-DVB resin) resin, and Merrifield (chloromethylated copolystyrene-DVB) resin. Preferred resins or other solid supports include polystyrene cross-linked with divinylbenzene.

In all embodiments, the resins include or are derivatized or functionalized to include reactive groups as described herein. For use in the RECAP methods, in preferred embodiments, the resins or other solid supports are functionalized as so that they will react with a nitrogen on the heteroaryl group of the substrate to activate it and result in capture on the solid support. Such functional groups include those that act as acylating, phosphorylating or sulfonylating agents. Exemplary functionalized resins or other solids supports have the structure:

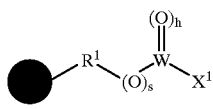

where $R^1$ is selected from alkylene, arylene, alkylarylene and arylalkylene, and is unsubstituted or substituted with one or more substituents designated Q, which, as defined herein, is halogen, hydroxy, nitrile, nitro, formyl, mercapto, carboxy, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsufonyl, arylsulfinyl, arylsulfonyl, aminosulfonyl, alkylaminosylfonyl, dialkylaminosulfonyl, arylaminosylfonyl or diarylaminosulfonyl, such that, when $R^1$ is alkylene or arylalkylene, $R^1$ is a chiral group possessing one or more stereogenic centers; $X^1$ is halo, pseudohalo, sulfonoxy, phosphoryloxy or carboxy; W is carbon, sulfur or $P(OR^{20})$, where $R^{20}$ is alkyl, aryl or arylalkyl; h is 0–2; s is 0 or 1; and

● is a resin or other solid support suitable for solid phase or combinatorial chemical synthesis, preferably polystyrene cross-linked with divinylbenzene.

In particularly preferred embodiments, the resins or other solid supports are those where $R^1$ is unsubstituted alkylene, arylene or arylalkylene; $X^1$ is halo or pseudohalo; W is carbon; h is 1; and s is 0 or 1. $R^1$ is preferably alkylene, more preferably methylene. $X^1$ is preferably halo, more preferably chloro, and s is preferably 1.

b. Immobilization Resins

In other embodiments provide herein, the resins or other solid supports immobilize a substrate to be modified. Such immobilization occurs through addition of a deprotonated substrate to an electrophilic resin or other solid support, or through dehydrative coupling of the substrate with an hydroxylated resin or other solid support.

Electrophilic resins or other solid supports include those possessing electrophilic silyl groups. Such groups include, but are not limited to, halosilanes, heteroarylsilanes and pseudohalosilanes. In preferred embodiments, the electrophilic resins or other solid supports have the structure:

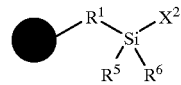

where $R^1$ is selected from alkylene, arylene, alkylarylene and arylalkylene, and is unsubstituted or substituted with one or more substituents designated Q, which, as defined herein, is halogen, hydroxy, nitrile, nitro, formyl, mercapto, carboxy, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosylfonyl or diarylaminosulfonyl, such that, when $R^1$ is alkylene or arylalkylene, $R^1$ is a chiral group possessing one or more stereogenic centers; $X^2$ is halo, heteroaryl or pseudohalo; $R^5$ and $R^6$ are each independently selected from alkyl, aryl and arylalkyl; and

● is a resin or other solid support suitable for solid phase or combinatorial chemical synthesis, preferably polystyrene cross-linked with divinylbenzene.

In preferred embodiments, the electrophilic resins or other solid supports are those where $R^1$ is unsubstituted alkylene, arylene, arylalkylene or alkylarylene. $R^1$ is preferably unsubstituted arylalkylene, more preferably phenylbutylene. $X^2$ is preferably halo, more preferably chloro. $R^5$ and $R^6$ are each preferably alkyl, more preferably ethyl.

Hydroxylated resins or other solid supports have the structure:

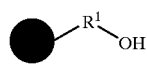

where $R^1$ is selected from alkylene, arylene, alkylarylene and arylalkylene, and is unsubstituted or substituted with one or more substituents designated Q, which, as defined herein, is halogen, hydroxy, nitrile, nitro, formyl, mercapto, carboxy, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosylfonyl or diarylaminosulfonyl, such that, when $R^1$ is alkylene or arylalkylene, $R^1$ is a chiral group possessing one or more stereogenic centers; and

● is a resin or other solid support suitable for solid phase or combinatorial chemical synthesis, preferably polystyrene cross-linked with divinylbenzene.

Preferred hydroxylated resins or other solid supports are those where $R^1$ is unsubstituted alkylene or arylalkylene, more preferably alkylene, most preferably methylene.

2. Substrates

Substrates suitable for use with the REACAP technology are monocyclic and polycyclic heteroaryl compounds in which at least one of the heteroatoms contained in the ring is a nitrogen, and are unsubstituted or are substituted with one or more Z substituents, where each Z, as defined herein, is independently selected from suitable groups, which include halogen, nitrile, nitro, formyl, alkyl, haloalkyl, polyhaloalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, dialkylaminoalkyl, diarylaminoalkyl, dialkylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl. The heteroaryl compounds preferably contain three or fewer fused rings, more preferably two or fewer fused rings and are most preferably monocyclic.

In preferred embodiments, the substrates are heteroaryl compounds where the heteroatom or heteroatoms in the ring or rings are nitrogen. Preferred substrates include pyridines, pyrimidines, pyrazines, quinolines, isoquinolines, pyridazines, phthalazines, naphthyridines, quinoxalines, quinazolines, cinnolines, pteridines, phenanthridines, acridines, perimidines, phenanthrolines and phenazines, and are unsubstituted or substituted with one or more Z substituents. In more preferred embodiments, the substrates are 2-unsubstituted-4-($R^{12}$)-pyridines, where $R^{12}$ is hydroxy, amino or thio, 2-unsubstituted-4-($R^2$)-pyridines, where $R^2$ is selected from alkoxy, aryloxy, arylalkoxy, heteroaryloxy, heteroarylalkoxy, dialkylamino, diarylamino, alkylarylamino, alkylthio and arylthio; or 3,6-unsubstituted-4($R^2$)-pyridines. Most preferred substrates include 4-methoxypyridine and 4-hydroxypyridine.

3. Reagents

Reagents that are suitable for use in the REACAP technology are nucleophiles that, in the absence of the functionalized or modified resin as described herein, are unreactive toward heteroaryl compounds where one or more of the heteroatoms in the ring or rings are nitrogen. Preferred nucleophiles are those which will react with activated heteroaryl compounds, where the activation involves reaction of the heteroaryl compounds through the nitrogen atom with an acylating, sulfonylating or phosphorylating agent, forming an N-acyl, N-sulfonyl or N-phosphoryl heteroarylium ion.

In preferred embodiments, the reagents are nucleophiles such as organometallics, preferably organolithiums, organomagnesium halides or organocadmiums. In more preferred embodiments, the reagents are organomagnesium halides (Grignard reagents), preferably alkyl, alkenyl, alkynyl, aryl, arylalkyl, heteroaryl and heteroarylalkyl magnesium halides.

4. Methods a. REACAP Methods

REACAP methods for solid phase synthesis of compounds, particularly heterocycles, and combinatorial syntheses are provided. These methods have the feature that a substrate is substantially simultaneously captured on a modified resin or other solid support and activated toward reaction with a reagent with which it would otherwise be unreactive. Suitable substrates, reagents, and modified resins or other solid supports are those described above. The substrates, reagents, and modified resins or other solid supports may be used in the REACAP method in any combination to provide a wide variety of diverse libraries and compounds. Preferred embodiments of the REACAP methods are described as follows.

In preferred embodiments, the methods provided herein involve the steps of: (a) substantially simultaneously capturing a substrate, such as a pyridine, on a modified resin or other solid support and activating the substrate toward reaction with a reagent with which the substrate would otherwise be unreactive, such as an organo magnesium halide, lithium or cadmium reagent, to give an activated substrate; (b) reacting the activated substrate with the reagent to afford a resin-bound addition product; (c) hydrolyzing the resin-bound addition product under acidic conditions, such as 3 molar aqueous hydrochloric acid or 1 molar aqueous acetic acid, to give a ketone; (d) optionally, subsequently modifying the ketone or addition product by one or more of the processes of 1,4-addition at the 6 position, electrophilic substitution at the 5 position, 1,2-addition at the 4 position and enolate alkylation at the 3 position to give a modified substrate; and (e) cleaving the addition product, ketone or modified substrate from the resin or other solid support under acidic or basic conditions with optional oxidation or reduction of the addition product, ketone or modified substrate. In a combinatorial approach, the method, in this embodiment, further involves the steps of: (A) following steps (c) and/or (d), (i) pooling the supports bearing the resin-bound product; and (ii) randomly splitting the pool into a number of groups; and (B) optionally, repeating steps (d), (i) and/or (ii) a desired number of times to provide the desired libraries. It is to be understood that for any approach in which libraries are produced, including all of the embodiments of the methods provided herein, can also include the use of chemical, radioactive, electromagnetic, optical, or other means for tagging each support to assist in deconvolution of the produced libraries. Such tagging is assists in identification of active compounds following high throughput screening of the libraries.

In the first step of the method in this embodiment, a substrate is substantially simultaneously captured on a modified resin or other solid support and activated toward reaction with a reagent with which the substrate would otherwise be unreactive to give an activated substrate. For the preparation of libraries of compounds in a combinatorial approach, multiple supports are used in order to prepare a diverse set of compounds. Preferred modified resins and other solid supports have the structure:

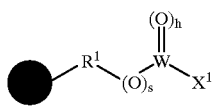

where $R^1$ is selected from alkylene, arylene, alkylarylene and arylalkylene, and is unsubstituted or substituted with one or more substituents designated Q, which, as defined herein, is halogen, hydroxy, nitrile, nitro, formyl, mercapto, carboxy, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, such that, when $R^1$ is alkylene or arylalkylene, $R^1$ is a chiral group possessing one or more stereogenic centers; $X^1$ is halo, pseudohalo or carboxy; W is carbon, sulfur or $P(OR^{20})$, where $R^{20}$ is alkyl, aryl or arylalkyl; h is 0–2; s is 0 or 1; and

is a resin or other solid support suitable for solid phase or combinatorial chemical synthesis.

Preferred substrates include pyridines, more preferably 2-unsubstituted-4-($R^2$)-pyridines, where $R^2$ is preferably selected from alkoxy, aryloxy, arylalkoxy, heteroaryloxy, heteroarylalkoxy, dialkylamino, diarylamino, alkylarylamino, alkylthio and arylthio. The 2-unsubstituted-4-($R^2$)-pyridines may be further substituted at the 3, 5 or 6 positions with one or more substituents designated Z, where each Z is independently selected from suitable groups, which include halogen, nitrile, nitro, formyl, alkyl, haloalkyl, polyhaloalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, dialkylaminoalkyl, diarylaminoalkyl, dialkylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl.

Thus, in preferred embodiments, the product of the first step of the method has the structure:

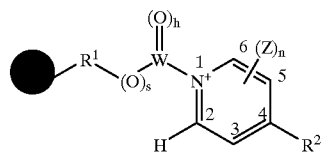

where $R^1$, $R^2$, W, h, s and Z are as defined previously and n is 0–3.

The method, in the second step in this embodiment, involves reacting the reagent with the activated substrate to give an addition product. Suitable reagents include, but are not limited to, alkyl, alkenyl, alkynyl, aryl, arylalkyl, heteroaryl and heteroarylalkyl magnesium halide, lithium and cadmium reagents. Thus, in preferred embodiments, the product of the second step has the structure:

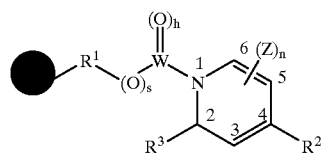

where $R^1$, $R^2$, W, Z, h, s and n are as defined previously; and $R^3$ is alkyl, alkenyl, alkynyl, aryl, arylalkyl, heteroaryl or heteroarylalkyl.

The third step of the method in this embodiment optionally involves hydrolyzing the addition product under acidic conditions, including, but not limited to, 3 molar aqueous hydrochloric acid or 1 molar aqueous acetic acid to give a ketone. Thus, in preferred embodiments, the product of the third step of the method is an immobilized 2-substituted-2,3-dihydro-4-pyridone which has the structure:

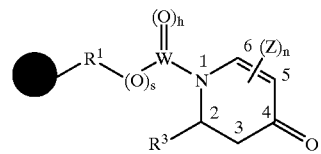

where $R^1$, $R^3$, W, Z, h, s and n are as defined previously; and the Z substituents are at the 3, 5 or 6 positions.

The method, in the fourth step in this embodiment, involves, optionally, subsequently modifying the ketone or addition product to form a modified substrate. Such modification includes, but is not limited to, the processes of 1,4-addition at the 6 position, electrophilic substitution at the 5 position, 1,2-addition at the 4 position and enolate alkylation at the 3 position. Thus, the product of the fourth step of the method, in preferred embodiments, has the formulae:

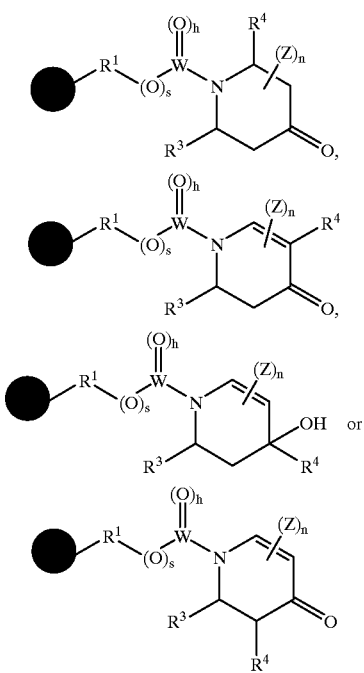

where $R^1$, $R^3$, W, Z, h, s and n are as described previously; $R^4$ is selected from hydrogen, alkyl, aryl, heteroaryl, arylalkyl, heteroarylalkyl, halo, amino, azido, cyano, nitro, alkylcarbonyl, arylcarbonyl, heteroarylcarbonyl, arylalkylcarbonyl, heteroarylalkylcarbonyl, carboxy, alkoxycarbonyl, aryloxycarbonyl, heteroaryloxycarbonyl, arylalkoxycarbonyl, heteroarylalkoxycarbonyl, thio, alkylthio and arylthio; and the Z substituents are at the 3, 5 or 6 positions.

The method, in the fifth step in this embodiment, involves cleaving the modified substrate, addition product or ketone from the resin to provide the desired compounds. The cleavage may be achieved under acidic or basic conditions, and optionally includes oxidation or reduction of the modified substrate, addition product or ketone.

In more preferred embodiments, W is carbon and h is 1. Thus, in these embodiments, the modified resins or solid supports are functionallized as haloformates or acyl halides.

Therefore, in more preferred embodiments, the modified resins or solid supports have the structure:

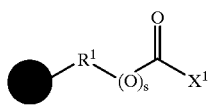

where $R^1$ is alkylene; $X^1$ is halo; s is 0 or 1, preferably 1; and

● is a resin or other solid support suitable for combinatorial chemical synthesis. Preferred resins or other solid supports are those where $R^1$ is methylene, s is 1 and $X^1$ is chloro; and include a hydroxymethylated polystyrene resin (1% divinylbenzene copolymer, 0.84–0.65 mmol/g, such as that which is commercially-available from Novabiochem, Inc. or Aldrich Chemical Co., Milwaukee, Wis.) that has been con-verted to a chloroformate solid support (see, Hauske et al. *Tetrahedron Lett.* 1995, 36, 1589–1592).

Suitable substrates include 2-unsubstituted-4-($R^2$)-pyridines, where $R^2$ is selected from alkoxy, aryloxy, arylalkoxy, heteroaryloxy and heteroarylalkoxy. The 2-unsubstituted-4-($R^2$)-pyridines may be further substituted at the 3, 5 or 6 positions with one or more indpendently selected Z substituents, but are preferably not substituted further.

Thus, in more preferred embodiments, the activated substrates have the structure:

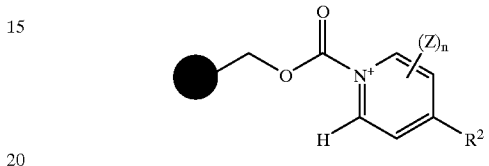

where: $R^2$ is preferably selected from alkoxy, aryloxy, arylalkoxy, heteroaryloxy, heteroarylalkoxy, dialkylamino, diarylamino, alkylarylamino, alkylthio and arylthio;

each Z is independently selected from suitable groups, which include halogen, nitrile, nitro, formyl, alkyl, haloalkyl, polyhaloalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, dialkylaminoalkyl, diarylaminoalkyl, dialkylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl; and n is 0–3, preferably 0. Following addition of the reagent, the resin-bound product has the structure:

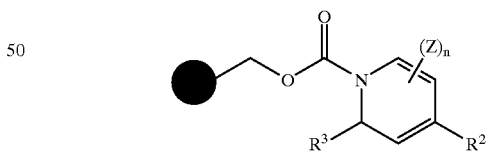

where $R^2$, Z and n are as described above and $R^3$ is preferably alkyl, alkenyl, alkynyl, aryl, arylalkyl, heteroaryl or heteroarylalkyl in which the alkyl groups are preferably lower alkyl and the heteroaryl groups preferably contain from 3 to 7 more preferably 5 or 6 members in a single ring containing 1 to 3 heteroatoms selected from O, S and N.

In more preferred embodiments, $R^2$ is alkoxy. Thus, the resin-bound product contains an enol ether, which is hydrolyzed under acidic conditions in the following step of the method to the corresponding ketone, which is an immobilized 2-($R^3$)-2,3-dihydro-4-pyridone of structure:

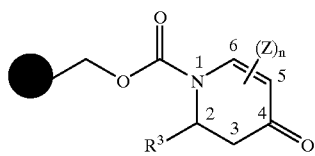

where $R^3$, Z and n are as described previously.

Following optional modification of the immobilized 2-($R^3$)-2,3-dihydro-4-pyridone, the addition product, ketone or modified substrate is cleaved from the modified resin or other solid support under acidic conditions, including, but not limited to, trifluoroacetic acid or aqueous hydrochloric acid, or basic conditions, including, but not limited to, metal alkoxide, preferably sodium methoxide and is optionally accompanied by oxidation, including, but not limited to, oxidation with $O_2$ or reduction, including, but not limited to, reduction with triethylsilane, of the modified substrate.

In a particularly preferred embodiment, the method involves the steps of (a) simultaneously capturing 4-methoxypyridine on a hydroxymethylated polystyrene resin (1% divinylbenzene copolymer, 0.84–0.65 mmol/g) which has been converted to a chloroformate solid support and activating the 4-methoxypyridine toward reaction with an alkyl, alkenyl, alkynyl, aryl, arylalkyl, heteroaryl or heteroarylalkyl Grignard (magnesium halide) or lithium reagent; (b) reacting the activated 4-methoxypyridine with the alkyl, alkenyl, alkynyl, aryl, arylalkyl, heteroaryl or heteroarylalkyl Grignard (magnesium halide) or lithium reagent to afford a resin-bound addition product; (c) hydrolyzing the resin-bound product under acidic conditions, such as 3 molar aqueous hydrochloric acid or 1 molar aqueous acetic acid to give a ketone; and (d) cleaving the ketone from the solid support under basic conditions.

Thus, the method, in this preferred embodiment, has the following scheme:

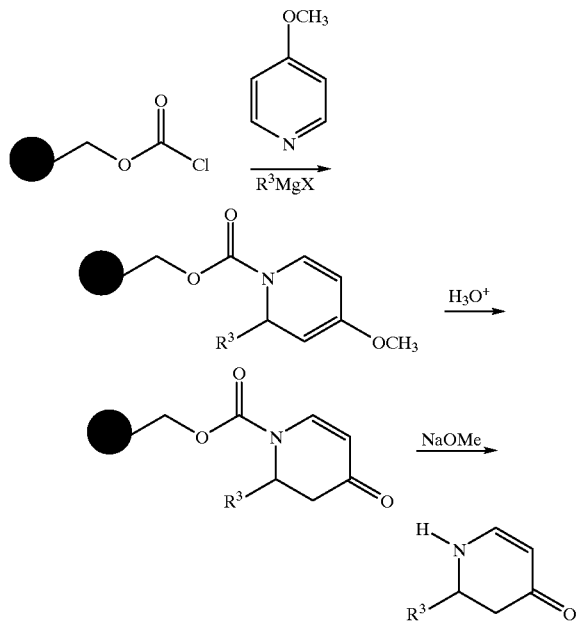

where $R^3$ is alkyl, alkenyl, alkynyl, aryl, arylalkyl, heteroaryl or heteroarylalkyl, preferably alkyl, arylalkyl or heteraylalkyl, more preferably alkyl.

A library of compounds may be produced by this embodiment of the method by selecting an appropriate protocol and using a plurality of solid supports and Grignard reagents to produce a plurality of compounds.

In another particularly preferred embodiment, the method involves the steps of (a) simultaneously capturing 4-methoxypyridine on a hydroxymethylated polystyrene resin (1% divinylbenzene copolymer, 0.84–0.65 mmol/g) which has been converted to a chloroformate solid support and activating the 4-methoxypyridine toward reaction with an alkyl, alkenyl, alkynyl, aryl, arylalkyl, heteroaryl or heteroarylalkyl Grignard (magnesium halide) or lithium reagent; (b) reacting the activated 4-methoxypyridine with the alkyl, alkenyl, alkynyl, aryl, arylalkyl, heteroaryl or heteroarylalkyl Grignard (magnesium halide) or lithium reagent to afford a resin-bound addition product; (c) hydrolyzing the resin-bound product under acidic conditions, such as 3 molar aqueous hydrochloric acid or 1 molar aqueous acetic acid to give a ketone; (d) modifying the ketone by the process of 1,4-addition at the 6 position to give a modified substrate; and (e) cleaving the modified substrate from the resin or other solid support under acidic conditions, preferably by treatment with trifluoroacetic acid. The process of 1,4-addition at the 6 position involves the addition of a reagent known by those of skill in the art to react in this manner with substrates of this class. For example, organocuprates, or other organometallic reagents, such as organomagnesium halides and organolithium compounds, in the presence of cuprous ion are effective.

Thus, the method, in this preferred embodiment, has the scheme:

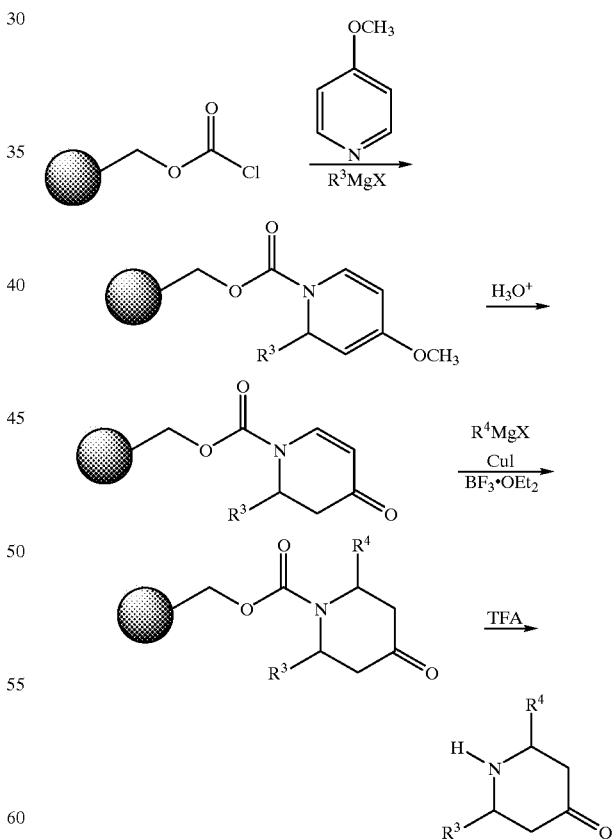

where $R^3$ is alkyl, alkenyl, alkynyl, aryl, arylalkyl, heteroaryl or heteroarylalkyl, preferably alkyl, arylalkyl or heteraylalkyl, more preferably alkyl; and $R^4$ is selected from hydrogen, alkyl, aryl, heteroaryl, arylalkyl and heteroarylalkyl.

In an exemplary combinatorial approach, this particularly preferred embodiment of the method involves the steps of (a) simultaneously capturing 4-methoxypyridine on a plurality of hydroxymethylated polystyrene resins (1% divinylbenzene copolymer, 0.84–0.65 mmol/g), which have been converted to chloroformate solid supports, and activating the 4-methoxypyridine toward reaction with a diverse group of alkyl, alkenyl, alkynyl, aryl, arylalkyl, heteroaryl or heteroarylalkyl Grignard (magnesium halide) or lithium reagents; (b) splitting the supports into separate groups; (c) reacting the activated 4-methoxypyridine with the alkyl, alkenyl, alkynyl, aryl, arylalkyl, heteroaryl or heteroarylalkyl Grignard (magnesium halide) or lithium reagents to afford resin-bound addition products; (c) hydrolyzing the resin-bound addition products under acidic conditions, such as 3 molar aqueous hydrochloric acid or 1 molar aqueous acetic acid to give ketones; (d) pooling the supports; (e) randomly splitting the supports into separate groups; (f) modifying the ketones by the process of 1,4-addition at the 6 position to give modified substrates; and (g) cleaving the modified substrates from the resins or other solid supports under acidic conditions, preferably by treatment with trifluoroacetic acid. This combinatorial synthetic scheme, may also, following step (f), involve the steps of (i) pooling the supports; (ii) randomly splitting the supports into separate groups; and (iii) modifying the modified substrates by the processes of 1,2-addition at the 4 position or enolate alkylation at the 3 or 5 positions. Alternatively, the combinatorial method may use multi-well plates, where a different combination of reagents and modification of methods is used in each well to provide libraries of interest. In an exemplary embodiment, a single compound is prepared in each well and the compounds formed in the wells collectively form the libraries.

In another more preferred embodiment, the method involves the steps of (a) simultaneously capturing 4-methoxypyridine on a hydroxymethylated polystyrene resin (1% divinylbenzene copolymer, 0.84–0.65 mmol/g) which has been converted to a chloroformate solid support and activating the 4-methoxypyridine toward reaction with an alkyl, alkenyl, alkynyl, aryl, arylalkyl, heteroaryl or heteroarylalkyl Grignard (magnesium halide) or lithium reagent; (b) reacting the activated 4-methoxypyridine with the alkyl, alkenyl, alkynyl, aryl, arylalkyl, heteroaryl or heteroarylalkyl Grignard (magnesium halide) or lithium reagent to afford a resin-bound addition product; (c) hydrolyzing the resin-bound addition product under acidic conditions, such as 3 molar aqueous hydrochloric acid or 1 molar aqueous acetic acid to give a ketone; (d) modifying the ketone by the process of 1,2-addition at the 4 position to give a modified substrate; and (e) cleaving the modified substrate from the resin or other solid support under acidic conditions, preferably by treatment with trifluoroacetic acid, with simultaneous oxidation of the modified substrate to a pyridine, preferably by treatment with $O_2$. The process of 1,2-addition at the 4 position involves the addition of a reagent known by those of skill in the art to react in this manner with substrates of this class. For example, organometallic reagents, such as organomagnesium halides and organolithium compounds, are effective.

Thus, the method, in this preferred embodiment, has the scheme:

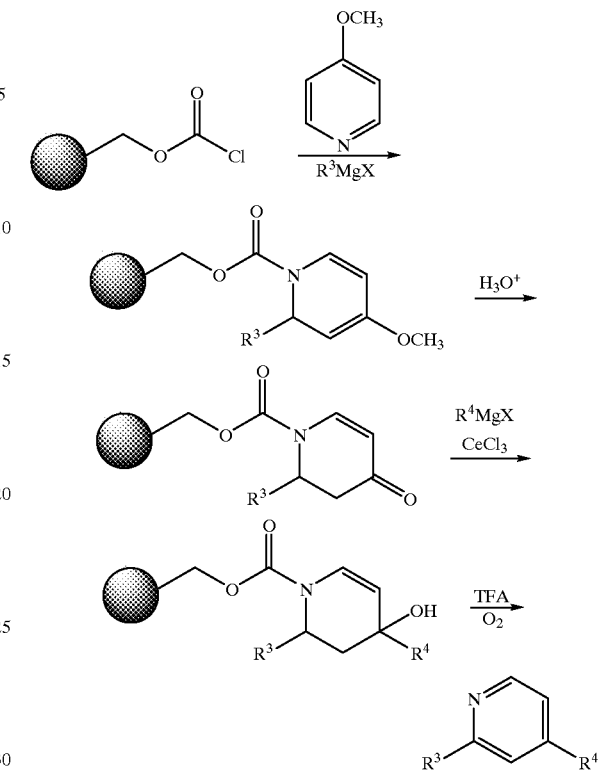

where $R^3$ is alkyl, alkenyl, alkynyl, aryl, arylalkyl, heteroaryl or heteroarylalkyl, preferably alkyl, arylalkyl or heteraylalkyl, more preferably alkyl; and $R^4$ is selected from hydrogen, alkyl, aryl, heteroaryl, arylalkyl and heteroarylalkyl. In more preferred embodiments, $R^4$ is aryl or heteroaryl.

The method, in this more preferred embodiment is an example of a traceless linker strategy for solid phase and combinatorial chemistry. This is because the products generated by this embodiment do not appear to have a point of attachment for the resin. Such traceless linker strategies are valuable in the area of pharmaceutical discovery due to the improved pharmacokinetic profile of the compounds generated (see, e.g., Plunket et al. *J. Org. Chem.* 1995, 60, 6006–6007; Han et al. *Tetrahedron Lett.* 1996, 37, 2703–2706; Lorsbach et al. *J. Org. Chem.* 1996, 61, 8716–8717; Newlander et al. *J. Org. Chem.* 1997, 62, 6726–6732).

In an exemplary combinatorial synthetic scheme, this embodiment of the method includes the steps of: (a) simultaneously capturing 4-methoxypyridine on a plurality of hydroxymethylated polystyrene resins (1% divinylbenzene copolymer, 0.84–0.65 mmol/g) which have been converted to a chloroformate solid supports and activating the 4-methoxypyridine toward reaction with a group of alkyl, alkenyl, alkynyl, aryl, arylalkyl, heteroaryl or heteroarylalkyl Grignard (magnesium halide) or lithium reagents; (b) reacting the activated 4-methoxypyridine with the alkyl, alkenyl, alkynyl, aryl, arylalkyl, heteroaryl or heteroarylalkyl Grignard (magnesium halide) or lithium reagents to afford resin-bound addition products; (c) hydrolyzing the resin-bound addition products under acidic conditions, such as 3 molar aqueous hydrochloric acid or 1 molar aqueous acetic acid to give ketones; (d) pooling the supports; (e) randomly splitting the supports into separate groups; (f) modifying the ketones by the process of 1,2-addition at the 4 position to give modified substrates; and (g) cleaving the modified substrates from the resins or other solid supports under acidic conditions, preferably by treatment with trifluoroacetic acid, with simultaneous oxidation of the modified substrates to pyridines, preferably by treatment with $O_2$. It is to be understood that the method, in this combinatorial approach, may also, following step (f), involve the steps of (i) pooling the supports; (ii) randomly splitting the supports into separate groups; and (iii) modifying the modified substrates by the process of electrophilic addition to the 5,6-alkene. Alternatively, the combinatorial method may use multi-well plates, where a different combination of reagents and modification of methods is used in each well to provide libraries of interest. In an exemplary embodiment, a single compound is prepared in each well and the compounds formed in the wells collectively form the libraries.

In another more preferred embodiment, the method involves the steps of: (a) simultaneously capturing 4-methoxypyridine on a hydroxymethylated polystyrene resin (1% divinylbenzene copolymer, 0.84–0.65 mmol/g) which has been converted to a chloroformate solid support and activating the 4-methoxypyridine toward reaction with an alkyl, alkenyl, alkynyl, aryl, arylalkyl, heteroaryl or heteroarylalkyl Grignard (magnesium halide) or lithium reagent; (b) reacting the activated 4-methoxypyridine with the alkyl, alkenyl, alkynyl, aryl, arylalkyl, heteroaryl or heteroarylalkyl Grignard (magnesium halide) or lithium reagent to afford a resin-bound addition product; (c) hydrolyzing the resin-bound addition product under acidic conditions, such as 3 molar aqueous hydrochloric acid or 1 molar aqueous acetic acid to give a ketone; (d) modifying the ketone by the process of 1,2-addition at the 4 position to give a modified substrate; and (e) cleaving the modified substrate from the resin or other solid support under acidic conditions, preferably by treatment with trifluoroacetic acid, with simultaneous reduction of the modified substrate to a tetrahydropyridine, preferably by treatment with triethylsilane. The process of 1,2-addition at the 4 position involves the addition of a reagent known by those of skill in the art to react in this manner with substrates of this class. For example, organometallic reagents, such as organomagnesium halides and organolithium compounds, are effective.

Thus, the method, in this preferred embodiment, has the scheme:

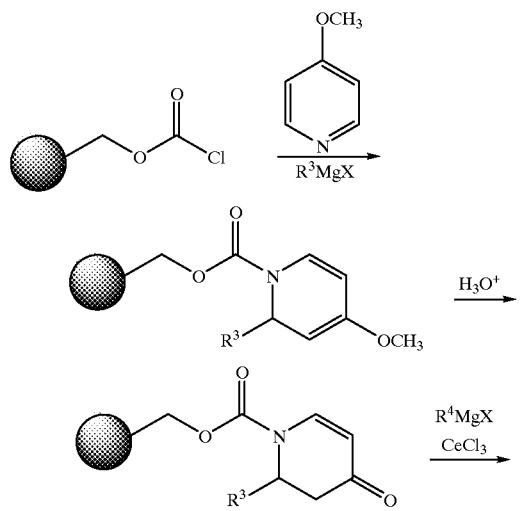

-continued

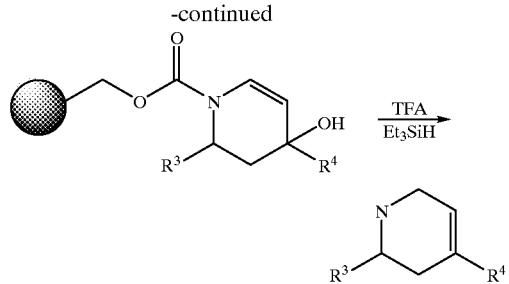

where $R^3$ is alkyl, alkenyl, alkynyl, aryl, arylalkyl, heteroaryl or heteroarylalkyl, preferably alkyl, arylalkyl or heteraylalkyl, more preferably alkyl; and $R^4$ is selected from hydrogen, alkyl, aryl, heteroaryl, arylalkyl and heteroarylalkyl.

An exemplary combinatorial synthetic scheme of this embodiment includes the steps of: (a) simultaneously capturing 4-methoxypyridine on a plurality of hydroxymethylated polystyrene resins (1% divinylbenzene copolymer, 0.84–0.65 mmol/g) which have been converted to chloroformate solid supports and activating the 4-methoxypyridine toward reaction with an group of alkyl, alkenyl, alkynyl, aryl, arylalkyl, heteroaryl or heteroarylalkyl Grignard (magnesium halide) or lithium reagents; (b) reacting the activated 4-methoxypyridine with the alkyl, alkenyl, alkynyl, aryl, arylalkyl, heteroaryl or heteroarylalkyl Grignard (magnesium halide) or lithium reagents to afford resin-bound addition products; (c) hydrolyzing the resin-bound addition products under acidic conditions, such as 3 molar aqueous hydrochloric acid or 1 molar aqueous acetic acid to give ketones; (d) pooling the supports; (e) randomly splitting the supports into separate groups; (f) modifying the ketones by the process of 1,2-addition at the 4 position to give modified substrates; and (g) cleaving the modified substrates from the resins or other solid supports under acidic conditions, preferably by treatment with trifluoroacetic acid, with simultaneous reduction of the modified substrates to tetrahydropyridines, preferably by treatment with triethylsilane. It is to be understood that the method, in this combinatorial approach, may also, following step (f), involve the steps of (i) pooling the supports; (ii) randomly splitting the supports into separate groups; and (iii) modifying the modified substrates by the process of electrophilic addition to the 5,6-alkene. Alternatively, the combinatorial method may use multi-well plates, where a different combination of reagents and modification of methods is used in each well to provide libraries of interest. In an exemplary embodiment, a single compound is prepared in each well and the compounds formed in the wells collectively form the libraries.

b. Electrophilic Resin Methods

In another embodiment, the resins or other solid supports are electrophilic and capture a nucleophilic reagent through covalent attachment at the electrophilic center. In preferred embodiments, the resins or other solid supports are modified as silane derivatives. These silane derivatives have the feature that the silicon atom is electrophilic and has as a substituent a halo, pseudohalo or heteroaryl group.

In this embodiment, the method involves the steps of (a) immobilizing a substrate on a resin or other solid support; (b) activating the immobilized substrate toward reaction with a reagent with which it would otherwise be unreactive by reaction with an activating agent to form an activated substrate; (c) reacting the activated substrate with the reagent to form an addition product; (d) hydrolyzing the addition product to provide a ketone; (e) reductively aminating the ketone to give a modified substrate; and (f) cleaving the modified substrate from the resin or other solid support under acidic conditions, with optional oxidation of the modified substrate.

In a more preferred embodiment, the resins or other solid supports have the structure:

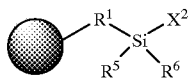

where $R^1$ is selected from alkylene, arylene, alkylarylene and arylalkylene, and is unsubstituted or substituted with one or more substituents designated Q, which, as defined herein, is halogen, hydroxy, nitrile, nitro, formyl, mercapto, carboxy, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, such that, when $R^1$ is alkylene or arylalkylene, $R^1$ is a chiral group possessing one or more stereogenic centers; $X^2$ is halo, heteroaryl or pseudohalo; and $R^5$ and $R^6$ are each independently selected from alkyl, aryl and arylalkyl.

Preferred substrates include pyridines, more preferably 3,6-unsubstituted-4($R^2$)-pyridines, where $R^2$ is selected from alkoxy, aryloxy, arylalkoxy, heteroaryloxy, heteroarylalkoxy, dialkylamino, diarylamino, alkylarylamino, alkylthio and arylthio, and may be further substituted with one or more Z substituents at the 2 and 5 positions. The activating agents have the formula $R^7COX^1$, where $R^7$ is alkyl, aryl, heteroaryl, arylalkyl, heteroarylalkyl, alkoxy, aryloxy, arylalkoxy and heteroarylalkoxy and $X^1$ is halo, pseudohalo or carboxy. The reagents include, but are not limited to, alkyl, alkenyl, alkynyl, aryl, arylalkyl, heteroaryl and heteroarylalkyl Grignard (magnesium halide), lithium and cadmium reagents.

In this embodiment, the substrate is immobilized onto the resin or other solid support by deprotonation of the substrate with a strong base, such as lithium diisopropylamide, followed by reaction with the resin or other solid support. In preferred embodiments, the substrate is a 3,6-unsubstituted-4($R^2$)-pyridine and the deprotonation/immobilization occurs at the 3 position of the pyridine. Thus, in this preferred embodiment of the method, the immobilized substrate has the structure:

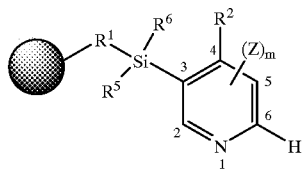

where $R^1$, $R^2$, $R^5$, $R^6$ and Z are as described previously; m is 0–2; and the Z substituents are at the 2 or 5 positions.

In the second step of this embodiment, the method involves reaction of the immobilized substrate with an activating agent of formula $R^7COX^1$. These activating agents are acyl halides and haloformates, preferably chloroformates. The product of the second step of the method in preferred embodiments is therefore of structure:

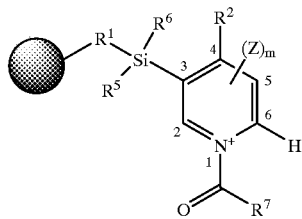

where $R^1$, $R^2$, $R^5$, $R^6$, $R^7$, Z and m are as described previously; and the Z substituents are at the 2 or 5 positions.

In the third step of this embodiment of the method, the activated substrate with the reagent to form an addition product. Suitable reagents include alkyl, alkenyl, alkynyl, aryl, arylalkyl, heteroaryl and heteroarylalkyl Grignard (magnesium halide), lithium and cadmium reagents. Thus, in preferred embodiments, the reagent will add to the 6 position of the activated pyridine to give an addition product of structure:

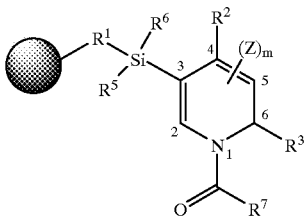

where $R^3$ is selected from alkyl, alkenyl, alkynyl, aryl, arylalkyl, heteroaryl and heteroarylalkyl; $R^1$, $R^2$, $R^5$, $R^6$, $R^7$, Z and m are as defined previously; and the Z substituents are at the 2 and 5 positions.

In the fourth step of this embodiment of the method, the addition product is hydrolyzed to provide a ketone. Thus, in preferred embodiments, the product is a pyridone of structure:

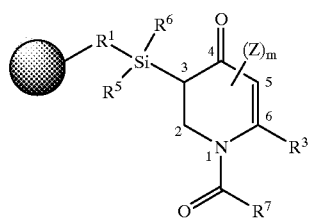

where $R^1$, $R^3$, $R^5$, $R^6$, $R^7$, Z and m are as defined previously; and the Z substituents are at the 2 and 5 positions.

The fifth step of this embodiment of the method involves reductively aminating the ketone to give a modified substrate. Amines used in the reductive amination have the formula $HNR^{10}R^{11}$, where $R^{10}$ and $R^{11}$ are each independently selected from hydrogen, alkyl, aryl, heteroaryl, arylalkyl and heteroarylalkyl, or together form alkylene or alkenylene. The modified substrate, in preferred embodiments is an immobilized 4-amino-1,2,3,4-tetrahydropyridine and has the structure:

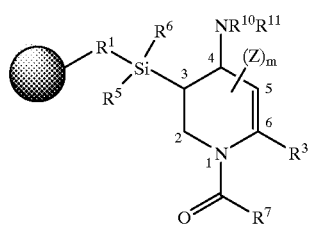

where $R^1$, $R^3$, $R^5$, $R^6$, $R^7$, $R^{10}$, $R^{11}$, Z and m are as defined previously; and the Z substituents are at the 2 and 5 positions.

In the sixth step of the method in this embodiment, the modified substrate is cleaved from the resin or other solid support under acidic conditions with optional oxidation of the modified substrate to provide the desired libraries and compounds.

In more preferred embodiments, the method involves the steps of (a) capturing 4-methoxypyridine on a halodialkylsilylbutylated, preferably a chlorodiethylsilylbutylated, polyethylene glycol/polystyrene graft copolymer (available from Argonaut Technologies, Inc., San Carlos, Calif.; this and other similar solid supports may be prepared according to Randolph et al. *J. Am. Chem. Soc.* 1995, 117, 5712–5719) by the process of deprotonating the 4-methoxypyridine at the 3 position with a strong base such as lithium diisopropylamide followed by reaction with the resin or other solid support; (b) activating the 4-methoxypyridine toward reaction with an alkyl, aryl, arylalkyl, heteroaryl or heteroarylalkyl Grignard (magnesium halide) or lithium reagent by reaction with an activating agent selected from alkyl, aryl and arylalkyl chloroformates, and alkyl, aryl and arylalkyl acyl chlorides; (c) reacting the activated 4-methoxypyridine with the alkyl, aryl, arylalkyl, heteroaryl or heteroarylalkyl Grignard (magnesium halide) or lithium reagent to afford a resin-bound addition product; (d) hydrolyzing the resin-bound addition product under acidic conditions, such as 3 molar aqueous hydrochloric acid or 1 molar aqueous acetic acid to give a ketone; (e) reductively aminating the ketone by reaction with an amine of formula $HNR^{10}R^{11}$, where $R^{10}$ and $R^{11}$ are each independently hydrogen, alkyl, aryl, heteroaryl, arylalkyl or heteroarylalkyl, or together form alkylene or alkenylene, and a reducing agent, which reduced a C=N to a C—N, such as, but not limited to, sodium borohydride, sodium cyanoborohydride, or palladium or platinum in the presence of hydrogen, ammonium formate, cyclohexene or cyclohexadiene, to afford a resin-bound amine; and (f) cleaving the resin-bound amine from the resin under acidic conditions, such as 3 molar aqueous hydrochloric acid or 1 molar aqueous acetic acid, with optional oxidation of the resin-bound amine, to afford the compounds.

Thus, the method, in this preferred embodiment, has the scheme:

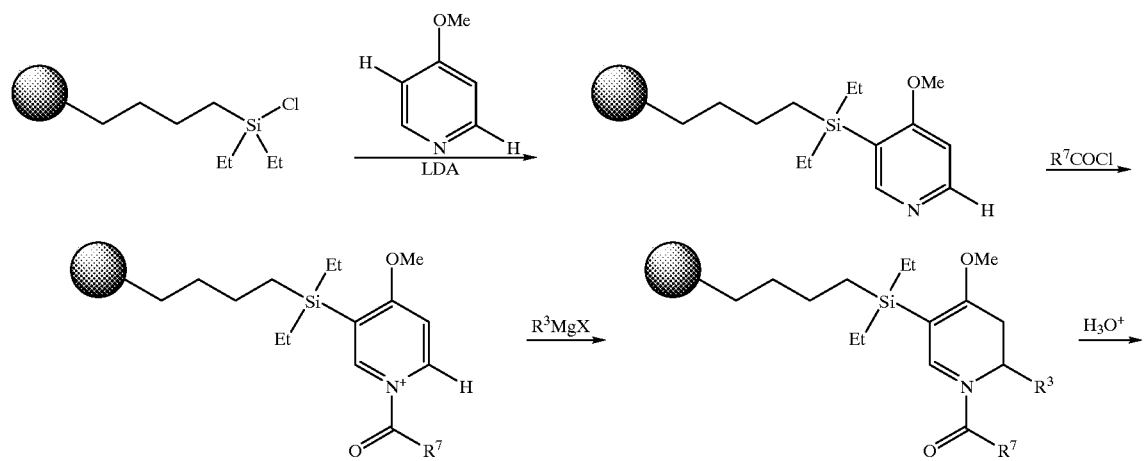

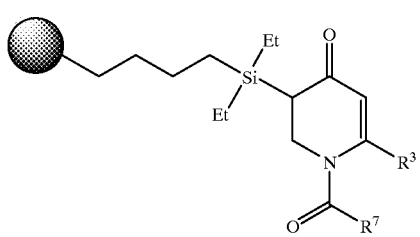
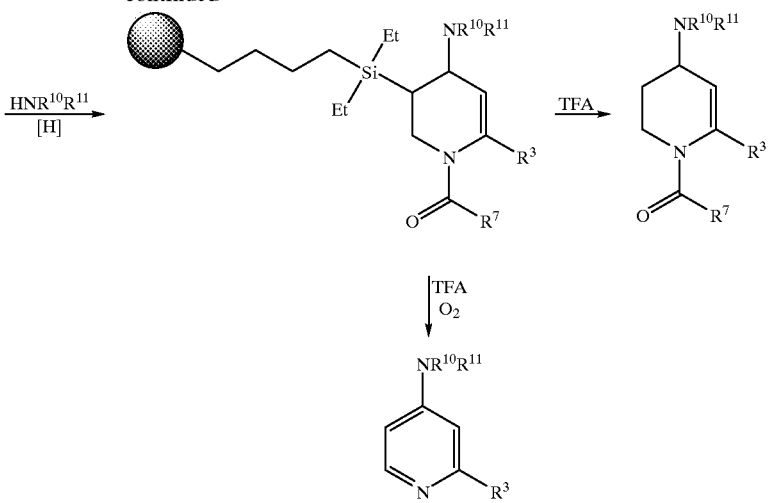

where $R^3$ is alkyl, alkenyl, alkynyl, aryl, arylalkyl, heteroaryl or heteroarylalkyl, preferably alkyl, arylalkyl or heteraylalkyl, more preferably alkyl; $R^7$ is selected from hydrogen, alkyl, aryl, heteroaryl, arylalkyl, heteroarylalkyl, alkoxy, aryloxy, arylalkoxy and heteroarylalkoxy; and $R^{10}$ and $R^{11}$ are each independently hydrogen, alkyl, aryl, heteroaryl, arylalkyl or heteroarylalkyl, or together form alkylene or alkenylene.

In a combinatorial approach, this particularly preferred embodiment of the method involves the steps of (a) capturing 4-methoxypyridine on a plurality of halodialkylsilylbutylated, preferably a chlorodiethylsilylbutylated, polyethylene glycol/polystyrene graft copolymer by the process of deprotonating the 4-methoxypyridine at the 3 position with a strong base such as lithium diisopropylamide followed by reaction with the resins or other solid supports; (b) activating the 4-methoxypyridine toward reaction with a group of alkyl, alkenyl, alkynyl, aryl, arylalkyl, heteroaryl or heteroarylalkyl Grignard (magnesium halide) or lithium reagents by reaction with an activating agent selected from alkyl, aryl and arylalkyl chloroformates, and alkyl, aryl and arylalkyl acyl chlorides; (c) randomly splitting the supports into separate groups; (d) reacting the activated 4-methoxypyridines with the alkyl, alkenyl, alkynyl, aryl, arylalkyl, heteroaryl or heteroarylalkyl Grignard (magnesium halide) or lithium reagents to afford resin-bound addition products; (e) hydrolyzing the resin-bound addition products under acidic conditions, such as 3 molar aqueous hydrochloric acid or 1 molar aqueous acetic acid to give ketones; (f) pooling the supports; (g) randomly splitting the supports into separate groups; (h) reductively aminating the ketones by reaction with a group of amines of formula $HNR^{10}R^{11}$, where $R^{10}$ and $R^{11}$ are each independently hydrogen, alkyl, aryl, heteroaryl, arylalkyl or heteroarylalkyl, or together form alkylene or alkenylene, and a reducing agent such as, but not limited to, sodium borohydride, sodium cyanoborohydride, or palladium or platinum in the presence of hydrogen, ammonium formate, cyclohexene or cyclohexadiene, to afford resin-bound amines; and (j) cleaving the resin-bound amines from the resins under acidic conditions, such as 3 molar aqueous hydrochloric acid or 1 molar aqueous acetic acid, with optional oxidation, to afford the desired libraries and compounds. Alternatively, the combinatorial method may use multi-well plates, where a different combination of reagents and modification of methods is used in each well to provide libraries of interest. In an exemplary embodiment, a single compound is prepared in each well and the compounds formed in the wells collectively form the libraries.

C. Hydroxylated Resin Methods

In another embodiment, the resins or other solid supports are hydroxyalkylated. These resins or other solid supports capture the substrate by dehydrative coupling. Dehydrative coupling involves loss of water during the coupling process. This process may be performed, for example, under Mitsunobu conditions.

In this embodiment, the method involves the steps of (a) immobilizing a substrate on a resin or other solid support; (b) activating the immobilized substrate toward reaction with a reagent with which it would otherwise be unreactive by reaction with an activating agent to give an activated substrate; (c) reacting the activated substrate with the reagent to give an addition product; and (d) cleaving the addition product from the resin or other solid support under acidic conditions.

In a more preferred embodiment, the resins or other solid supports have the structure:

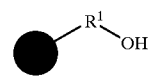

where $R^1$ is selected from alkylene, arylene, alkylarylene and arylalkylene, and is unsubstituted or substituted with one or more substituents designated Q, which, as defined herein, is halogen, hydroxy, nitrile, nitro, formyl, mercapto, carboxy, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, such that, when $R^1$ is alkylene or arylalkylene, $R^1$ is a chiral group possessing one or more stereogenic centers.

Suitable substrates include, but are not limited to, nitrogen-containing heteroaryl compounds such as pyridines, pyrimidines, pyrazines, quinolines, isoquinolines, pyridazines, phthalazines, naphthyridines, quinoxalines, quinazolines, cinnolines, pteridines, phenanthridines, acridines, perimidines, phenanthrolines and phenazines, which are substituted with $R^{12}$, where $R^{12}$ is hydroxy, amino or thio. Preferred substrates include pyridines, more preferably 2-unsubstituted-4-($R^{12}$)-pyridines; and are unsubstituted or substituted with one or more Z substituents at the 3, 5 or 6 positions. The substrate is immobilized on the resin or other solid support through a dehydrative coupling reaction, such as a Mitsunobu reaction. The activating agents have the formula $R^7COX^1$, where $R^7$ is alkyl, aryl, heteroaryl, arylalkyl, heteroarylalkyl, alkoxy, aryloxy, arylalkoxy and heteroarylalkoxy and $X^1$ is halo, pseudohalo or carboxy. The reagents include, but are not limited to, alkyl, alkenyl, alkynyl, aryl, arylalkyl, heteroaryl and heteroarylalkyl Grignard (magnesium halide), lithium and cadmium reagents.

Thus, the first step of this embodiment of the method involves immobilizing the substrate on a resin or other solid support to provide an immobilized substrate of structure:

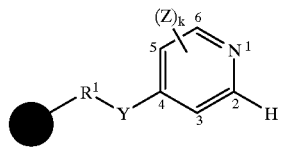

where $R^1$ and Z are as defined previously; Y is oxy, amino or thio; k is 0–3; and the Z substituent are at the 3, 5 or 6 positions.

In the second step of this embodiment of the method, the immobilized substrate is activated toward reaction with a reagent with which it would otherwise be unreactive by reaction with an activating agent. The activating agents are of formula $R^7COX^1$. These activating agents are acyl halides and haloformates. The product of the second step of the method in preferred embodiments is therefore of structure:

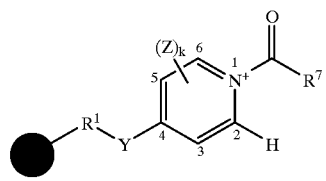

where $R^1$, $R^7$, Z, Y and k are as defined previously; and the Z substituents are at the 3, 5 or 6 positions.

The third step of the method in this embodiment involves reacting the activated substrate with the reagent to give an addition product. Suitable reagents include alkyl, alkenyl, alkynyl, aryl, arylalkyl, heteroaryl and heteroarylalkyl Grignard (magnesium halide), lithium and cadmium reagents. Thus, the addition products, in preferred embodiments, have the structure:

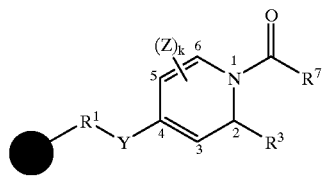

where $R^1$, $R^7$, Z, Y and k are as defined previously; $R^3$ is alkyl, alkenyl, alkynyl, aryl, arylalkyl, heteroaryl or heteroarylalkyl, preferably alkyl, arylalkyl or heteraylalkyl, more preferably alkyl; and the Z substituents are at the 3, 5 or 6 positions.

In the fourth step of this embodiment of the method, the addition product is cleaved from the resin or other solid support under acidic conditions to give the desired libraries and compounds.

In a more preferred embodiment, the method involves the steps of (a) capturing 4-hydroxypyridine on a hydroxymethylated polystyrene resin (1% divinylbenzene copolymer, 0.84–0.65 mmol/g) by coupling with the hydroxyl group; (b) activating the 4-hydroxypyridine toward reaction with an alkyl, alkenyl, alkynyl, aryl, arylalkyl, heteroaryl or heteroarylalkyl Grignard (magnesium halide) or lithium reagent by reaction with an activating agent selected from alkyl, aryl and arylalkyl chloroformates, and alkyl, aryl and arylalkylacyl chlorides; (c) reacting the activated 4-methoxypyridine with the alkyl, alkenyl, alkynyl, aryl, arylalkyl, heteroaryl or heteroarylalkyl Grignard (magnesium halide) or lithium reagent to afford a resin-bound addition product; and (d) cleaving the resin-bound addition product from the resin under acidic conditions, such as 3 molar aqueous hydrochloric acid or 1 molar aqueous acetic acid.

Thus, the method, in this preferred embodiment, has the scheme:

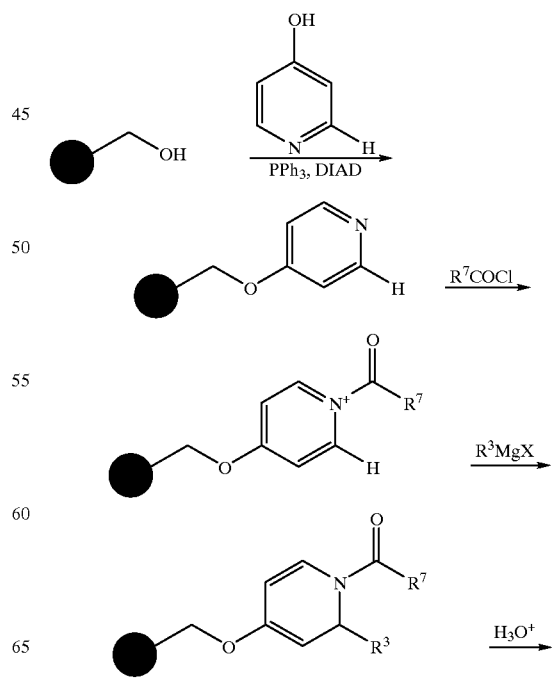

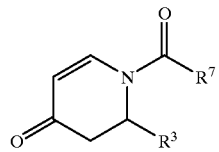

where $R^3$ is alkyl, alkenyl, alkynyl, aryl, arylalkyl, heteroaryl or heteroarylalkyl, preferably alkyl, arylalkyl or heteraylalkyl, more preferably alkyl; and $R^7$ is selected from hydrogen, alkyl, aryl, heteroaryl, arylalkyl, heteroarylalkyl, alkoxy, aryloxy, arylalkoxy and heteroarylalkoxy.

In a combinatorial approach, this particularly preferred embodiment of the method involves the steps of (a) capturing 4-hydroxypyridine on a plurality of hydroxymethylated polystyrene resins (1% divinylbenzene copolymer, 0.84–0.65 mmol/g) by coupling with the hydroxyl group; (b) splitting the supports into separate groups; (c) activating the 4-hydroxypyridine toward reaction with a group of alkyl, alkenyl, alkynyl, aryl, arylalkyl, heteroaryl or heteroarylalkyl Grignard (magnesium halide) or lithium reagents by reaction with a set of activating agents selected from alkyl, aryl and arylalkyl chloroformates, and alkyl, aryl and arylalkylacyl chlorides; (d) reacting the activated 4-methoxypyridines with the group of alkyl, alkenyl, alkynyl, aryl, arylalkyl, heteroaryl or heteroarylalkyl Grignard (magnesium halide) or lithium reagent to afford resin-bound addition products; and (d) cleaving the resin-bound addition products from the resin under acidic conditions, such as 3 molar aqueous hydrochloric acid or 1 molar aqueous acetic acid. Alternatively, the combinatorial method may use multi-well plates, where a different combination of reagents and modification of methods is used in each well to provide libraries of interest. In an exemplary embodiment, a single compound is prepared in each well and the compounds formed in the wells collectively form the libraries.

C. Compounds Prepared Using Resin Activation/Capture Approach Methods

Compounds prepared using a resin activation/capture approach method of solid phase or combinatorial synthesis provided herein are provided. The compounds are useful as therapeutic agents in the prevention or treatment of neurological disorders, such as schizophrenia, Alzheimer's disease, disorders of extrapyramidal motor function, such as Parkinson's disease, progressive supramuscular palsy, Huntington's disease, Gilles de la Tourette syndrome and tardive dyskinesia, obesity, severe pain, drug and tobacco withdrawal, respiration, mood and emotional disorders such as depression, anxiety and psychosis, motor control and function, focus and attention disorders, concentration disorders, memory loss, cognitive impairment, dementia (including AIDS dementia), neurodegenerative disorders, epilepsy, cardiovascular dysfunction including hypertension and cardiac arrhythmias, convulsive disorders, eating disorders, including bulimia and anorexia, autonomic disorders including dysfunction of gastrointestinal motility and function such as inflammatory bowel disease, irritable bowel syndrome, diarrhea, constipation, gastric acid secretion and ulcers, comedication in surgical procedures and pheochromocytoma; as intermediates in the preparation of alkaloid natural products; or for the prevention or treatment of heart insufficiency, hyperprolactinemia, bacterial infections, asthma or arthritis. Compounds which are particularly active for a certain indication may be identified using any of the assays described herein, assays contained in the incorporated U.S. Patents and Patent Applications, or other assays known to those of skill in the art.

The compounds are dihydropyridones, N-acyldihydropyridones, tetrahydropyridones, pyridines, aminopyridines, N-acyltetrahydropyridines or tetrahydropyridines, and have the formulae:

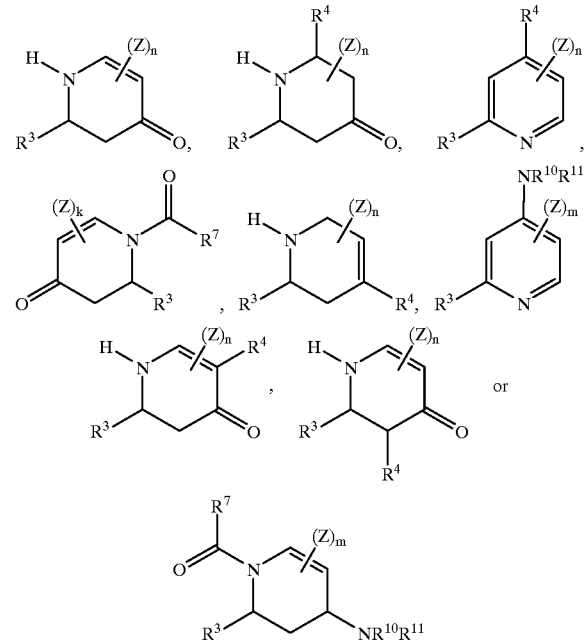

where $R^3$ is alkyl, alkenyl, alkynyl, aryl, arylalkyl, heteroaryl or heteroarylalkyl; $R^4$ is selected from hydrogen, alkyl, aryl, heteroaryl, arylalkyl, heteroarylalkyl, halo, amino, azido, cyano, nitro, alkylcarbonyl, arylcarbonyl, heteroarylcarbonyl, arylalkylcarbonyl, heteroarylalkylcarbonyl, carboxy, alkoxycarbonyl, aryloxycarbonyl, heteroaryloxycarbonyl, arylalkoxycarbonyl, heteroarylalkoxycarbonyl, thio, alkylthio and arylthio; each Z is indpendently selected from suitable groups, which include halogen, nitrile, nitro, formyl, alkyl, haloalkyl, polyhaloalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, dialkylaminoalkyl, diarylaminoalkyl, dialkylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl; k is 0–3, m is 0–2 and n is 0–3; $R^7$ is alkyl, aryl, heteroaryl, arylalkyl, heteroarylalkyl, alkoxy, aryloxy, arylalkoxy or heteroarylalkoxy; and $R^{10}$ and $R^{11}$ are each independently hydrogen, alkyl, aryl, heteroaryl, arylalkyl or heteroarylalkyl, or together form alkylene or alkenylene.

In preferred embodiments, k, m and n are 0, and the compounds have the formulae:

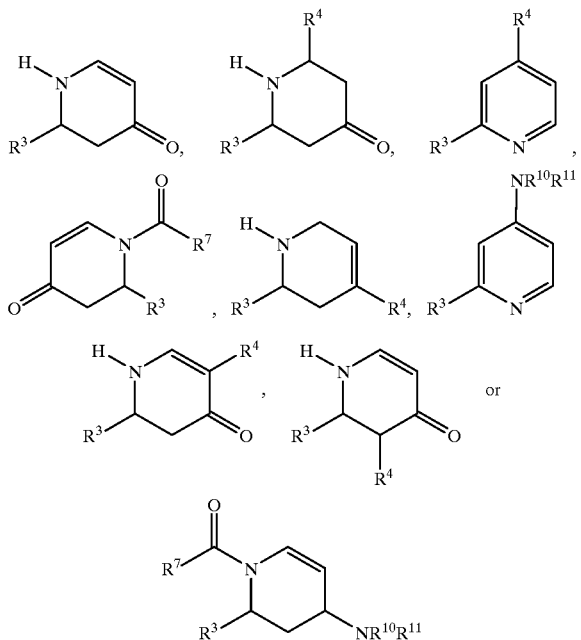

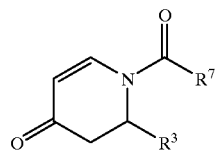

where R³ is alkyl, alkenyl, alkynyl, aryl or arylalkyl; R⁴ is selected from alkyl, aryl, heteroaryl, arylalkyl, heteroarylalkyl, halo, amino, azido, cyano, nitro, alkylcarbonyl, arylcarbonyl, heteroarylcarbonyl, arylalkylcarbonyl, heteroarylalkylcarbonyl, carboxy, alkoxycarbonyl, aryloxycarbonyl, heteroaryloxycarbonyl, arylalkoxycarbonyl, heteroarylalkoxycarbonyl, thio, alkylthio and arylthio; R⁷ is alkoxy, aryloxy or arylalkoxy; and R¹⁰ and R¹¹ are each independently hydrogen, alkyl, aryl, heteroaryl, arylalkyl or heteroarylalkyl, or together form alkylene or alkenylene.

In more preferred embodiments, the compounds have the formulae:

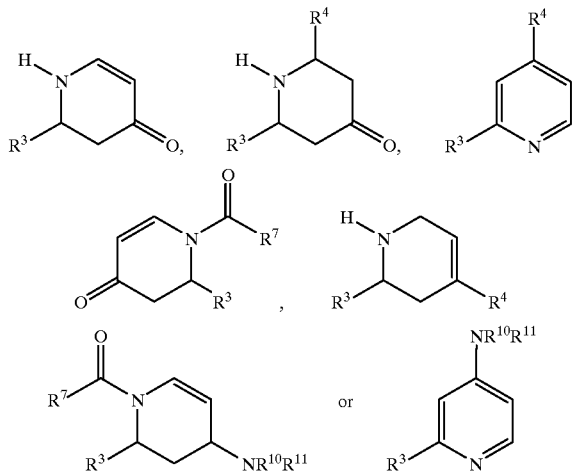

where R³ is alkyl, alkenyl, alkynyl, aryl or arylalkyl; R⁴ is selected from alkyl, aryl, heteroaryl, arylalkyl or heteroarylalkyl; R⁷ is alkoxy, aryloxy or arylalkoxy; and R¹⁰ and R¹¹ are each independently hydrogen, alkyl, aryl, heteroaryl, arylalkyl or heteroarylalkyl, or together form alkylene or alkenylene.

Compounds of particular interest herein include those of formula:

where R³ is alkyl, alkenyl, alkynyl, aryl or arylalkyl and R⁷ is alkoxy, aryloxy or arylalkoxy.

Also of interest are any pharmaceutically-acceptable derivatives, including salts, esters, acids, bases, solvates, hydrates and prodrugs of the compounds contained in the libraries provided herein. Such derivatives may be readily prepared by methods known to those of ordinary skill in the art. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl) aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

D. Libraries Prepared Using Resin Activation/Capture Approach Methods

Libraries of compounds for use in the discovery of new therapeutic agents are provided. The libraries may be prepared by any of the methods provided herein or by other methods known to those of skill in the art. The methods provided herein efficient for generating these diverse libraries. The libraries contain dihydropyridones, N-acyidihydropyridones, tetrahydropyridones, pyridines, aminopyridines, N-acyltetrahydropyridines or tetrahydropyridines. The libraries are collections of a plurality, two or more, preferably 10 to 100 up to 10⁶ or more, of compounds that have the formulae:

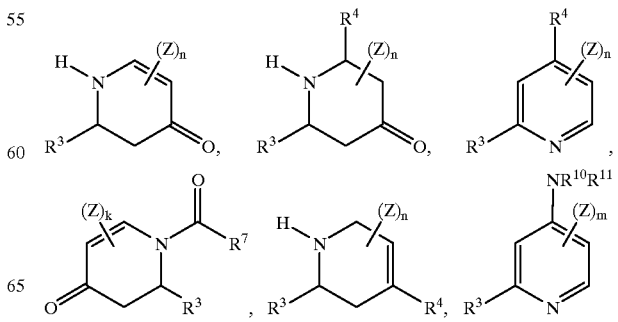

-continued

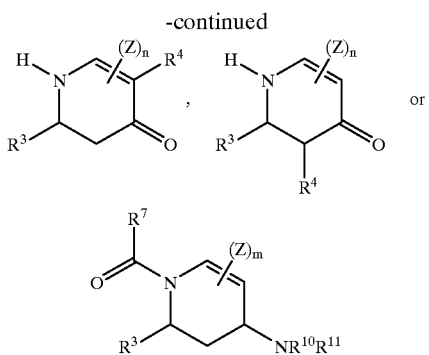

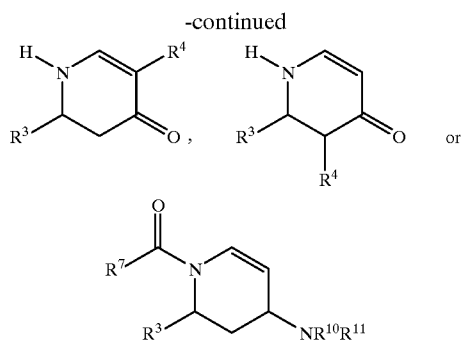

where $R^3$ is alkyl, alkenyl, alkynyl, aryl, arylalkyl, heteroaryl or heteroarylalkyl; $R^4$ is selected from hydrogen, alkyl, aryl, heteroaryl, arylalkyl, heteroarylalkyl, halo, amino, azido, cyano, nitro, alkylcarbonyl, arylcarbonyl, heteroarylcarbonyl, arylalkylcarbonyl, heteroarylalkylcarbonyl, carboxy, alkoxycarbonyl, aryloxycarbonyl, heteroaryloxycarbonyl, arylalkoxycarbonyl, heteroarylalkoxycarbonyl, thio, alkylthio and arylthio; each Z is indpendently selected from suitable groups, which include halogen, nitrile, nitro, formyl, alkyl, haloalkyl, polyhaloalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, dialkylaminoalkyl, diarylaminoalkyl, dialkylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl; k is 0–3, m is 0–2 and n is 0–3; $R^7$ is alkyl, aryl, heteroaryl, arylalkyl, heteroarylalkyl, alkoxy, aryloxy, arylalkoxy or heteroarylalkoxy; and $R^{10}$ and $R^{11}$ are each independently hydrogen, alkyl, aryl, heteroaryl, arylalkyl or heteroarylalkyl, or together form alkylene or alkenylene.

In preferred embodiments, k, m and n are 0, and the libraries contain compounds that have the formulae:

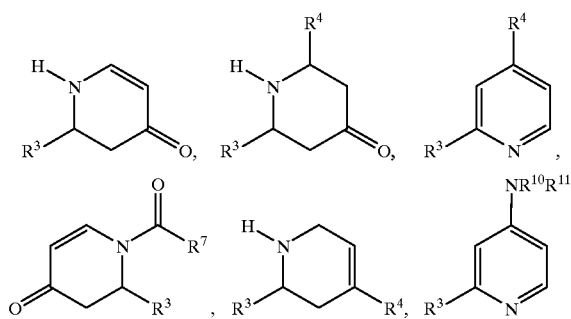

where $R^3$ is alkyl, alkenyl, alkynyl, aryl or arylalkyl; $R^4$ is selected from alkyl, aryl, heteroaryl, arylalkyl, heteroarylalkyl, halo, amino, azido, cyano, nitro, alkylcarbonyl, arylcarbonyl, heteroarylcarbonyl, arylalkylcarbonyl, heteroarylalkylcarbonyl, carboxy, alkoxycarbonyl, aryloxycarbonyl, heteroaryloxycarbonyl, arylalkoxycarbonyl, heteroarylalkoxycarbonyl, thio, alkylthio and arylthio; $R^7$ is alkoxy, aryloxy or arylalkoxy; and $R^{10}$ and $R^{11}$ are each independently hydrogen, alkyl, aryl, heteroaryl, arylalkyl or heteroarylalkyl, or together form alkylene or alkenylene.

In more preferred embodiments, the libraries contain compounds that have the formulae:

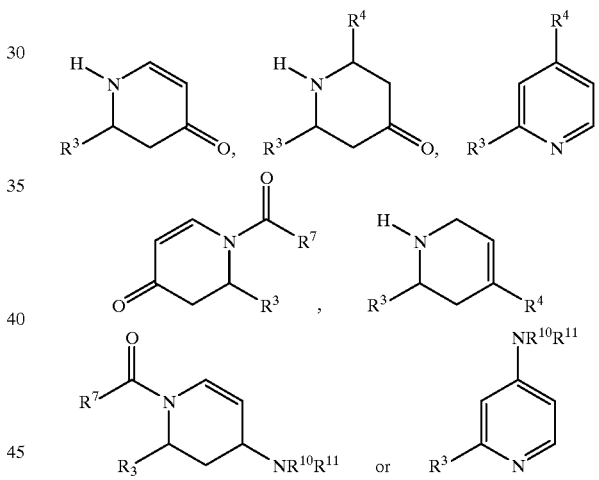

where $R^3$ is alkyl, alkenyl, alkynyl, aryl or arylalkyl; $R^4$ is selected from alkyl, aryl, heteroaryl, arylalkyl or heteroarylalkyl; $R^7$ is alkoxy, aryloxy or arylalkoxy; and $R^{10}$ and $R^{11}$ are each independently hydrogen, alkyl, aryl, heteroaryl, arylalkyl or heteroarylalkyl, or together form alkylene or alkenylene.

Libraries of particular interest herein include those the contain compounds of formula:

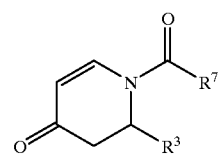

where $R^3$ is alkyl, alkenyl, alkynyl, aryl or arylalkyl and $R^7$ is alkoxy, aryloxy or arylalkoxy.

The libraries herein contain compounds that were heretofore difficult, if not impossible, to synthesize in a solid phase format. They thus provide collections of compounds for screening for any selected disorder or target. Diverse collections of molecules, particularly collections are not found in nature or that have not been synthesized by solid phase protocols are very desirable as a new source of diversity. Optimal use of high throughput screening protocols requires new sources of diverse collections of compounds.

The libraries or compounds provided herein may be screened in any assay or model system that are known in the art for the discovery of compounds which are useful as therapeutic agents. In particular, the libraries contain candidate neurologically active compounds as well as candidate anti-inflammatories and candidate antibiotics. The libraries can be screened using assays that identify compounds that are useful for the prevention or treatment of neurological disorders, such as schizophrenia, Alzheimer's disease, disorders of extrapyramidal motor function, such as Parkinson's disease, progressive supramuscular palsy, Huntington's disease, Gilles de la Tourette syndrome and tardive dyskinesia, obesity, severe pain, drug and tobacco withdrawal, respiration, mood and emotional disorders such as depression, anxiety and psychosis, motor control and function, focus and attention disorders, concentration disorders, memory loss, cognitive impairment, dementia (including AIDS dementia), neurodegenerative disorders, epilepsy, cardiovascular dysfunction including hypertension and cardiac arrhythmias, convulsive disorders, eating disorders, including bulimia and anorexia, autonomic disorders including dysfunction of gastrointestinal motility and function such as inflammatory bowel disease, irritable bowel syndrome, diarrhea, constipation, gastric acid secretion and ulcers, comedication in surgical procedures and pheochromocytoma; or heart insufficiency, hyperprolactinemia, bacterial infections, asthma or arthritis are provided. Such assays are well known in the art. See, e.g., U.S. Pat. Nos. 5,670,113, 5,610,196, 5,594,011, 5,567,710, 5,585,388, 5,521,297, 5,436,128, 5,401,629, 5,369,028, 5,391,492, 5,192,742, 4,431,809, 4,304,856, 4,283,390, 4,227,002, 3,856,937 and 3,338,786; International PCT application No. WO94/29449; and co-pending U.S. patent application Ser. Nos. 08/229,150, 08/870,537, 08/434,511, 08/434,968, 08/700,636, 07/938,154, 08/467,574, 08/466,589, 08/487,596, 08/496,855, 08/480,474 and 08/231,193. These patents and patent applications are hereby incorporated by reference in their entirety. Preferred assays include those that identify compounds with affinity for receptors expressed in cells of the nervous system, such as, but not limited to: acetylcholine receptors, as well as assays that identify compounds having antibacterial activity. Exemplary assays follow.

E. Assays for Identifying Compounds

1. Assays for Identifying Compounds that Interact with Cell Surface Proteins

A variety of assays for use in identifying compounds that interact with cell surface proteins involved in physiological processes associated with diseases and disorders are known in the art. Cell surface proteins of particular interest include, but are not limited to, receptors and ion channels. Such proteins play a central role in regulating intracellular levels of various ions and chemicals, many of which are important for cell viability and function and which can also be involved in disease processes and/or the amelioration of pathological conditions.

For example, calcium, sodium and potassium channels, as well as nicotinic acetylcholine receptors, gamma-aminobutyric acid (GABA) receptors, and certain excitatory amino acid receptors (e.g., N-methyl-D-aspartate, or NMDA, receptors and kainate/AMPA receptors) are transmembrane channels that function to regulate the levels of ions within cells, and in particular "excitable" cells such as neurons and muscle cells. Compounds that bind to these cell surface proteins in such a way as to modulate the opening and closing of the associated channels can have a profound effect on cellular and physiological processes influenced by the movement and levels of intracellular ions. These processes include, for example, gene expression, neurotransmission, neurotransmitter release and muscle contraction. Such processes are integral to normal functioning, for example in learning, memory, and movement, and in pathological conditions such as Parkinson's disease, dementia, epileptiform seizures, and neurodegenerative disorders.

Other cell surface receptors that are not necessarily associated with an ion channel bind circulating peptides, such as growth factors, and other chemical moieties, such as hormones and amino acids, as the initiating step in the induction of numerous intracellular pathways. Receptors are classified on the basis of the particular type of pathway that is induced. Included among these classes of receptors are those that bind growth factors and have intrinsic tyrosine kinase activity and those that couple to effector proteins through guanine nucleotide binding regulatory proteins, which are referred to as G-protein coupled receptors. G-protein coupled receptors include muscarinic acetylcholine receptors, metabotropic glutamate receptors, dopamine receptors, substance K receptors, angiotensin receptors, $\alpha$- and $\beta$-adrenergic receptors and serotonin receptors and, by interacting with G-proteins, regulate the intracellular levels of specific second messengers such as cyclic AMP, cyclic GMP, diacylglycerol, inositol 1,4,5-triphosphate and calcium. Growth factor receptors include, for example, nerve growth factor receptors and heparin binding growth factor (HBGF) receptors, and, by binding to growth factors, transmit signals that alter gene expression and thereby modulate cell proliferation and differentiation.

Because cell surface proteins are integral elements in basic cellular mechanisms and communication processes that are in turn critical to the proper functioning of physiological systems, they are the target of a majority of therapies designed to treat serious disorders and diseases. The identification of agents that interact with cell surface proteins to modulate their activity is therefore key in the therapeutic intervention of many pathological conditions. Accordingly, the libraries provided herein may be screened in assays designed to detect interactions of compounds with specific cell surface proteins in order to identify compounds within the libraries that might be useful in the treatment of associated diseases and disorders.

In preferred assays for detecting interactions of compounds with specific cell surface proteins, the target proteins are present as functional cellular components in living cell systems. Thus, in these assays, the compounds are exposed to cell surface proteins in a native functioning environment such that any interaction between the compound and the cell surface protein will be similar to that which occurs in vivo. It is most preferred that the cell systems used in the assays express as few other cell surface proteins of the type that is targeted for interaction as possible. This type of system is particularly useful in the identification of compounds that are specific for the cell surface protein of interest.

Cells for use in the preferred assays for detecting interactions of compounds with specific cell surface proteins can be prepared by recombinant expression of nucleic acids encoding the cell surface proteins in a suitable host cell.

Many cells that may be genetically engineered to express a heterologous cell surface protein are known. Such cells include, but are not limited to, baby hamster kidney (BHK) cells (ATCC No. CCL10), mouse L cells (ATCC No. CCLI.3), DG44 cells [see, Chasin (1986) *Cell. Molec. Genet.* 12:555] human embryonic kidney (HEK) cells (ATCC No. CRL1573), Chinese hamster ovary (CHO) cells (ATCC Nos. CRL9618, CCL61, CRL9096), PC12 cells (ATCC No. CRL1721), COS-7 cells (ATCC No. CRL1651) and *Xenopus oocytes*. Preferred cells for heterologous cell surface protein expression are those that can be readily and efficiently transfected. Preferred cells include HEK 293 cells, such as those described in U.S. Pat. No. 5,024,939 and by Stillman et al. (1985) *Mol. Cell. Biol.* 5:2051–2060.

The genes encoding many of the mammalian, and in particular, human, cell surface proteins which are regarded as significant targets in the development of therapeutic compounds have been isolated; exemplary cell surface proteins are listed in the following table.

| CELL SURFACE PROTEIN | REFERENCE |
| --- | --- |
| Human M2 muscarinic receptor | GenBank accession #M16404 |
| Human M4 muscarinic receptor | GenBank accession #M16405 |
| Human M5 muscarinic receptor | Bonner et al. (1988) Neuron 1: 403–410 |
| Rat M3 muscarinic receptor | GenBank accession #M16407 |
| Human neuronal nicotinic acetylcholine receptor $\alpha_3$ and $\beta_2$ subunits | U.S. Pat. No. 5,369,028 |
| Human neuronal nicotinic acetylcholine receptor $\alpha_2$ subunit | PCT Application Publication No. WO95/13299 |
| Human neuronal nicotinic acetylcholine receptor $\alpha_4$, $\alpha_7$ and $\beta_4$ subunits | PCT Application No. US94/02447 |
| Human neuronal nicotinic acetylcholine receptor $\alpha_6$ and $\beta_3$ subunits | PCT Application Publication No. US96/09775 |
| Human neuronal nicotinic acetylcholine receptor $\alpha_5$ subunit | Chini et al. (1992) Proc. Natl. Acad. Sci. U.S.A. 89:1572–1576 |
| Rat neuronal nicotinic acetylcholine receptor $\alpha_2$ subunit | Wada et al. (1988) Science 240: 330–334 |
| Rat neuronal nicotinic acetylcholine receptor $\alpha_3$ subunit | Boulter et al. (1986) Nature 319: 368–374 |
| Rat neuronal nicotinic acetylcholine receptor $\alpha_4$ subunit | Goldman et al. (1987) Cell 48: 965–973) |
| Rat neuronal nicotinic acetylcholine receptor $\alpha_5$ subunit | Boulter et al. (1990) J. Biol. Chem. 265:4472–4482 |
| Rat neuronal nicotinic acetylcholine receptor $\beta_2$ subunit | Deneris et al. (1988) Neuron 1: 45–54 |
| Rat neuronal nicotinic acetylcholine receptor $\beta_3$ subunit | Deneris et al. (1989) J. Biol. Chem. 264:6268–6272 |
| Rat neuronal nicotinic acetylcholine receptor $\beta_4$ subunit | Duvoisin et al. (1989) Neuron 3: 487–496 |
| Bovine GABA receptor $\alpha_1$ and $\beta_1$, subunits | Schofield et al. (1987) Nature 328:221–227 |
| Bovine GABA $\alpha_2$ and $\alpha_3$ subunits | Levitan et al. (1988) Nature 335: 76–79 |
| GABA receptor $\beta_2$ and $\beta_3$ subunits | Ymer et al. (1989) EMBO J. 8: 1665–1670 |
| GABA receptor $\delta$ subunit | Shivers (1989) Neuron 3:327–337 |
| Human metabotropic glutamate mGluR1, mGluR3 and mGluR5 receptors | PCT Application Publication No. WO94/29449 |
| Rat metabotropic glutamate mGluR1 receptor | Houamed et al. (1991) Science 252:1318–1321 |
| Rat metabotropic glutamate mGluR2, mGluR3 and mGluR4 receptors | Tanabe et al. (1992) Neuron 8: 169–179 |
| Rat metabotropic glutamate mGluR5 receptor | Abe et al. (1992) J. Biol. Chem. 267:13361–13368 |
| Human NMDA receptor R1, R2A, R2B, R2C and R2D subunits | PCT Application Publication No. WO94/24284 |
| Rat NMDA receptor R1 subunit | Moriyoshi et al. (1991) Nature 354:31–37 and Sugihara et al. (1992) Biochem. Biophys. Res. Comm. 185:826–832) |
| Mouse NMDA receptor $\epsilon 1$ subunit | Meguro et al. (1992) Nature 357: 70–74 |
| Rat NMDA receptor R2A, R2B and R2C subunits | Monyer et al. (1992) Science 256:1217–1221 |
| Rat glutamate GluR1 receptor | Hollman et al. (1989) Nature 342: 643–648 |
| Rat glutamate GluR2 and GluR3 receptors | Boulter et al. (1990) Science 249:1033–1037 |
| Rat glutamate GluR4 receptor | Keinanen et al. (1990) Science 249:556–560 |
| Rat glutamate GluR5 receptor | Bettler et al. (1990) Neuron 5: 583–595 |
| Rat glutamate GluR6 receptor | Egebjerg et al. (1991) Nature 351:745–748 |
| Rat glutamate GluR7 receptor | Bettler et al. (1992) Neuron 8: 257–265 |
| Human adrenergic $\beta 1$ receptor | Frielle et al. (1987) Proc. Natl. Acad. Sci. 84:7920–7924 |
| Human adrenergic $\alpha 2$ receptor | Kobilka et al. (1987) Science 238:650–656 |
| Hamster adrenergic $\beta 2$ receptor | Dixon et al. (1986) Nature 321: 75–79 |
| Dopamine D2 receptor | Stormann et al. (1990) Molec. Pharm. 37:1–6 and U.S. Pat. No. 5,128,254 |
| Human NGF receptor | Johnson et al. (1986) Cell47:545–554 |
| Human 5HT1a serotonin receptor | Kobilka et al. (1987) Nature 329: 75–79 |
| Human 5HT1C serotonin receptor | U.S. Pat. No. 4,985,352 |
| Human 5HT1D serotonin receptor | U.S. Pat. No. 5,155,218 |
| Rat 5HT2 serotonin receptor | Julius et al. (1990) Proc. Natl. Acad. Sci. USA 87:928–932 |
| Rat 5HT1C serotonin receptor | Julius et al. (1988) Science 241: 558–564 |
| Human and rabbit calcium channel $\alpha_1$, $\alpha_2$, $\beta$ and $\gamma$-subunits | U.S. Pat. No. 5,407,820, U.S. Pat. No. 5,618,720, U.S. Pat. No. 5,429,921, U.S. Pat. No. 5,386,025, PCT Application Publication nos. WO94/04822 |
| Rabbit skeletal muscle calcium channel $\alpha_1$ subunit | Tanabe et al. (1987) Nature 328: 313–318 |
| Rabbit skeletal muscle calcium channel $\beta$ subunit | Ruth et al. (1989) Science 245: 1115–1118 |
| Rat brain BK2 potassium ion channel | McKinnon (1989) J. Biol Chem. 264:9230–8236 |
| Mouse brain BK1 potassium ion channel | Tempel et al. (1988) Nature 332: 837–839 |
| Rat brain sodium ion channels I and II | Noda et al. (1986) Nature 320: 188–192 |
| Rat brain sodium ion channel III | Kayano et al. (1988) FEBS Lett. 228:187–194 |
| Human sodium ion channel II | ATCC Accession Nos. 59742 and 59743 |
| Chloride ion channels | Thiemann et al. (1992) Nature 356:57–60 and Paulmichl et al. (1992) Nature 356:238–241 |

2. Assays for the Detection of Binding of Compounds to a Cell Surface Protein

Assays designed to detect binding of compounds to cell surface proteins are well known in the art. Such assays often are conducted in a competitive binding format in which binding of a test compound to a cell surface protein is detected by displacement of a labeled compound (or ligand) that is known to bind to the cell surface protein. The following are exemplary competitive binding assays described with reference to specific cell surface proteins.

a. Muscarinic Acetylcholine Receptor Binding Assays

Cells expressing muscarinic acetylcholine M1 receptors, or membranes prepared therefrom, may be incubated with a labeled compound known to bind to the receptors. An exemplary compound is the antagonist N-methylscopolamine (NMS). Cells are incubated with, for example, [³H]-NMS (e.g., 1.4 nM) in the absence or presence of library compounds. Unbound labeled ligand is separated from cell-bound label by filtration of the assay mixture through filters, which are then analyzed in a scintillation counter to detect the amount of bound ³H-NMS.

b. Nicotinic Acetylcholine Receptor Binding Assays

Cells expressing nicotinic acetylcholine receptors, or membranes, such as mammalian cerebral membranes, prepared therefrom, may be incubated with labeled known ligands, such as, for example, nicotine, cytisine, methylcarbamylcholine and quinuclidinyl benzilate, in the absence or presence of library compounds. For example, ³H-nicotine binding to rat cerebral membranes may be performed according to the method of Flyn and Mash [(1986). *J. Neurochem.* 47:1948]. Atropine may be added to the incubation buffer to block binding to muscarinic acetylcholine receptors. Unbound labeled ligand is separated from receptor bound labeled ligand by filtration through filters which are then analyzed in a scintillation counter to detect the amount of bound ³H-nicotine.

C. Metabotropic Glutamate Receptor Binding Assays

Cells expressing metabotropic glutamate receptors, or membranes, such as mammalian cerebral membranes, prepared therefrom, may be incubated with labeled known ligands. For example, ³H-glutamate binding to rat forebrain membranes may be performed according to the method described by Schoepp et al. [(1992) *Neurosci. Lett.* 145:100]. Assay buffer may contain NMDA, AMPA and kainate to block ³H-glutamate binding to ionotropic glutamate receptors. Unbound labeled ligand is separated from receptor bound labeled ligand by filtration through filters which are then analyzed in a scintillation counter to detect the amount of bound ³H-glutamate.

d. NMDA Receptor Binding Assays

Cells expressing metabotropic glutamate receptors, or membranes, such as mammalian cerebral membranes, prepared therefrom, may be incubated with labeled known ligands. For example, ³H-MK801 or ³H-CGP39653 binding to rat brain membranes may be performed according to the methods described by Wong et al. [(1986) *Proc. Natl. Acad. Sci. USA* 83:7104] and by Sills et al. [(1991) *Eur. J. Pharmacol.* 192:19], respectively. Buffy coat membranes for use in such assays may be prepared from rat brain cortices as described by Jones et al. [(1989) *J. Pharmacol. Meth.* 21:161].

3. Assays for the Detection of Changes in Intracellular Ion Levels Resulting from the Interaction of a Compound With a Cell Surface Protein A variety of assays are known in the art for monitoring changes in intracellular ion levels which are indicative of a functional interaction between a compound and a cell surface protein that, when activated, results in ion fluxes within cells. Such assays include, but are not limited to, electrophysiological measurement of transmembrane currents, measurement of labeled, e.g., radioactively labeled, ions in cells, and detection of ion-sensitive fluorescent indicators contained in cells. Exemplary ion flux detection assays may be described as follows.

a. Electrophysiological Measurement of Transmembrane Currents

Electrophysiological measurement of transmembrane currents in cells expressing ion channels formed by cell surface proteins may be used to assess the ability of a compound to potentiate, antagonize or otherwise modulate the magnitude and duration of the flow of ions through such channels. It is possible to screen for compounds that specifically interact with certain subtypes of ion channels by using multiple recombinant cell systems, each of which expresses only one of the variety of subtypes. Exemplary recombinant systems include mammalian cells transfected with various subtype-encoding cDNAs or Xenopus oocytes that have been injected with RNA transcripts of subtype-encoding cDNAs. The preparation and injection of oocytes may be conducted as described by Dascal (1987) in *Crit. Rev. Biochem.* 22:317–387).

1. Nicotinic Acetylcholine Receptors

The response of nAChR to a test compound can be assessed by a variety of electrophysiological techniques, including two-electrode voltage clamp and patch clamp methods. The cation-conducting channel intrinsic to the nAChR opens in response to nicotinic cholinergic agonists, permitting the flow of transmembrane current carried predominantly by sodium and potassium ions under physiological conditions. This current can be monitored directly by voltage clamp techniques. To screen for compounds that specifically interact with certain subtypes of nAChR, such as an $\alpha2\beta2$ subtype or an $\alpha3\beta2$ subtype, multiple recombinant cell systems, each of which expresses only one of a variety of subtypes of nAChR, may be used. Thus, for example, in assays using injected oocytes, two-to-six days following mRNA injection, the oocytes may be examined using the two-electrode voltage clamp technique. Typically, the cells are bathed in Ringer's solution (115 mM NaCl, 2.5 mM KCl, 1.8 mM $CaCl_2$, 10 mM HEPES, pH 7.3) containing 1 μM atropine and voltage-clamped at −80 mV. Test compounds can be applied to the cells which are then analyzed for the presence of nAChR currents. The response to test compound may be compared to that of known nAChR agonists such as acetylcholine (ACh), nicotine, 1,1-dimethyl-4-phenylpiperazinium (DMPP) and cytisine. The compounds may also be screened to identify antagonists and potentiators of nAChR by adding a known agonist to the cells along with the test compound.

2. NMDA Receptors

Similarly, cells expressing NMDA receptor subunits, alone or in combination, e.g., NMDAR1 and NMDAR2 subunits, may be analyzed for transmembrane cation currents in response to exposure to library compounds. For example, Xenopus oocytes may be injected with in vitro transcripts prepared [such as by using the mCAP RNA Capping Kit (Cat. #200350, Stratagene, Inc., La Jolla, Calif.)] from constructs containing DNA encoding NMDA receptor NMDAR1 and NMDAR2 subunits. A typical amount of transcript injected into oocytes for such purposes is 12.5–50 ng of one or more NMDA receptor subunit transcripts per oocyte. Electrophysiological measurements of the oocyte transmembrane currents can be made using the two-electrode voltage clamp technique (see e.g., Stuhmer (1992) *Meth. Enzymol.* 207:319–339).

Typically, two-to-six days following mRNA injection, the oocytes are examined using the two-electrode voltage clamp technique. For example, the cells may be bathed in Ringer's solution (115 mM NaCl, 2.5 mM KCl, 1.8 mM $CaCl_2$, 10 mM HEPES, pH 7.3), and the membrane potential clamped at −80 to −100 mV. Compounds are applied by pipetting aliquots (e.g., 6.0 μl) of compound-containing solution directly into the bath, or by using gravity-feed into a Warner Instruments chamber (volume=110 μl) at a flow rate of 8 ml/min.

The response of the cells to compounds may be compared to the response elicited by exposing the cell to known NMDA receptor agonists, e.g., 10–30 μM glycine (gly) and 10–1001 μM glutamate (glu) or 100–1000 μM NMDA. To identify compounds that are antagonists of NMDA receptors, a current response was observed, the compounds are applied with a known NMDA receptor agonist. If the agonist current is blocked, the compound may be an antagonist. The degree of current block may be compared to that effected by known NMDA receptor antagonists [e.g., 0.1–1.0 mM $MgCl_2$ or 1 µM MK801 (Research Biochemicals, Inc., Natick, Mass.)].

3. Calcium Channels

The response of calcium channels to library compounds may be assessed by evaluating the amount and duration of the flow of calcium-selective ions through cells that express calcium channels as measured by electrophysiological recordings using two electrode or whole-cell patch clamp techniques. To identify compounds that are specific for certain subtypes of calcium channels, the cells used in the assay may be recombinant cells containing DNA encoding one or more of the various subunits known to comprise voltage-gated calcium channels. In order to improve the sensitivity of the assays, known methods can be used to eliminate or reduce non-calcium currents and calcium currents resulting from any endogenous calcium channels, when measuring calcium currents through recombinant channels. For example, the dihydropyridine Bay K 8644 specifically enhances L-type calcium channel function by increasing the duration of the open state of the channels [see, e.g., Hess, J. B., et al. (1984) Nature 311:538–544]. Prolonged opening of the channels results in calcium currents of increased magnitude and duration. Tail currents can be observed upon repolarization of the cell membrane after activation of ion channels by a depolarizing voltage command. The opened channels require a finite time to close or "deactivate" upon repolarization, and the current that flows through the channels during this period is referred to as a tail current. Because Bay K 8644 prolongs opening events in calcium channels, it tends to prolong these tail currents and make them more pronounced.

In practicing these assays, stably or transiently transfected cells or injected cells that express voltage-dependent human calcium channels containing one or more of the subunits of a human calcium channel desirably may be used in assays to identify agents, such as calcium channel agonists and antagonists, that modulate calcium channel activity. Functionally testing the activity of library compounds for calcium channel-modulating activity to determine if the compounds potentiate, inhibit or otherwise alter the flow of calcium ions or other ions through a calcium channel can be accomplished by (a) maintaining a eukaryotic cell which is transfected or injected to express a heterologous functional calcium channel capable of regulating the flow of calcium channel-selective ions into the cell in a medium containing calcium channel-selective ions (i) in the presence of and (ii) in the absence of a test compound; (b) maintaining the cell under conditions such that the heterologous calcium channels are substantially closed and endogenous calcium channels of the cell are substantially inhibited (c) depolarizing the membrane of the cell maintained in step (b) to an extent and for an amount of time sufficient to cause (preferably, substantially only) the heterologous calcium channels to become permeable to the calcium channel-selective ions; and (d) comparing the amount and duration of current flow into the cell in the presence of the test compound to that of the current flow into the cell, or a substantially similar cell, in the absence of the test compound.

For example, transiently transfected mammalian cells may be assayed for the presence of voltage-dependent barium currents using the whole-cell variant of the patch clamp technique [Hamill et al. (1981). Pflugers Arch. 391:85–100]. The cells may be placed in a bathing solution that contains barium ions to serve as the current carrier. Choline chloride, instead of NaCl or KCl, may be used as the major salt component of the bath solution to eliminate currents through sodium and potassium channels. The bathing solution, which may contain 1 mM $MgCl_2$ may be buffered at pH 7.3 with 10 mM HEPES (pH adjusted with sodium or tetraethylammonium hydroxide). The solution used to fill patch pipettes can be, for example, one containing 135 mM CsCl, 1 mM $MgCl_2$, 10 mM glucose, 10 mM EGTA, 4 mM ATP and 10 mM HEPES (pH adjusted to 7.3 with tetraethylammonium hydroxide)]. Cesium and tetraethylammonium ions block most types of potassium channels.

One method of applying compounds to the cells is to utilize "puffer" pipettes positioned within several micrometers of the cell, which apply solutions by pressure application. The compounds can be dissolved in a solution identical to the bathing solution. Known potentiators of calcium channels can also be applied to the cells, e.g., a 10 mM stock solution of Bay K 8644 (RBI, Natick, Mass.) prepared in DMSO and diluted to a final concentration of 1 µM in 15 mM $Ba^{2+}$-containing bath solution.

In these assays, the holding potential of the membrane can be set to, for example, −90 mV. The cell membrane is depolarized in a series of voltage steps to different test potentials and the current in the presence and absence of compounds and/or known modulators, e.g., 1 µM Bay K 8644, is recorded. A comparison of the I-V curves, generated by plotting the largest current recorded after each depolarization versus the depolarization voltage, corresponding to recordings conducted in the absence and presence of compound can be employed to illustrate the effect of compounds on the voltage-activated current. Characteristics of voltage-activated calcium channel currents that may be affected by modulators of these channels include typical current magnitude and activation voltage profiles.

*Xenopus laevis* oocytes may also be used as the host cells for recombinant expression of calcium channels to be evaluated in assays to screen compounds for calcium channel-modulating activity. In assays, oocytes are isolated and defolliculated by collagenase treatment and maintained in 100 mM NaCl, 2 mM KCl, 1.8 mM $CaCl_2$, 1 mM $MgCl_2$, 5 mM HEPES, pH 7.6, 20 µg/ml ampicillin and 25 µg/ml streptomycin at 19–25° C. for 2 to 5 days after injection and prior to recording. RNA transcripts are produced from calcium channel subunit-encoding cDNAs, and, typically, 6 ng of the specific mRNA may be injected per cell in a total volume of 50 nl. Injected obcytes may be examined for voltage-dependent barium currents using two-electrode voltage clamp methods [Dascal, N. (1987) CRC Crit. Rev. Biochem. 22:317] and a bath solution containing the following: 40 mM $BaCl_2$, 36 mM tetraethylammonium chloride (TEA-Cl), 2 mM KCl, 5 mM 4-aminopyridine, 0.15 mM niflumic acid, 5 mM HEPES, pH 7.6. Oocytes injected with calcium channel subunit-encoding transcripts are exposed to library compounds and analyzed for the effect, if any, on inward barium currents upon depolarization of the membrane from a holding potential of, for example, −90 mV or −50 mV.

4. Metabotropic Glutamate Receptors

Although metabotropic glutamate receptors are not directly involved in the formation of an ion channel, activation of these receptors results in an interaction of the receptor with G-proteins in cells that thereby causes changes in intracellular second messenger (e.g., cAMP, cGMP, inositol 1,4,5-triphosphate ($IP_3$) and calcium) levels which can ultimately result in the flux of ions through other cell surface transmembrane ion channels. Accordingly, it is possible to screen compounds for metabotropic receptor-modulating activity by electrophysiological measurement of transmembrane currents in cells expressing metabotropic receptors.

Cell systems for use in assays to screen compounds for functional interaction with metabotropic receptors preferably contain G-proteins. One suitable cell system for use in such assays is the Xenopus oocyte. In oocytes, induction of a G-protein coupled $IP_3$ generation pathway results in release of calcium from internal stores which in turn can activate a chloride channel that can be detected as a delayed oscillatory current in voltage-clamp recordings of the cells.

In order to identify compounds that are specific for a certain type of metabotropic receptor, multiple recombinant oocyte systems, each of which expresses a different metabotropic receptor subtype, can be utilized. Recombinant capped transcripts of metabotropic receptor cDNAs are injected into oocytes (typically 10–50 ng of transcript per oocyte) which are then examined using the two-electrode voltage clamp technique (see e.g., Stuhmer (1992) *Meth. Enzymol.* 207:319–339). The cells may be bathed in Ringer's solution (as described above for examination of oocytes expressing NMDA receptor subunits), and the membrane potential of the cells may be clamped at −80 to −100 mV. Compounds can be applied to the bath by pipetting aliquots (e.g., 60 $\mu l$) of compound-containing solution directly into the bath, and any current resulting after addition of compounds is recorded. The response of the cells to application of compounds may be compared to the current induced upon addition of known metabotropic receptor-modulating compounds [e.g., 0.001–0.1 $\mu M$ quisqulate, 0.1–10.0 $\mu M$ glutamate and 0.1–300 $\mu M$ 1S,3R-ACPD (1-aminocyclopentyl-1,3-dicarboxylic acid)].

b. Ion-sensitive Fluorescent Indicator Assays

Activation of ion channels and other cell surface proteins that induce changes in intracellular second messenger levels can result in changes in ion concentrations in cells. These changes are often rapid and transient in nature. Therefore, methods of detecting transient changes in intracellular ion concentration can be utilized in assays to screen for compounds that functionally interact with ion channels and other cell surface proteins. One method for measuring intracellular ion levels relies on ion-sensitive fluorescent indicators.

In assays to identify compounds that interact with cell surface proteins that, when activated, cause a change in the intracellular concentration of certain ions, the cytoplasm of the cells employed are loaded with a fluorescent indicator which is sufficiently sensitive to the ions. If the cell surface protein is an ion channel that allows flow of ions across the cell membrane, any change in intracellular ion concentration that results from the ion flux induced by binding of a compound to the ion channel can be detected as a change in fluorescence intensity. Such direct assays may be performed to assay, for example, cells loaded with a calcium-sensitive fluorescent indicator and having receptors and/or ion channels that are permeable to calcium (e.g., calcium channels or N-methyl-D-aspartate (NMDA) receptors), cells loaded with a chloride-sensitive fluorescent indicator and having receptors which are permeable to chloride ions (e.g., GABA receptors), cells loaded with a sodium- or potassium-sensitive fluorescent indicator and having receptors which are permeable to sodium and/or potassium ions (e.g., kainate/AMPA receptors, nicotinic acetylcholine receptors, sodium channels or potassium channels), and so forth.

Additionally, the interaction of compounds with receptors which are ligand-gated ion channels may be detected in a type of "indirect" assay which is based on a characteristic depolarization caused by the passage of ions through ligand-gated ion channels. For example, such indirect assays can employ cells having voltage-dependent calcium channels and the ligand-gated ion channels of interest. Activation of the ligand-gated ion channel allows ions (not calcium ions) to flow through the channel, depolarizing the cell membrane which in turn activates voltage-dependent calcium channels and results in the flow of calcium ions into the cytoplasm. The cytoplasm of the cells is loaded with a calcium-sensitive indicator. For example, activation of the nicotinic acetylcholine receptors results in an influx of sodium ions, depolarizing the cell membrane and, consequently, activating voltage-dependent calcium channels. The degree of activation of the nicotinic receptors is measured indirectly by the flow of calcium ions through activated calcium channels. Among the known ligand-gated ion channels that could be assayed in this manner are certain kainate/AMPA-type excitatory amino acid (EAA) receptors.

In assays to identify compounds that interact with cell surface receptors which, when activated, initiate subsequent intracellular events, such as changes in second messenger levels, ion-sensitive fluorescent indicators can be used to detect ion concentration changes associated with the change in second messenger levels. Activation of some G-protein-coupled receptors stimulates the formation of inositol triphosphate ($IP_3$, a G-protein-coupled receptor second messenger) through phospholipase C-mediated hydrolysis of phosphatidylinositol. $IP_3$ in turn stimulates the release of intracellular calcium ion stores. Thus, a change in cytoplasmic calcium ion levels caused by release of calcium ions from intracellular stores is used to reliably determine G-protein-coupled receptor activation by an added compound. Cells expressing such G-protein-coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Fluorescence-based assays may also be used to identify interaction of compounds with receptors which, when activated, result in a change in the level of intracellular cyclic nucleotides, e.g., cAMP, cGMP. For example, activation of some dopamine, serotonin, metabotropic glutamate receptors and muscarinic acetylcholine receptors results in a decrease in the cAMP or cGMP levels of the cytoplasm. This change in cyclic nucleotide levels can in turn cause a change in the permeability of certain ion channels which will result in an ion concentration change in cells that is detectable by an ion-sensitive fluorescent indicator. Exemplary cyclic nucleotide-gated ion channels include rod photoreceptor cell channels and olfactory neuron channels [see, Altenhofen, W. et al. (1991) *Proc. Natl. Acad. Sci U.S.A.* 88:9868–9872 and Dhallan et al. (1990) *Nature* 347:184–187] that are permeable to cations upon activation by binding of cAMP or cGMP. The cell system used in these assays expresses not only the receptor of interest that, when activated, causes a change in intracellular cyclic nucleotide levels, but also a cyclic nucleotide-gated ion channel (e.g., photoreceptor or olfactory neuron channels). A change in cytoplasmic ion levels caused by a change in the amount of cyclic nucleotide activation of photo-receptor or olfactory neuron channels is used to detect a functional interaction between compounds and receptors that cause a change in cAMP or cGMP levels when activated. In cases where activation of the receptor results in a decrease in cyclic nucleotide levels, it may be preferable to expose the cells to agents that increase intracellular cyclic nucleotide levels, e.g., forskolin, prior to adding a compound to the cells in the assay. Cell for this type of assay can be made by co-transfection of a host cell with DNA encoding a cyclic nucleotide-gated ion channel and DNA encoding a receptor (e.g., certain metabotropic glutamate receptors, muscarinic acetylcholine receptors, dopamine receptors, serotonin receptors and the like) which, when activated, causes a change in cyclic nucleotide levels in the cytoplasm.

An automated fluorescence detection system for use in any of the ion-sensitive fluorescent indicator-based assays described above has been described in U.S. Pat. No. 5,670,113 and corresponding PCT Patent Application No. US92/11090. This system provides a highly efficient method of screening compounds for interaction with cell surface proteins. The system may be used with a 96-well plate in which the sample wells contain receptor- and/or ion channel-expressing cells. Where the compound is tested for putative agonist (a compound that activates the receptor or ion channel) activity, it may be delivered to the wells via a reagent-adding device; where the compound is tested for activity as an antagonist or potentiator (that is, an agonist-like compound which augments agonist activity, but cannot itself cause activation, such as the calcium channel potentiator, Bay K8644) the compound may be (1) included in the well(s) before the plate is introduced into the apparatus, (2) added by the reagent-adding device along with addition of an agonist reagent used to activate the receptors or ion channels, or (3) added by the movable reagent-adding device prior to addition of the agonist (i.e., sequential addition of reagents). Because many cells can be assayed in a relatively short period of time, this assay enables rapid analysis of replicate samples, including control samples, and provides a possibility for screening multiple compounds and/or multiple doses of compounds in a single operation. Further, because single or sequential additions of compounds can be made without moving the plate, fluorescence changes caused by the addition of a wide variety of known or unknown compounds may be measured, which greatly enhances the ability of the assays to rapidly identify compounds having agonist, antagonist or potentiating activity.

1. Nicotinic Acetylcholine Receptors

Activation of ligand-gated nicotinic AChR by agonists leads to an influx of cations, including $Ca^{++}$, through the receptor channel. $Ca^{++}$ entry into the cell through the channel can induce release of calcium contained in intracellular stores. Monovalent cation entry into the cell through the channel can also result in an increase in cytoplasmic $Ca^{++}$ levels through depolarization of the membrane and subsequent activation of voltage-dependent calcium channels. Therefore, methods of detecting transient increases in intracellular calcium concentration can be applied to the analysis of functional nicotinic AChR expression. One method for measuring intracellular calcium levels relies on calcium-sensitive fluorescent indicators.

Calcium-sensitive indicators, such as fluo-3 (Catalog No. F-1241, Molecular Probes, Inc., Eugene, Oreg.), are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular $Ca^{2+}$ concentration of cells containing the indicator can be expressed directly as an increase in fluorescence.

In an exemplary assay, cells expressing nAChR are plated in the wells of a 96-well microtiter dish and loaded with fluo-3 by incubation for 2 hours at 20° C. in a medium containing 20$\mu$M fluo-3, 0.2% Pluronic F-127 in HBS (125 mM NaCl, 5 mM KCl, 1.8 mM $CaCl_2$, 0.62 mM $MgSO_4$, 6 mM glucose, 20 mM HEPES, pH 7.4). The cells are then washed with assay buffer (e.g., HBS). The antagonist d-tubocurarine can be added to some of the wells at a final concentration of 10 $\mu$M. The microtiter dish is then placed into a fluorescence plate reader and the basal fluorescence of each well is measured and recorded before addition of compound to the wells. The fluorescence of the wells is monitored repeatedly during a period of approximately 60 seconds following addition of compound. Control wells can contain nAChR-expressing cells to which no compound or known agonist (e.g., 200 $\mu$M nicotine) is added. Control wells can also contain cells that do not express nAChR.

2. NMDA Receptors

Activation of ligand-gated NMDA receptors by agonists leads to an influx of cations (both monovalent and divalent), including $Ca^{2+}$, through the receptor channel. Calcium entry into the cell through the channel can in turn induce release of calcium contained in intracellular stores. Monovalent cation entry into the cell through the channel can also result in an increase in cytoplasmic calcium levels through depolarization of the membrane and subsequent activation of voltage-dependent calcium channels. Therefore, methods of detecting transient increases in intracellular calcium concentration can be applied to the analysis of compounds for functional interaction with NMDA receptors.

In an exemplary assay, cells that express NMDA receptors are plated in the wells of a 96-well microtiter dish (Nunc Catalog No. 1-6708, available through Alameda Industries, Escondido, Calif.) that has been precoated with poly-L-lysine at a density of 2.5×$10^5$ cells/well and loaded with fluo-3 by incubation for 2 hours at 20° C. in a medium containing 20 $\mu$M fluo-3, 0.2% Pluronic F-127 in HBS (125 mM NaCl, 5 mM KCl, 1.8 mM $CaCl_2$, 0.62 mM $MgCl_2$, 20 mM glucose, 20 mM HEPES, pH 7.4). The cells are then washed with assay buffer (e.g., HBS). The microtiter dish is then placed into a fluorescence plate reader (e.g., Fluoroskan II, Lab Products International, Ltd., Raleigh, N.C.) and the basal fluorescence of each well is measured and recorded before addition of compound to the wells. The fluorescence of the wells is monitored repeatedly (75 readings at 0.63-sec intervals) following addition of compound. Control wells can contain cells to which no compound has been added or to which a known NMDA receptor agonist (e.g., 10 $\mu$M glycine and 10 $\mu$M glutamate) has been added. Control wells can also contain cells that do not express NMDA receptors.

The resting potential of the membrane of some mammalian host cells may be relatively positive (e.g., −35 mV). Because activation of some NMDA receptors may be significantly reduced at relatively positive potentials, it may be necessary to lower the resting potential of the membrane of cells transfected with NMDA receptor subunit-encoding DNAs prior to assaying the cells for compounds that interact with NMDA receptors using the fluorescent indicator-based assay. This may be accomplished by adding valinomycin (~10 $\mu$M) to the transfected cells prior to adding compounds to initiate the assay.

3. Calcium Channels

Activation of voltage-gated calcium channels by membrane depolarization results in an influx of calcium ions into cells. Compounds that are agonists or antagonists of calcium channels alter the permeability of the channels. Therefore, methods of detecting transient increases in intracellular calcium concentration can be applied to the analysis of compounds for functional interaction with calcium channels.

Exemplary assays can be conducted essentially as described above except using cells that express calcium channels. In these assays, the calcium channels can be activated by addition of KCl (typically up to ~50 mM) to the wells to depolarize the cell membranes.

4. Metabotropic Glutamate Receptors

Activation of G-protein coupled metabotropic receptors leads to stimulation of the phosphatidylinositol (PI) hydrolysis/intracellular calcium signalling pathway and/or the inhibitory cAMP cascade. Methods of detecting transient increases in intracellular calcium concentration can be applied to the detection of compounds that functionally interact with metabotropic receptors that are coupled to the PI hydrolysis/calcium mobilization pathway or to both the PI hydrolysis/calcium mobilization pathway and the inhibitory cAMP cascade.

In an exemplary assay, cells that express metabotropic receptors are plated in the wells of a 96-well microtiter dish and treated essentially as described above for assays for compounds that interact with NMDA receptors. Control wells contain cells to which no compound is added or to which known metabotropic receptor-modulating compounds (e.g., quisqualate, glutamate, trans-ACPD (1-aminocyclopentane-1,3-dicarboxylic acid), AP3 (2-amino-3-phosphonopentanoate) and CNQX (6-cyano-7-nitroquinoxaline)) are added. Control wells may also contain cells that do not express metabotropic receptors.

C. Labeled Ion Flux Detection

The ability of compounds to mediate the influx of $^{88}$Rb into cells expressing ion channels (e.g., nicotinic acetylcholine receptors or nAChR) that are permeable to this ion is another means of screening compounds for interaction with such ion channels. An exemplary $^{86}$Rb ion-flux assay for compounds that interact with nAChR is conducted as follows:

1. The night before the experiment, cells expressing nAChR are plated at $2 \times 10^6$ per well (i.e., 2 ml per well) in a 6-well polylysine-coated plate.

2. The culture medium is decanted and the plate washed with 2 ml of assay buffer (50 mM HEPES, 260 mM sucrose, 5.4 mM KCl, 1.8 mM $CaCl_2$, 0.8 mM $MgSO_4$, 5.5. mM glucose) at room temperature.

3. The assay buffer is decanted and 1 ml of assay buffer, containing 3 $\mu$Ci/ml $^{86}$Rb, with 5 mM ouabain and compound is added.

4. The plate is incubated on ice at 1° C. for 4 min.

5. The buffer is decanted into a waste container and each well is washed with 3 ml of assay buffer, followed by two washes of 2 ml each.

6. The cells are lysed with $2 \times 0.5$ ml of 0.2% SDS per well and transferred to a scintillation vial containing 5 ml of scintillation fluid.

7. The radioactivity contained in each vial is measured and the data calculated. The presence of radioactivity in amounts greater than in a negative control indicates that the compound was able to activate nAChR present in the cells.

3. Assays for the Detection of Changes in Intracellular Second Messenger Systems Resulting from the Interaction of a Compound With a Cell Surface Protein Several additional assays are known in the art for detecting compounds that interact with cell proteins to cause a change in intracellular second messenger systems. Many of these assays may also be used in the detection of compounds that interact with ion channels to cause a change in intracellular ion levels. Exemplary assays are as follows.

a. Transcription-based Assay

In transcription-based assays, compounds that activate cell surface proteins are identified through the detection of the expression of a reporter gene that is contained within cells that also express the cell surface protein of interest. The expression of the reporter gene is induced by changes in intracellular second messengers and/or ion concentration changes in the cells as a result of activation of the cell surface protein. Thus, these assays utilize recombinant cells that express the cell surface protein and contain a reporter gene construct in which transcription of the reporter gene is under the control of promoter transcriptional control sequences whose activity is regulated by the cell surface protein.

The recombinant cells for use in the transcription-based assay may endogenously express the cell surface protein or may express heterologous DNA that encodes the cell surface protein. These methods compare the difference in the amount of transcription of a reporter gene in recombinant cells in the presence of the compound, with the amount of transcription in the absence of the compound, or with the amount of transcription in a control cell that does not express the cell surface protein. Exemplary cell surface proteins are any of the muscarinic receptors, nicotinic acetylcholine receptors, NMDA receptors, glutamate receptors, gamma-aminobutyric acid (GABA) receptors, receptors, adrenergic receptors, dopamine receptors, serotonin receptors, and calcium, sodium and potassium ion channels. Exemplary promoter region and transcriptional regulatory sequences are any of the c-fos gene promoter and the c-fos gene-derived transcriptional regulatory sequences of nucleotides, the vasoactive intestinal peptide (VIP) gene promoter, the somatostatin gene promoter, the proenkephalin promoter, the phosphoenolpyruvate carboxykinase gene promoter and the nerve growth factor-1 A gene promoter. The reporter genes are any of the genes encoding bacterial chloramphenicol acetyltransferase, firefly luciferase, bacterial luciferase, β-galactosidase and alkaline phosphatase; and other transcriptional regulatory elements, including cyclic adenosine monophosphate responsive elements, and elements responsive to intracellular calcium ion levels.

In practicing the assay, a reporter gene construct is inserted into an eukaryotic cell to produce a recombinant cell which has present on its surface a cell surface protein of interest. Methods for introducing heterologous DNA into eukaryotic cells are well known in the art and any such method may be used. The recombinant cell is contacted with a compound and the level of reporter gene expression is measured. The contacting may be effected in any vehicle and the testing may be by any means using any protocols, such as serial dilution, for assessing specific molecular interactions known to those of skill in the art.

After contacting the recombinant cell for a sufficient time to effect any interactions, the level of gene expression is measured. The amount of time to effect such interactions may be empirically determined, such as by running a time course and measuring the level of transcription as a function of time.

The amount of transcription may be measured using any method known to those of skill in the art to be suitable. For example, specific mRNA expression may be detected using Northern blots or specific protein product may be identified by a characteristic stain.

The amount of transcription is then compared to the amount of transcription in either the same cell in the absence of the compound or it may be compared with the amount of transcription in a substantially identical cell that lacks the specific receptors. A substantially identical cell may be derived from the same cells from which the recombinant cell was prepared but which had not been modified by introduction of heterologous DNA. Alternatively, it may be a cell in which the specific receptors are removed. Any statistically or otherwise significant difference in the amount of transcription indicates that the test compound has in some manner altered the activity of the specific receptor.

If the test compound does not appear to enhance, activate or induce the activity of the cell surface protein, the assay may be repeated and modified by the introduction of a step in which the recombinant cell is first tested for the ability of a known agonist or activator of the specific receptor to activate transcription. If the transcription is induced, the test compound is then be assayed for its ability to inhibit, block or otherwise affect the activity of the agonist.

b. Phosphatidylinositol Hydrolysis ($IP_1$) Assays

Because activation of G-protein-coupled receptors by agonists can lead to stimulation of the phosphatidylinositol (PI) hydrolysis pathway, methods of detecting increases in the products of PI hydrolysis (e.g., $IP_3$, $IP_2$ or $IP_1$) can be applied to the analysis of compounds for functional interaction with receptors (e.g., metabotropic glutamate receptors) that are coupled to the PI hydrolysis/calcium mobilization pathway or to both the PI hydrolysis/calcium mobilization pathway and the inhibitory cAMP cascade. One method for measuring $IP_1$, and/or $IP_2$ and/or $IP_3$ generated by hydrolysis of PI involves incorporation of [$^3$H]-myo-inositol into cell membrane phospholipids and subsequent separation of [$^3$H]-$IP_1$, [$^3$H]-$IP_2$ and [$^3$H]-$IP_3$, followed by quantitation of the radioactivity in each fraction. An exemplary method for conducting such measurements with specific reference to metabotropic receptor-expressing cells is as follows.

Cells that express recombinant human mGluR5 receptors are plated in 24-well microtiter plates to which 2 $\mu$Ci of [$^3$H]-myo-inositol (Amersham catalog #PT6-271, Arlington Heights, Ill.; specific activity=17.7 Ci/mmol) is added to each well and incubated overnight at 37° C. The next day media is then aspirated and the cells are washed twice with 0.5 ml Krebs bicarbonate buffer [117.9 mM NaCl, 4.72 mM KCl, 2.54 mM $CaCl_2$, 1.18 mM $MgSO_4$, 1.19 mM $KH_2PO_4$, 25 mM $NaHCO_3$, 11.1 mM dextrose (equilibrated with 95% $O_2$, 5% $CO_2$, pH 7.4)]. The cells are incubated for 45 min. at room temperature and the buffer is then aspirated from each well. The cells are then incubated for 20 min at 37° C. with 450 $\mu$l Krebs-bicarbonate buffer containing 10 mM LiCl instead of 10 mM NaCl (to block hydrolysis of $IP_1$ to inositol and inorganic phosphate) and 10 mM unlabeled myoinositol.

To begin treatment of the cells with compounds, 50 $\mu$l of Krebs-bicarbonate buffer (control) or 10×the final concentration of the compound is added to each well and the incubation is continued for 40 min. Incubation is terminated by addition of 1 ml ice-cold methanol to each well.

In order to isolate $IP_1$ from the cells, the cells are removed from the plates, and the cell suspension is transferred to 12×75 mm glass tubes. The tubes are thoroughly vortexed, and a 150-$\mu$l aliquot, i.e., one-tenth of the total volume, of each reaction mixture is transferred to another tube for protein determination. The water-soluble inositol phosphates are separated from the radiolabelled membrane phospholipids by extraction in 1 ml chloroform. The tubes are incubated at room temperature for 30 min before centrifugation at 500×g for 5 min at 4° C. The aqueous (top) layer containing the [$^3$H]-inositol phosphates is transferred to 10-ml syringes connected to Accell QMA SEP-PAK columns (Millipore; Calif.), which are attached to an Amersham Superseparator apparatus that is modified to allow collection into 20-ml scintillation vials. Water (10 ml) is added to the cartridge to remove [$^3$H]-inositol precursor, followed by 4 ml 0.02 M triethylammonium hydrogen carbonated buffer (TEAB, Fluka; N.Y.). To separately remove [$^3$H]-$IP_1$, [$^3$H]-$IP_2$ and [$^3$H]-$IP_3$ from the cartridge, 4 ml of 0.1 M TEAB, 4 ml of 0.3 M TEAB and 4 ml of 0.4 M TEAB are sequentially added to the cartridge and the separate eluate fractions are collected in large scintillation vials. Scintillation fluid is added to each vial for subsequent scintillation counting to determine the amount of each IP in the separate fractions. Protein concentration is also determined.

C. Cyclic AMP Assays

Because activation of some G-protein-coupled receptors results in decreases or increases in cAMP, assays that measure intracellular cAMP levels can also be used to identify compounds that interact with such receptors. In an exemplary assay, with specific reference to cells expressing recombinant human metabotropic receptors, cells are plated in 24-well microtiter plates and allowed to incubate overnight. The following day media is then aspirated and the cells are washed twice with 0.5 ml Krebs bicarbonate buffer (same buffer used in the PI hydrolysis assay as described above) containing 1 mM IBMX (3-isobutyl-1-methylxanthine) and 0.1% BSA. Each wash is followed with a 30-min incubation at 37° C. The buffer is aspirated from each well and the cells are then incubated for 20 min at 37° C. with 0.2 ml Krebs-bicarbonate buffer containing 1 mM IBMX and 0.1% BSA.

To begin treatment of the cells with compounds, 50 $\mu$l of Krebs-bicarbonate buffer with or without 5×the final concentration of forskolin is added to some of the cells (basal control) and 5×the final concentration of the compound plus 5×the final concentration of forskolin is added to some cells (test cells) and the incubation is continued for 15 min at 37° C. At the end of this 15-min period, the reaction is terminated by adding 25 $\mu$l of 1% Triton X-100 solution and the incubation is continued for another 10 min. The lysed cells plus the cell suspension are transferred to polypropylene tubes. Each well is rinsed with 75 $\mu$l of Krebs-bicarbonate buffer containing 1 mM IBMX and 0.1% BSA. The rinse is combined with the cell lysate. The cell lysate suspension is centrifuged at 2300×g for 5 min and the supernatant is assayed for cAMP levels using an RIA kit (Amersham Life Sciences catalog #TRK 432; Arlington Heights, Ill.).

4. Assays to Assess the Ability of Compounds to Influence Nervous System Activity Library compounds may also be screened in standard assays for the evaluation of activities associated with therapeutic agents used in treatment of nervous systems disorders. Exemplary assays are as follows.

a. $^3$H-Neurotransmitter Release Assays

Measurements of $^3$H-dopamine release from rat striatal slices may be performed according to the method of Sacaan et al. (*J. Neurochem.* 59:245 (1992)). Male Sprague-Dawley rats (250–300 g) are decapitated and the striata or olfactory tubercles dissected quickly on a cold glass surface. The tissue is chopped to a thickness of 300 $\mu$m with a McIlwain tissue chopper. After chopping again at right angles the tissue is dispersed and incubated for 10 min. at 37° C. in oxygenated Kreb's buffer. $^3$H-Dopamine (40 Ci/mmol, NEN-Dupont, Boston, Mass.) is added (50 nM) and the tissue incubated for 30 min. in Kreb's buffer containing 10

μM pargyline and 0.5 mM ascorbic acid. Aliquots of the minced tissue are transferred to chambers of a Brandel Superfusion system in which the tissue is supported on Whatman GF/B filter discs. The tissue is then superfused with buffer at a constant flow rate of 0.3 ml/min by means of a Brandel peristaltic pump. The perfusate is collected in plastic scintillation vials in 3-min fractions, and the radioactivity is estimated by scintillation spectrophotometry. The superfusate for the first 120 min is discarded. After two baseline fractions are collected, the superfusion buffer is switched to fresh buffer with or without compound of interest. At the end of the experiment the filter and the tissue are removed, and the radiolabeled neurotransmitter content is estimated after extraction into scintillation fluid. The fractional efflux of radiolabeled neurotransmitter is estimated as the amount of radioactivity in the perfusate fraction relative to the total amount in the tissue.

Following essentially the same procedure as set forth in the preceding paragraph, the amount of $^3$H-norepinephrine released from rat hippocampus, thalamus and prefrontal cortex slices superfused with buffer containing (or lacking) compounds of interest is also measured.

The results of studies of the effects of library compounds (as compared to the effect of a compound known to effect neurotransmitter release, e.g., nicotine) on the release of neurotransmitters from rat brain slices may be compared to evaluate whether a compound selectively induces release of catecholamines in different brain regions.

b. Locomotor Activity Assays

The effects of compounds on locomotor activity of rats may be evaluated using the procedure of O'Neill et al. (*Psychopharmacology* 104:343–350 (1991)). This assay can be used to assess the primary effect of a compound on general motor activity. A decrease in locomotor activity is indicative of a possible sedative effect on the animal, whereas an increase in locomotor activity is indicative of a stimulant effect on the animal.

Locomotor activity of rats (male Sprague-Dawley (Harlan) weighing 200–250 gm) is measured for 2 hrs in photocell cages immediately after administration of the compound. Prior to the test day, the animals are placed in the activity cages for 3 hrs to familiarize them with the experimental environment. On the test day, the animals are placed in the photocell cages and then injected with compound 1.5 hrs later.

The photocell cages are standard rodent cages (30 cm×20 cm×40 cm) with four infrared beams crossing the long axis. The animals are under no motivational constraints and are free to move around. Movements from one infrared beam to another (ambulation) are called "cross-over"; successive interruptions of the same beam (vertical and other movements such as grooming) are called "general activity." Results may be reported as the percent of change from control values (i.e., saline injection) for two postinjection periods: 0–60 minutes and 60–120 minutes, respectively.

C. Tail Flick Assay for Analgesic Potential

The effects of compounds on latency in the time between stimulus application and tail flick in rats may be evaluated using the procedure of D'Amour and Smith, *J. Pharmacol. Exp. Ther.* 72:74–79 (1941). Male rats (150–200 g) are acclimated to investigator's handling by taking two-to-three tail-flick latencies. The animals are held by hand such that the tail is placed in the groove of the Tail-Flick meter (IITC Life Sciences, Woodland Hill, Calif., Model 33). The light is focused 3–4 cm from the tip of the tail by a foot-operated switch. The intensity of the incident beam is adjusted to give baseline latencies in the range of 1–4 seconds. Groups of 5–6 rates are used in each treatment. The tail-flick latencies are recorded to the nearest 0.1 seconds and a cut-off time of 10 seconds is established to prevent thermal injury. The results may be expressed as the percent of the maximum latency to remove the tail from the light beam. Maximum latency is 10 seconds. The ability of compounds to increase the latency period between application of stimulus and the tail-flick response with a longer duration than the effect of, for example, morphine, is indicative of analgesic potential.

d. Assay for Activity in the 6-Hydroxydopamine Lesion Model of Parkinsonism

Selective lesions of the brain dopamine pathway using the neurotoxin 6-hydroxydopamine (6-OHDA) in rats can be used as an experimental approach to Parkinson's disease. Unilateral lesions of the nigrostriatal dopamine pathway induce a postural asymmetry which becomes manifested as rotation when the animals are activated by dopamine releasers or dopamine agonists. When amphetamine and other stimulant drugs that induce pre-synaptic release of dopamine from intact nerve terminals are administered, the rats rotate in a direction ipsilateral to the lesion. In contrast, when the rats are injected with post-synaptic dopamine receptor agonist, such as apomorphine, they turn in a contralateral direction, due to the development of supersensitive dopamine receptors in the lesioned side. Thus, the 6-OHDA model can be used to determine if a suspected dopaminergic agent is active, and to differentiate whether such action is pre- or post-synaptic.

The effects of library compounds on rotational behavior in 6-hydroxydopamine denervated rates may be evaluated using the procedure of Ungerstedt and Arbutknott, *Brain Res.* 24:485–493 (1970). Male Sprague-Dawley rats (Zivic Miller) weighing 170–200 gm can be used in the 6-OHDA procedure. The ascending nigrostriatal dopamine pathway is lesioned by unilateral stereotaxic injection of 6-OHDA (8.0 μg) into one substantia nigra. All injections of 6-OHDA are preceded by desmethylimipramine (25 mg/kg i.p.) and pargyline (75 mg/kg i.p.) approximately 30 minutes prior to undergoing stereotaxic surgery for 6-OHDA infusion into the substantia nigra. After one week of recovery from surgery, the effectiveness of the lesions is verified by noting the response of the animals to apomorphine (0.2 mg/kg, s.c.). Only rats with a minimum rate of 80 contralateral turns per 30 minutes (a sign of more than 80%–90% dopamine depletion after a 6-OHDA lesion) are used. Two weeks later, the selected rats are tested with the compounds and reference compounds using an automated rotometer system to record the number and direction of rotations. In order to distinguish spontaneous (non-specific) rotations from induced rotations (specific to the effect of the drug), each rat is used as its own control, employing the following procedure:

The rat is placed in the rotometer system for acclimation for 15 minutes, the vehicle administered subcutaneously, the rat's rotations recorded for one hour, then test compound is administered s.c. and rotations again recorded for one hour. The number of ipsilateral rotations induced by vehicle is then compared to the number of ipsilateral rotations induced by test compound. Statistical analysis of the data is carried out sing Student's t-test (paired). The results may be reported as the percentage change of ipsilateral rotations, relative to control, per one hour interval.

e. Assay for Activity in the Haloperidol-induced Catalepsy Model

The effects of compounds on haloperidol-induced catalepsy in rats ay be evaluated using the procedure of Emerich et al., *Pharmocol, Biochem, Behav.* 38:875–880 (1991). The effects may be compared to those of a known neuronal receptor-activating compound, e.g., nicotine as in the following exemplary assay.

Nicotine (as the tartrate salt) and compounds are given i.p. 10 minutes before injection of haloperidol (2 mg/kg i.p.). Catalepsy measurements are taken 15, 30, 60, 90, 120 minutes post-haloperidol injection. The percent reduction in catalepsy is calculated based on rats treated with haloperidol alone.

5. Other Assays

Other assays that may be used to identify compounds with potential therapeutic activity are known to those of skill in the art (see e.g., U.S. Pat. Nos. 5,665,543; 5,071,773 and 4,980,281).

6. Antibacterial Assays

The compounds and libraries provided herein may be used to screen for compounds that possess antibacterial activity against a wide variety of Gram positive and Gram negative bacilli. Compounds of particular interest will be effective against diseases caused by Streptococci, *H. influenza, E. coli*, Klebsiella, Enterobacter, Salmonella, and Serratia. Standard in vitro agar dilution assays which are well known to those of ordinary skill in the art may be used in the screening. The libraries provided herein may also be used to screen for compounds that possess antibacterial activity against Staphylococcus bacteria, in particular *Staphylococcus aureus*. Assays which are useful in screening may be found in U.S. Pat. Nos. 5,610,196, 5,391,492, 5,192,742, 4,431,809, 4,304,856, 4,283,390, 4,227,002, 3,856,937 and 3,338,786.

In one assay, the microorganisms tested may be obtained from the American Type Culture Collection (Rockville, Md.). They are *Bacillus subtilis* ATCC 9372 *Brevibacterium ammoniagenes* ATCC 6872, *Staphylococcus aureus* ATCC 12598, *Streptococus mutans* ATCC 25175, *Propionibacterium acnes* ATCC 11827, *Pseudimonas aeruginosa* ATCC 10145, *Enterobacter aerogenes* ATCC 13048, *Eschericia coli* ATCC 9637, *Proteus vulgaris* ATCC 133315, *Saccharomyces cerevisiae* ATCC 7754, *Candida utilis* ATCC 9226, *Pityrosporum ovale* ATCC 14521, *Penicillium chrysogenum* ATCC 10106 and *Trichophyton mentagrophytes* ATCC 18748. These microorganisms are then cultured as described in U.S. Pat. No. 5,610,196, then used in the following assay.

The minimum inhibitory concentration (MIC) of the compounds provided herein may be determined using a two-fold serial broth dilution. Each test compound is dissolved in DMF and 30 $\mu$L of this sample is dissolved in 3 mL of the applicable medium. A 30 $\mu$L sample of the previously described culture of each microorganism is added to the various medium solutions. After two days, the cultures of *B. subtilis, S. cerevisiae, C utilis, B. ammoniagenes, E. aerogenes, S. aureus, S. mutans, P. acnes, P. aeruginosa, E. coli* and *P. vulgaris* are examined for turbidity (OD at 660 nm). The fungi, *P. ovale, P. chysogenum* and *T. mentagrophytes*, are examined visually for growth at 3 days (*P. ovale*) and 5 days (*P. chrysogeum* and *T. meuagrophytes*). The MIC is determined as the lowest concentration for each compound that no growth was observed.

In another exemplary assay, testing of the libraries provided herein is indicated for antibiotic activity against organisms such as *Staphylococcus aureus* and *Bacillus subtilis* ATCC 6633. The bioassays are conveniently performed by the agar-well plate test.

Another assay which may be used to screen the libraries provided herein involves screening for antibiotic activity by bioassay on *Staphylococcus aureus* V573, using the conventional hole in plate method.

Further methods involve an adaptation of the *Staphylococcus aureus* turbidimetric assay for tetracycline that is described in "Assay Methods of Antibiotics, a Laboratory Manual" by Grove & Randall, Medical Encyclopedia, Inc. (1955), pages 48–52.

A bioassay for the antibacterial activity of A-23187 has been described by J. E. Westhead *Antimicrobial Agents and Chemotherapy* 11 (5), 916–918 (1977). The test organism for this bioassay is *Staphylococcus aureus* (H-Heatley strain, NRRL B-314).

Other methods include assay by either agar-diffusion or turbidimetric analysis. Test organisms suitable for use include *Staphylococcus aureus, Bacillus subtilis,* and *Micrococcus luteus*. The bioassay is preferably performed employing *S. aureus* NRRL B-314 in a turbidimetric test or by employing *Bacillus subtilis* ATCC 6633 in a paper disc agar diffusion plate test. The bioassay may also be conveniently performed by an automated turbidometric method.

F. Pharmaceutical Compositions Containing the Compounds

1. Formulation

The pharmaceutical compositions provided herein contain therapeutically effective amounts of one or more of the compounds provided herein or identified by screening the libraries provided herein. These compounds are dihydropyridones, N-acyldihydropyridones, tetrahydropyridones, pyridines, aminopyridines, N-acyltetrahydropyridines and tetrahydropyridines. These compounds should be useful for the prevention or treatment of neurological disorders, such as schizophrenia, Alzheimer's disease, disorders of extrapyramidal motor function, such as Parkinson's disease, progressive supramuscular palsy, Huntington's disease, Gilles de la Tourette syndrome and tardive dyskinesia, obesity, severe pain, drug and tobacco withdrawal, respiration, mood and emotional disorders such as depression, anxiety and psychosis, motor control and function, focus and attention disorders, concentration disorders, memory loss, cognitive impairment, dementia (including AIDS dementia), neurodegenerative disorders, epilepsy, cardiovascular dysfunction including hypertension and cardiac arrhythmias, convulsive disorders, eating disorders, including bulimia and anorexia, autonomic disorders including dysfunction of gastrointestinal motility and function such as inflammatory bowel disease, irritable bowel syndrome, diarrhea, constipation, gastric acid secretion and ulcers, comedication in surgical procedures and pheochromocytoma; or heart insufficiency, hyperprolactinemia, bacterial infections, asthma or arthritis.

The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel *Introduction to Pharmaceutical Dosage Forms, Fourth Edition* 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, acids, bases, solvates, hydrates or prodrugs prior to formulation, as described above. The concentrations of the compounds in the compositions are effective for delivery of an amount, upon administration, that ameliorates the symptoms of the fungal infection.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems (see, e.g., U.S. Pat. Nos. 5,401,629, 5,436,128, 5,670,113, 5,369,028, 5,610,196, 5,391,492, 5,192,742, 4,431,809, 4,304,856, 4,283,390, 4,227,002, 3,856,937 and 3,338,786) and then extrapolated therefrom for dosages for humans.

The concentration of active compound in the drug composition will depend on absorption, inactivation and excretion rates of the active compound, the physicochemical characteristics of the compound, the dosage schedule, and amount administered as well as other factors known to those of skill in the art.

Typically a therapeutically effective dosage should produce a serum concentration of active ingredient of from about 0.1 ng/ml to about 50–100 $\mu$g/mi. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Preferred pharmaceutically acceptable derivatives include acids, bases, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating or treating the fungal infection for which treatment is contemplated. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, which includes orally, parenterally, rectally and topically and locally depending upon the disorder being treated. For oral administration, capsules and tablets are presently preferred. The compositions are in liquid, semi-liquid or solid form and are formulated in a manner suitable for each route of administration. Preferred modes of administration include parenteral and oral modes of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%–100% active ingredient, preferably 0.1–85%, typically 75–95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as beta-adrenergic blocker (for example atenolol), a calcium channel blocker (for example nifedipine), an angiotensin converting enzyme (ACE) inhibitor (for example lisinopril), a diuretic (for example furosemide or hydrochlorothiazide), an endothelin converting enzyme (ECE) inhibitor (for example phosphoramidon), a neutral endopeptidase (NEP) inhibitor, an HMGCoA reductase inhibitor, a nitric oxide donor, an anti-oxidant, a vasodilator, a dopamine agonist, a neuroprotective agent, a steroid, a beta-agonist, an anti-coagulant, or a thrombolytic agent. It is to be understood that such combination therapy constitutes a further aspect of the compositions and methods of treatment provided herein.

2. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumia hydrate. Sweetening agents include sucrose, lactose, mannitol and artificial sweetening agents such as sodium cyclamate and saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. For example, if the compound is used for treating asthma or hypertension, it may be used with other bronchodilators and antihypertensive agents, respectively. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, include organic adds and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

3. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%–10% isotonic solutions, pH about 5–7, with appropriate salts.

5. Formulations for Other Routes of Administration

Depending upon the condition treated other routes of administration, such as topical application, transdermal patches, an rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Articles of Manufacture

The pharmaceutical compositions containing compounds or pharmaceutically acceptable derivatives may be packaged as articles of manufacture containing packaging material, the composition provided herein, which is effective for ameliorating the symptoms of neurological disorders, such as one of schizophrenia, Alzheimer's disease, disorders of extrapyramidal motor function, such as Parkinson's disease, progressive supramuscular palsy, Huntington's disease, Gilles de la Tourette syndrome and tardive dyskinesia, obesity, severe pain, drug and tobacco withdrawal, respiration, mood and emotional disorders such as depression, anxiety and psychosis, motor control and function, focus and attention disorders, concentration disorders, memory loss, cognitive impairment, dementia (including AIDS dementia), neurodegenerative disorders, epilepsy, cardiovascular dysfunction including hypertension and cardiac arrhythmias, convulsive disorders, eating disorders, including bulimia and anorexia, autonomic disorders including dysfunction of gastrointestinal motility and function such as inflammatory bowel disease, irritable bowel syndrome, diarrhea, constipation, gastric acid secretion and ulcers, comedication in surgical procedures and pheochromocytoma; or heart insufficiency, hyperprolactinemia, bacterial infections, asthma and arthritis at an $IC_{50}$ of less than about 500 $\mu M$ as measured in a standard assay for the selected indication, within the packaging material, and a label that indicates that the composition containing the compound or derivative thereof is used in treatment or prevention of a neurological disorder, such as schizophrenia, Alzheimer's disease, disorders of extrapyramidal motor function, such as Parkinson's disease, progressive supramuscular palsy, Huntington's disease, Gilles de la Tourette syndrome and tardive dyskinesia, obesity, severe pain, drug and tobacco withdrawal, respiration, mood and emotional disorders such as depression, anxiety and psychosis, motor control and function, focus and attention disorders, concentration disorders, memory loss, cognitive impairment, dementia (including AIDS dementia), neurodegenerative disorders, epilepsy, cardiovascular dysfunction including hypertension and cardiac arrhythmias, convulsive disorders, eating disorders, including bulimia and anorexia, autonomic disorders including dysfunction of gastrointestinal motility and function such as inflammatory bowel disease, irritable bowel syndrome, diarrhea, constipation, gastric acid secretion and ulcers, comedication in surgical procedures and pheochromocytoma; or heart insufficiency, hyperprolactinemia, bacterial infections, asthma and arthritis.

The following examples are included for illustrative purposes only and are not intended to limit the scope of the invention.

EXAMPLE 1

2-Methyl-2,3-dihydropyridone

To a suspension of chloroformate resin (0.5 g, 0.41 mmol-based on loading of 0.81 mmol/g) in THF (6 mL) in a 15 mL polypropylene tube fitted with a frit was added a pre-mixed solution of 4-methoxypyridine (53 mg, 0.48 mmol) and a solution of methylmagnesium chloride (3.0 M THF solution, 0.27 mL, 0.81 mmol) in THF (3 mL). The resulting reaction mixture was vigorously mixed then immediately filtered and washed with a 1:1 mixture of 3 M aqueous HCl/THF solution (5×5 mL), 3M HCl (3×5 mL) MeOH (3×5 mL), DMF (3×5 mL, $CH_2Cl_2$(3×8 mL) and diethyl ether (4×5 mL) then dried in vacuo to afford the resin bound 2-methyl-2,3-dihydropyridone. Analysis of a small sample of beads (3 mg) by FTIR confirmed the dihydropyridone is on solid support. FTIR (KBr): 1729, 1675, 1602 $cm^{-1}$. To a suspension of the resin bound dihydropyridone in the THF (8 mL) was added a 4.37 M solution of NaOMe/MeOH (93 $\mu l$, 0.41 mmol) and the reaction mixture was agitated for 1 h. Ammonium chloride (5 eq., 100 mg) was then added and agitation was continued overnight. The mixture was filtered and the resin was washed THF (3×5 mL). The filtrates were passed through a plug of Celite (Celite was washed with THF). The filtrate was collected, concentrated and dried under reduced pressure to give 2-methyl-2,3-dihydropyridone as a pale yellow oil (65% yield, 98% purity HPLC). $^1H$ NMR (300 MHz, $CDCl_3$) $\delta 1.32$ (d, 3H), 2.38 (m, 2H), 3.82 (m, 1H), 5.02 (d, 1H), 5.3 (br, 1H), 7.17 (t, 1H). $^{13}C$ NMR (75 MHz, $CDCl_3$) $\delta 20.19$, 43.92, 49.16, 98.28, 152.00, 193.43. LRMS (EI) m/z 111 (100), 96 (53), 82 (15), 69 (66). HRMS (FAB) calcd for $(M+H)^+$ $C_6H_{10}NO$ 112.0762, found 112.0759.

EXAMPLE 2

2-Ethyl-2,3-dihydropyridone

The procedure of Example 1 was used except ethylmagnesium bromide (1.0 M in THF, 2.0 mL, 2.0 mmol) was used in place of methylmagnesium chloride. FTIR (KBr) of the support-bound 2-ethyl-2,3-dihydropyridone: 1727, 1678, 1602 $cm^{-1}$. 2-Ethyl-2,3-dihydropyridone was obtained as a pale yellow oil (31% yield, 94% pure by HPLC). $^1H$ NMR (300 MHz, $CDCl_3$) $\delta 0.98$ (t, 3H), 1.67 (m, 2H), 2.38 (m, 2H), 3.59 (m, 1H), 4.99 (d, 1H), 5.52 (br, 1H), 7.20 (t, 1H). $^{13}C$ NMR (75 MHz, $CDCl_3$) $\delta 9.90$, 27.19, 41.70, 54.81, 98.87, 151.60, 193.47. LRMS (EI) m/z 125 (50), 96 (100), 78 (9), 68 (20).

EXAMPLE 3

2-Isopropyl-2,3-dihydropyridone

The procedure of Example 1 was used except isopropylmagnesium bromide (2.0 M in THF, 1.0 mL, 2.0 mmol was used in place of methylmagnesium chloride. FTIR (KBr) of the support-bound 2-isopropyl-2,3-diyhydropyridone: 1724, 1678, 1605 $cm^{-1}$. 2-Isopropyl-2,3-dihydropyridone was obtained as a pale yellow oil (48% yield, 93% pure by HPLC). $^1H$ NMR (300 MHz, $CDCl_3$) $\delta 0.98$ (dd, 6H), 1.88 (m, 1H), 2.37 (m, 2H), 3.47 (m, 1H), 4.98 (d, 1H), 5.64 (br, 1H), 7.24 (t, 1H). $^{13}C$ NMR (75 MHz, $CDCl_3$) $\delta 118.22$, 18.53, 31.19, 38.84, 58.92, 98.58, 152.06, 193.68. LRMS (EI) m/z 139 (40), 96 (100), 78 (9), 68 (25).

EXAMPLE 4

2-Isobutyl-2,3-dihydropyridone

The procedure of Example 1 was used except isobutylmagnesium chloride (2.0 M in diethyl ether, 1.0 mL, 2.0 mmol) was used in place of methylmagnesium chloride. FTIR (KBr) of the support-bound 2-isobutyl-2,3-dihydropyridone: 1729, 1678, 1605 $cm^{-1}$. 2-Isobutyl-2,3-dihydropyridone was obtained as a pale yellow oil (56% yield, 95% pure by HPLC). $^1H$ NMR 300 MHz, $CDCl_3$) $\delta 0.94$ (dd, 6H), 1.42 (m, 1H), 1.66 (m, 2H), 2.35 (m, 2H), 3.74 (m, 1H), 4.96 (d, 1H), 6.09 (br, 1H), 7.22 (t, 1H). $^{13}C$ NMR (75 MHz, $CDCl_3$) $\delta 22.93$, 23.13, 24.77, 42.64, 43.50, 51.50, 98.55, 152.44, 193.76. LRMS (EI) m/z 153 (40), 110 (7), 96 (100), 78 (7), 69 (22).

EXAMPLE 5

2-t-Butyl-2,3-dihydropyridone

The procedure of Example 1 was used except t-butylmagnesium chloride (2.0 M in diethyl ether, 1.0 mL, 2.0 mmol) was used in place of methylmagnesium chloride. FTIR (KBr) of the support-bound 2-t-butyl-2,3-dihydropyridone: 1724, 1678, 1605 cm$^{-1}$. 2-t-Butyl-2,3-dihydropyridone was obtained as a pale yellow oil (32% yield, 85% pure by HPLC). $^1$H NMR (300 MHz, CDCl$_3$) δ0.98 (s, 9H), 2.41 (m, 2H), 3.36 (dd, 1H), 5.00 (d, 1H), 5.41 (br, 1H), 7.25 (t, 1H). $^{13}$C NMR (75 MHz, CDCl$_3$) δ26.07, 33.15, 37.77, 62.53, 98.70, 152.20, 193.91. LRMS (EI) m/z 153 (29), 96 (100), 78 (8), 68 (14).

EXAMPLE 6

2-Phenyl-2,3-dihydropyridone

The procedure of Example 1 was used except phenylmagnesium bromide (1.0 M in THF, 2.0 mL, 2.0 mmol) was used in place of methylmagnesium chloride. FTIR (KBr) of the support-bound 2-phenyl-2,3-dihydropyridone: 1729, 1678, 1605 cm$^{-1}$. 2-Phenyl-2,3-dihydropyridone was obtained as a pale yellow oil (67% yield, 95% pure by HPLC). $^1$H NMR (300 MHz, CDCl$_3$) δ2.34 (dd, 1H), 2.58 (dd, 1H), 4.65 (dd, 1H), 4.95 (d, 1H), 6.20 (br, 1H), 7.29 (m, 5H). $^{13}$C NMR (75 MHz, CDCl$_3$) δ44.43, 58.33, 98.89, 126.80, 128.61, 129.14, 140.10, 152.32, 192.67. LRMS (EI) m/z 173 (63), 144 (7), 104 (100), 78 (18).

EXAMPLE 7

2-Benzyl-2,3-dihydropyridone

The procedure of Example 1 was used except benzylmagnesium chloride (freshly prepared from magnesium turnings and benzyl chloride, ~2 M in THF, 1.0 mL, 2.0 mmol) was used in place of methylmagnesium chloride. FTIR (KBr) of the support-bound 2-benzyl-2,3-dihydropyridone: 1729, 1678, 1605 cm$^{-1}$. 2-Benzyl-2,3-dihydropyridone was obtained as a pale yellow oil (35% yield, 95% pure by HPLC). $^1$H NMR (300 MHz, CDCl$_3$) δ2.47 (m, 2H), 2.88 (m, 2H), 3.85 (m, 1H), 5.01 (d, 1H), 5.12 (br, 1H), 7.08–7.37 (m, 6H). $^{13}$C NMR (75 MHz, CDCl$_3$) δ40.73, 42.71, 54.83, 99.98, 127.66, 128.98, 129.48, 137.12, 151.48, 193.27. LRMS (EI) m/z 187(5), 117 (3), 96 (100), 91 (11).

EXAMPLE 8

2-Methyl-6-isopropyl-2,3,5,6-tetrahydropyridone

Isopropylmagnesium chloride (2.0 M in THF, 0.3 mL, 0.6 mmol) was slowly added via syringe to cuprous iodide (1115 mg, 0.6 mmol) in THF (3 mL) at −25° C. in a septum vial. The resulting heterogenous mixture was stirred at −25° C. for 10 min. and then cooled to −78° C. Boron trifluoride diethyl etherate was added. The mixture stayed heterogeneous. After 10 min., the cold methyl cuprate suspension was added to a suspension of resin-bound 2-methyl-2,3-dihydropyridone (366 mg, 0.82 mmol/g, 0.3 mmol) in THF (3 mL) at rt in a 15 mL poplypropylene tube fitted with a frit via cannula. The resulting suspension was vented several times until it warmed to ambient temperature. The reaction tube was attached to a rotor and rotated for 3 h. The resin was washed with 1:1 THF/1 M HCl (4×4 mL), 1 M HCl (4×2 mL), MeOH (3×5 mL), DMF (3×5 mL), and CH$_2$Cl$_2$ (4×8 mL). The resulting resin was suspended in CH$_2$Cl$_2$ (2 mL) and TFA (4 mL) was added. The resulting mixture was agitated for 2–3 days. The mixture was then filtered and washed with CH$_2$Cl$_2$ (2×5 mL) and MeOH (2×5 mL)) The combined filtrates were concentrated and dried under vacuum to give the TFA salt of 2-methyl-6-isopropyl-2,3,5,6-tetrahydropyridone (32% yield, 90% pure). The free base of 2-methyl-6-isopropyl-2,3,5,6-tetrahydropyridone was characterized. $^1$H NMR (300 MHz, CDCl$_3$) δ0.91 (d, 6H, J=6.0 Hz), 1.25 (d, 3H, J=8.4 Hz), 1.38 (m, 1H), 1.70 (m, 2H), 2.05 (m, 2H), 2.42 (m, 2H), 3.03 (m, 1H), 3.42 (m, 1H). LRMS (EI) m/z 169 (5), 154 (6), 112 (100), 70 (79). HRMS (FAB) calcd for (M+H)+ C$_{10}$H$_{20}$NO 170.1545, found 170.1541.

EXAMPLE 9

2,6-Dimethyl-2,3,5,6-tetrahydropyridone

The synthetic procedures in Example 8 were used except methylmagnesium chloride (1.0 M, 0.6 mL, 0.3 mmol) was used in place of isopropylmagnesium chloride. The TFA salt of 2,6-dimethyl-2,3,5,6-tetrahydropyridone was obtained (29% yield, 95% pure). The free base: LRMS (EI) m/z 127 (20), 112 (28), 84 (18), 70 (100), 56 (10).

EXAMPLE 10

2-Methyl-6-phenyl-2,3,5,6-tetrahydropyridone

The synthetic procedures of Example 8 were used except phenylmagnesium chloride (1.0 M, 0.6 mL, 0.3 mmol was used in place of isopropylmagnesium chloride. The TFA salt of 2-methyl-6-phenyl-2,3,5,6-tetrahydropyridone was obtained (27% yield, 86% pure). The free base: LRMS (EI) m/z 189 (45), 146 (50) 132 (45), 104 (10), 77 (35).

EXAMPLE 11

2,4-Diphenylpyridine

Anhydrous CeCl$_3$ (powder, 250 mg, 1.0 mmol) was stirred in a round bottom septum glass tube at 135° C. under vacuum for 3 h. The vacuum was removed and the CeCl$_3$ was kept under Ar and cooled in an ice bath. THF (3 mL) was added and the resulting suspension was stirred at rt overnight. Phenylmagnesium bromide (1.0 M in THF, 0.62 mL, 0.62 mmol) was added at 0° C. and the resulting suspension was stirred at 0° C. for 1.5–2 h. The mixture was cannulated into THF (3 mL) pre-swollen 2-phenyl-2,3-dihydropyridone resin (500 mg, 0.82 mmol/g, 0.41 mmol) and the resulting slurry was agitated for 3 h-overnight on a rotor. The resin was filtered, washed with 1/1 1 N AcOH (aqueous)/THF (4×4 mL), 1 N AcOH (4×2 mL), MeOH (3×2 mL), DMF (3×3 mL), THF (3×3 mL), and CH$_2$Cl$_2$ (3×3 mL). The resin was suspended in CH$_2$Cl$_2$ (5 mL) in a glass tube fitted with a gas dispensing disc, and TFA (15 mL) was added. Oxygen was bubbled through the resulting suspension for 2 days and 1:2 CH$_2$Cl$_2$/TFA was replenished as needed. The resin was filtered, washed with CH$_2$Cl$_2$ (2×2 mL) and MeOH (2×2 mL). The combined filtrates and washings were concentrated in speedvac to give the TFA salt of the product (24%). The free base was characterized: $^1$H NMR (300 MHz, CDCl$_3$) δ7.47 (m, 7H), 7.70 (dd, 2H), 7.94 (s, 1H), 8.05 (dd, 2H), 8.74 (d, 1H). $^{13}$C NMR (75 MHz, CDCl$_3$) δ118.82, 120.28, 127.04, 127.09, 128.78, 128.97, 129.05, 129.13, 138.50, 139.45, 149.31, 150.07, 158.07. LRMS (EI) m/z 231(100), 202 (21), 154(16), 127(11), 102(16), 77(19).

EXAMPLE 12

2-Phenyl-4-tolypryridine

The synthetic procedures as in Example 11 were used except tolylmagnesium bromide (1.0 M in diethyl ether, 0.62 mmol) was used in place of phenylmagnesium bromide. The TFA salt of the product was obtained (23%). Free base: $^1$H NMR (300 MHz, CDCl$_3$) δ2.43 (s, 3H), 7.02–7.50 (m, 6H), 7.60 (d, 2H), 7.97 (s, 1H), 8.04 (d, 2H) 8.72 (d, 1H). $^{13}$C NMR (75 MHz, CDCl$_3$) δ21.26, 118.57, 120.28, 126.90, 127.03, 128.76, 128.97, 129.84, 135.52, 139.19, 139.56, 149.16, 150.03, 158.03. LRMS (EI) m/z 245(100), 230 (57), 202 (10), 115 (19), 127 (11), 77(9).

EXAMPLE 13

2-Methyl-4-tolylpyridine

Same synthetic procedures as in Example 11 were used except 2-methyl-2,3-dihydropyridone resin (500 mg, 0.82 mmol/g, 0.41 mmol) and tolymagnesium bromide (1.0 M in diethyl ether, 0.62 mL, 0.62 mmol) were used in place of 2-phenyl-2,3-dihydropyridone resin and phenylmagnesium bromide, respectively. The TFA salt of the product was obtained (21%). Free base: $^1$H NMR (300 MHz, CDCl$_3$) δ2.67 (s, 3H), 7.40–7.53 (m, 5H), 7.65 (m, 2H), 8.60 (d, 1H). LRMS (EI) m/z 169 (100), 154 (7), 141 (18), 127 (8), 115(27), 102(9), 77(18).

EXAMPLE 14

1-Benzoyl-2-methyl-2,3-dihydropyridone

To THF (5 mL) swollen Wang resin (hydroxymethyl polystyrene and hydroxy S TentaGel work the same, 1 g, 0.82 mmol/mg, 0.82 mmol) in a 25 mL polypropylene tube fitted with a frit was added solutions of 4-hydroxypyridine in DMF (1 M, 4 mL, 4 mmol), triphenylphosphine in THF (0.5 M, 4 mL, 2 mmol) and DIAD (0.5 M, 4mL, 2 mmol). The resulting slurry was agitated overnight on a rotor. The resin was filtered and washed with DMF (3×6 mL), MeOH (3×4 mL), THF (3×6 mL), dichloromethane (3×6 mL) and ether (3×4 mL). The resin was dried under vacuo. IR analysis of the resin show a sharp and strong adsorption at 1640 cm$^{-1}$. To THF (3 mL) swollen 4-methoxypyridine (300 mg, ~0.2 mmol) resin in a 6 mL polypropylene tube fitted with a frit was added benzoyl chloride (neat, 50 μl, 0.43 mmol). Upon mixing, methylmagnesium chloride (3.0 M in THF, 0.14 mL, 0.42 mmol) was added and the resulting slurry was agitated for 2–3 h. The resin was washed with 1:1 THF/water (3×3 mL), water (3×2 mL), MeOH (3×2 mL), dichloromethane (3×3 mL) and THF (4×3 mL). The resin was resuspended in THF (3 mL) and HCl (1 M aqueous solution, 1 mL) was added and the resulting mixture was agitated for 1 h. The mixture was filtered and the resin was washed with THF (2×2 mL). The combined filtrate and washings were concentrated in a speedvac overnight to give the crude product (54% yield, 65% pure). LRMS (EI) m/z 162(7), 127(8), 105(100), 100(23), 77(38).

EXAMPLE 15

1-Benzoyl-2-phenyl-2,3-dihydropyridone

The synthetic procedures as in Example 14 were used except phenylmagnesium bromide (1.0 in THF, 0.43 mL, 0.43 mmol) was used in place of methylmagnesium chloride. Crude product (50% yield, 80% pure). LRMS (EI) m/z 277(10), 207(8), 172(9), 105(100), 77(40).

EXAMPLE 16

1-Benzoyl-2-tolyl-2,3-dihydropyridone

The synthetic procedures as in Example 14 were used except tolylmagnesium bromide (1.0 M in diethyl ether, 0.43 mL, 0.43 mmol) was used in place of methylmagnesium chloride. Crude product (58% yield, 76% pure). LRMS (EI) m/z 291(10), 186(14), 105(9), 105(100), 77(33).

EXAMPLE 17

2-Methylpyridin-4-yl-phenylamine

A premixed (1 h) solution of 4-methoxypyridine (218 mg, 2 mmol) and LDA (1.0 M in THF, 2 mL, 2 mmol) in THF (3 mL) under Ar was cannulated into THF (5 mL) swollen chlorodimethylsilylated resin (ArgoGel based) and the resulting slurry was agitated for 3 h. The resin was filtered and washed with 1:1 water/THF (4×5 mL), water (4×3 mL), MeOH (4×3 mL), DMF (4×3 mL), dichloromethane (4×5 mL) and THF (4×5 mL). The resin was re-suspended in THF and methylmagnesium chloride (3.0 M in THF, 0.67 mL, 2 mmol) was added and, upon mixing, benzyl chloroformate (neat, 341 mg, 2 mmol) was added. The resulting slurry was agitated for 2–3 h. The resin was filtered, washed with 1/1 water/THF (4×5 mL), water (4×3 mL), THF (4×3 mL), DMF (4×3 mL), dichloromethane (4×5 mL) and MeOH (4×3 mL). The resin was re-suspended in MeOH (10 mL) and a pre-mixed solution of aniline (186 mg, 2 mmol) and acetic acid (58 μL, 1 mmol) was added follow by sodium cyanoborohydride (1 M in MeOH, 1 mL, 1 mmol). The reaction was agitated for 48 h. The resin was filtered, washed with water (4×3 mL), MeOH (4×3 mL), DMF (4×3 mL), DMF (4×3 mL), THF (4×5 mL) and dichloromethane (4×5 mL). The resin was re-suspended in dichloromethane (6 mL), TFA (2 mL) was added and the suspension was agitated overnight. The mixture was filtered and washed with MeOH (2×2 mL) and dichloromethane (2×3 mL). The combined filtrates were concentrated under vacuo to give the crude TFA salt of the product.

Since modifications will be apparent to those of skill in this art, it is intended that this invention be limited only by the scope of the appended claims.

What is claimed:

1. A method of solid phase synthesis, comprising:
    (a) capturing a substrate on a solid support and activating the substrate to react with a reagent with which the unactivated substrate does not react; and
    (b) reacting the activated substrate on the solid phase with the reagent to give an addition product, wherein:
        the substrate is a heteroaryl compound containing at least one heteroatom that is nitrogen;
        the solid support comprises a functional group that reacts with the nitrogen atom in the substrate to form a heteroarylium ion;
        the heteroarylium is a heteroaryl compound wherein at least one of the heteroatoms is a positively charged nitrogen;
        the reagent comprises an organometallic compound that, in the absence of the resin, does not react with the substrate;
        the organometallic compound is a compound which is an alkali, alkaline earth or transition metal salt of an organic compound; and
        the organic compound is selected from the group consisting of alkanes, alkenes, alkynes, aryls, arylalkanes, heteroaryls and heteroarylalkanes.

2. The method of claim 1, wherein a substituent on the substrate comprises an alkoxy, aryloxy, arylalkoxy, heteroaryloxy, heteroarylalkoxy, dialkylamino, diarylamino, alkylarylamino, alkylthio or arylthio group.

3. The method of claim 1, further comprising the step of:

hydrolyzing the addition product to give a ketone; and wherein a substituent on the substrate comprises a heteroatom that is not substituted with a hydrogen.

4. The method of claim 3, further comprising the step of:

cleaving the ketone from the solid support.

5. The method of claim 4, wherein cleavage is effected by reaction with a metal alkoxide.

6. The method of claim 3, further comprising the step of:

modifying the ketone by a process comprising the step of 1,2-addition giving a modified substrate.

7. The method of claim 6, further comprising the step of:

cleaving the modified substrate from the solid support under acidic conditions.

8. The method of claim 7, wherein cleavage results in reduction of the modified substrate.

9. The method of claim 7, wherein cleavage results in oxidation of the modified substrate.

10. The method of claim 3, further comprising the step of:

modifying the ketone by a process comprising the step of 1,4-addition to produce a modified substrate.

11. The method of claim 10, further comprising the step of:

cleaving the modified substrate from the solid support under acidic conditions.

12. The method of claim 5, wherein:

the substrate is 2-unsubstituted-4-($R^2$)-pyridine, where $R^2$ is selected from the group consisting of alkoxy, aryloxy, arylalkoxy, heteroaryloxy, heteroarylalkoxy, dialkylamino, diarylamino, alkylarylamino, alkylthio and arylthio, and is not substituted further or is substituted at the 3, 5 or 6 positions with one or more Z substituents;

Z is selected from the group consisting of halogen, nitrile, nitro, formyl, alkyl, haloalkyl, polyhaloalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, dialkylaminoalkyl, diarylaminoalkyl, dialkylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl; and the solid support comprises an acylating, sulfonylating or phosphorylating agent.

13. The method of claim 12, wherein:

the functional group on the solid support has the structure:

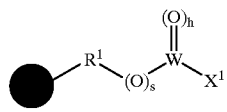

wherein:

$R^1$ is selected from the group consisting of alkylene, arylene, alkylarylene and arylalkylene, and is unsubstituted or substituted with one or more substituents designated Q;

Q is halogen, hydroxy, nitrile, nitro, formyl, mercapto, carboxy, alkyl, haloalkyl, polyhaloalkyl, aminoalkyl, diaminoalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, amino, aminoalkyl, alkylaminoalkyl, dialkylaminoalkyl, arylaminoalkyl, diarylaminoalkyl, alkylamino, dialkylamino, arylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl, such that, when $R^1$ is alkylene or arylalkylene, $R^1$ is a chiral group possessing one or more stereogenic centers; $X^1$ is halo, pseudohalo or carboxy; W is carbon, sulfur or $P(OR^{20})$, where $R^{20}$ is alkyl, aryl or arylalkyl; h is 0–2; s is 0 or 1; and

● is a solid support.

14. The method of claim 13, wherein:

$R^2$ is selected from the group consisting of alkoxy, aryloxy, arylalkoxy, heteroaryloxy and heteroarylalkoxy;

$R^1$ is alkylene;

$X^1$ is halo;

W is carbon;

h is 1; and s is 1.

15. The method of claim 14, wherein:

$R^2$ is alkoxy;

$R^1$ is methylene; and $X^1$ is chloro.

16. The method of claim 15, wherein $R^2$ is methoxy.

17. The method of claim 1, wherein the reagent is selected from the group consisting of alkyl, alkenyl, alkynyl, aryl, arylalkyl, heteroaryl and heteroarylalkyl magnesium halide, lithium and cadmium reagents.

18. The method of claim 1, wherein:
the substrate is a 2-unsubstituted-4-($R^2$)-pyridine, where $R^2$ is selected from the group consisting of alkoxy, aryloxy, arylalkoxy, heteroaryloxy, heteroarylalkoxy, dialkylamino, diarylamino, alkylarylamino, alkylthio and arylthio, and is not substituted further or is substituted at the 3, 5 or 6 positions with one or more Z substituents; and each Z is independently halogen, nitrile, nitro, formyl, alkyl, haloalkyl, polyhaloalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidine, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, dialkylaminoalkyl, diarylaminoalkyl, dialkylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl.

19. The method of claim 1, further comprising:
(c) modifying the addition product to give a modified substrate; and
(d) optionally cleaving the addition product or modified substrate from the solid support; wherein:
the substrate is selected from the group consisting of pyridine, pyrimidine, pyrazine, quinoline, isoquinoline, pyridazine, phthalazine, naphthyridine, quinoxaline, quinazoline, cinnoline, pteridine, phenanthridine, acridine, perimidine, phenanthroline and phenazine, and is unsubstituted or is substituted with one or more Z substituents;
each Z is independently halogen, nitrile, nitro, formyl, alkyl, haloalkyl, polyhaloalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidine, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, dialkylaminoalkyl, diarylaminoalkyl, dialkylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl, arylaminosulfonyl or diarylaminosulfonyl;
wherein:
modification of the addition product comprises the processes of electrophilic substitution, nucleophilic addition and enolate alkylation; cleavage of the addition product from the solid support comprises treatment with acid or base and optionally with an oxidant or reductant; the substrate is a 2-unsubstituted-4-($R^2$)-pyridine, where $R^2$ is selected from the group consisting of alkoxy, aryloxy, arylalkoxy, heteroaryloxy, heteroarylalkoxy, dialkylamino, diarylamino, alkylarylamino, alkylthio and arylthio, and is not substituted further or is substituted at the 3, 5 or 6 positions with one or more Z substituents;
the reagent is selected from the group consisting of alkyl, alkenyl, alkynyl, aryl, arylalkyl, heteroaryl and heteroarylalkyl magnesium halide and lithium reagents;
the acid is trifluoroacetic acid;
the base is sodium methoxide;
the oxidant is $O_2$; and
the reductant is triethylsilane.

20. The method of claim 13, wherein:
$R^2$ is selected from the group consisting of alkoxy, aryloxy, arylalkoxy, heteroaryloxy and heteroarylalkoxy;
$R^1$ is alkylene; and
$X^1$ is chloro.

21. The method of claim 20, wherein $R^2$ is alkoxy and $R^1$ is methylene.

22. The method of claim 20, wherein $R^2$ is methoxy.

23. The method of claim 1, wherein the resulting product is selected from the group consisting of dihydropyridones, N-acyldihydropyridones, tetrahydropyridones, pyridines, aminopyridines, N-acyltetrahydropyridines and tetrahydropyridines.

24. The method of claim 23, wherein the product is selected from compounds that have the formulae:

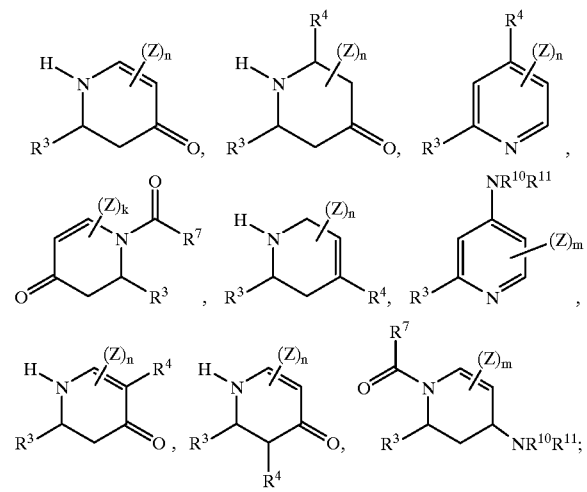

wherein:
$R^3$ is alkyl, alkenyl, alkynyl, aryl, arylalkyl, heteroaryl or heteroarylalkyl;
$R^4$ is selected from hydrogen, alkyl, aryl, heteroaryl, arylalkyl, heteroarylalkyl, halo, amino, azido, cyano, nitro, alkylcarbonyl, arylcarbonyl, heteroarylcarbonyl, arylalkylcarbonyl, heteroarylalkylcarbonyl, carboxy, alkoxycarbonyl, aryloxycarbonyl, heteroaryloxycarbonyl, arylalkoxycarbonyl, heteroarylalkoxycarbonyl, thio, alkylthio and arylthio, and may be further substituted with one or more Z substituents;

each Z is independently halogen, nitrile, nitro, formyl, alkyl, heloalkyl, polyhaloalkyl, alkenyl containing 1 to 2 double bonds, alkynyl containing 1 to 2 triple bonds, cycloalkyl, cycloalkylalkyl, aryl, heteroaryl, arylalkyl, heteroarylalkyl, alkylidene, arylalkylidene, alkylcarbonyl, arylcarbonyl, heteroarylcarbonyl, alkoxycarbonyl, alkoxycarbonylalkyl, aryloxycarbonyl, aryloxycarbonylalkyl, aminocarbonyl, alkylaminocarbonyl, dialkylaminocarbonyl, arylaminocarbonyl, diarylaminocarbonyl, arylalkylaminocarbonyl, alkoxy, aryloxy, perfluoroalkoxy, alkenyloxy, alkynyloxy, arylalkoxy, dialkylaminoalkyl, diarylaminoalkyl, dialkylamino, diarylamino, alkylarylamino, alkylcarbonylamino, alkoxycarbonylamino, arylcarbonylamino, aryloxycarbonylamino, azido, alkylthio, arylthio, perfluoroalkylthio, thiocyano, isothiocyano, alkylsufinyl, alkylsufonyl, arylsufinyl, arylsufonyl, aminosulfonyl, alkylaminosulfonyl, dialkylaminosulfonyl, arylaminosylfonyl or diarylaminosulfonyl;

$R^7$ is alkyl, aryl, heteroaryl, arylalkyl, heteroarylalkyl, alkoxy, aryloxy, arylalkoxy or heteroaylalkoxy; and $R^{10}$ and $R^{11}$ are each independently hydrogen, alkyl, aryl, heteroayl, arylalkyl or heteroarylalkyl, or together form alkylene or alkenylene.

\* \* \* \* \*